United States Patent
Shen et al.

(10) Patent No.: US 10,087,442 B2
(45) Date of Patent: Oct. 2, 2018

(54) POLYCATION-FUNCTIONALIZED NANOPOROUS SILICON CARRIER FOR SYSTEMIC DELIVERY OF GENE SILENCING AGENTS

(71) Applicant: The Methodist Hospital, Houston, TX (US)

(72) Inventors: Haifa Shen, Houston, TX (US); Mauro Ferrari, Houston, TX (US); Jianliang Shen, Houston, TX (US); Mingzhen Zhang, Houston, TX (US)

(73) Assignee: The Methodist Hospital, Houston, TX (US)

( * ) Notice: Subject to any disclaimer, the term of this patent is extended or adjusted under 35 U.S.C. 154(b) by 0 days.

(21) Appl. No.: 14/967,165

(22) Filed: Dec. 11, 2015

(65) Prior Publication Data

US 2016/0369269 A1 Dec. 22, 2016

Related U.S. Application Data

(63) Continuation of application No. PCT/US2014/042166, filed on Jun. 12, 2014.

(60) Provisional application No. 61/834,123, filed on Jun. 12, 2013.

(51) Int. Cl.
| | |
|---|---|
| *C12N 15/113* | (2010.01) |
| *A61K 31/713* | (2006.01) |
| *A61K 9/50* | (2006.01) |
| *A61K 9/51* | (2006.01) |
| *A61K 31/7088* | (2006.01) |
| *C12N 15/11* | (2006.01) |

(52) U.S. Cl.
CPC .......... *C12N 15/113* (2013.01); *A61K 9/5031* (2013.01); *A61K 9/5146* (2013.01); *A61K 31/7088* (2013.01); *A61K 31/713* (2013.01); *C12N 15/111* (2013.01); *C12N 2310/14* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 2010/0255103 A1 | 10/2010 | Liong et al. | |
| 2011/0274624 A1* | 11/2011 | Decuzzi | A61K 49/1818 424/9.32 |
| 2013/0071326 A1* | 3/2013 | Martinez | A61K 9/0019 424/1.73 |

FOREIGN PATENT DOCUMENTS

WO WO 2013/056132 A1 4/2013

OTHER PUBLICATIONS

Adams, Brian D. et al., "The micro-ribonucleic acid (miRNA) miR-206 targets the human estrogen receptor-alpha (ERalpha) and represses ERalpha messenger RNA and protein expression in breast cancer cell lines," *Mol. Endocrinol.*, 21(5):1132-1147 (May 2007).
Akinc, Akin et al., "A combinatorial library of lipid-like materials for delivery of RNAi therapeutics," *Nat. Biotechnol.*, 26(5):561-569 (May 2008).
Al-Hajj, Muhammad et al., "Therapeutic implications of cancer stem cells," *Curr. Opin. Genet. Dev.*, 14(1):43-47 (Feb. 2004).
Aliabadi, Hamidreza M. et al., "Supramolecular assemblies in functional siRNA delivery: where do we stand?" *Biomaterials*, 33(8):2546-2569 (Mar. 2012).
Ananta, Jeyarama S. et al., "Geometrical confinement of gadolinium-based contrast agents in nanoporous particles enhances T1 contrast," *Nat. Nanotechnol.*, 5(11):815-821 (Nov. 2010).
Ballarin-Gonzalez, Borja et al., "Polycation-based nanoparticles for RNAi-mediated cancer treatment," *Cancer Lett.*, 352(1):66-80 (Sep. 28, 2014).
Baluk, Peter et al., "Cellular abnormalities of blood vessels as targets in cancer," *Curr. Opin. Genet. Dev.*, 15(1):102-111 (Feb. 2005).
Batist, Gerald et al., "Reduced cardiotoxicity and preserved antitumor efficacy of liposome-encapsulated doxorubicin and cyclophosphamide compared with conventional doxorubicin and cyclophosphamide in a randomized, multicenter trial of metastatic breast cancer," *J. Clin. Oncol.*, 19(5):1444-1454 (Mar. 1, 2001).
Bellocq, Nathalie C. et al., "Transferrin-containing, cyclodextrin polymer-based particles for tumor-targeted gene delivery," *Bioconjug. Chem.*, 14(6):1122-1132 (Nov. 4, 2003).
Berns, Katrien et al., "A functional genetic approach identifies the PI3K pathway as a major determinant of trastuzumab resistance in breast cancer," *Cancer Cell.*, 12(4):395-402 (Oct. 2007).
Bhattarai, Shanta Raj et al., "Enhanced gene and siRNA delivery by polycation-modified mesoporous silica nanoparticles loaded with chloroquine," *Pharm. Res.*, 27(12):2556-2568 (2010).
Canman, CE and Lim, DS, "The role of ATM in DNA damage responses and cancer," *Oncogene*, 17(25):3301-3308, (Dec. 24, 1998).
Cantley, LC et al., "AACR Cancer Progress Report 2012," *Clin. Cancer Res.*, 18(21 Suppl):S1-S100 (2012).
Castillo, Betzaida et al., "Intracellular delivery of siRNA by polycationic superparamagnetic nanoparticles," 2012, *J. Drug Del.*, 2012:id218940, 12 pages.
Chiappini, Ciro et al., "Tailored porous silicon microparticles: fabrication and properties," *Chem. Phys. Chem.*, 11(5):1029-1035 (Apr. 6, 2010).

(Continued)

*Primary Examiner* — Susan T Tran
(74) *Attorney, Agent, or Firm* — Haynes and Boone, LLP

(57) ABSTRACT

Disclosed are methods and compositions containing functionalized nanoporous silicon particles, useful in a variety of diagnostic and/or therapeutic regimens for delivery of genetic constructs to one or more cells, tissues, and/or organs of interest. Also provided are methods for introducing into selected host cells one or more selected nucleic acid molecules. The present disclosure is also directed to a method of treating a tumor, comprising the step of administering to an individual one or more of the compositions and formulations thereof as described herein.

17 Claims, 28 Drawing Sheets

Specification includes a Sequence Listing.

(56) References Cited

OTHER PUBLICATIONS

Clamme, Jean Pierre et al., Monitoring of the Formation and Dissociation of Polyethylenimine/DNA Complexes by Two Photon Fluorescence Correlation Spectroscopy, *Biophys. J.*, 84(3):1960-1968 (Mar. 2003).
Cubillos-Ruiz, Juan et al., "Polyethylenimine-based siRNA nanocomplexes reprogram tumor-associated dendritic cells via TLR5 to elicit therapeutic antitumor immunity," *J. Clin. Invest.*, 119(8):2231-2244 (Aug. 3, 2009.
Dave, Bhuvanesh et al., "Selective Small Molecule Stat3 Inhibitor Reduces Breast Cancer Tumor-Initiating Cells and Improves Recurrence Free Survival in a Human-Xenograft Model," Aug. 2012, *PLos ONE*, 7(8):e30207, pp. 1-8 (Aug. 2012).
Davis, Mark E. et al., "Evidence of RNAi in humans from systemically administered siRNA via targeted nanoparticles," *Nature*, 464:1067-1070 (Apr. 15, 2010).
Decuzzi, P. et al., "Size and shape effects in the biodistribution of intravascularly injected particles," *J. Contr. Rel.*, 2010, 141(3):320-327 (Feb. 15, 2010).
Di Leva, Gianpiero et al., "MicroRNA cluster 221-222 and estrogen receptor alpha interactions in breast cancer," *J. Natl. Cancer Inst.*, 102(10):706-721 (Apr. 13, 2010).
Dow, Steven, "Liposome-nucleic acid immunotherapeutics," *Expert Opin. Drug Deliv.*, 5(1):11-24 (Jan. 2008).
Elbashir, Sayda M. et al., "Duplexes of 21-nucleotide RNAs mediate RNA interference in cultured mammalian cells," *Nature*, 411:494-498 (May 24, 2001).
Fang, I-Ju and Trewyn, Brian G., "Application of mesoporous silica nanoparticles in intracellular delivery of molecules and proteins," *Methods Enzymol.*, 508:41-59 (2012).
Felber, Arnaud E. et al., "pH-sensitive vesicles, polymeric micelles, and nanospheres prepared with polycarboxylates," *Adv. Drug Deliv. Rev.*, 64(11):979-992 (Aug. 2012).
Ferrari, Mauro, "Frontiers in cancer nanomedicine: directing mass transport through biological barriers," Apr. 2010, *Trends Biotechnol.*, 28(4):181-188 (Apr. 2010).
Ferrari, Mauro et al., "Nanovector Delivery of siRNA for Cancer Therapy," Cancer Gene Ther., 19(6):1-15, (Jun. 2012).
Ferrari, Mauro, "Vectoring siRNA therapeutics into the clinic," *Nat. Rev. Clin. Oncol.*, 7(9):485-486 (Sep. 2010).
Fire, Andrew et al., "Potent and specific genetic interference by double-stranded RNA in Caenorhabditis elegans," *Nature*, 391:806-811 (Feb. 19, 1998).
Fischer, Dragmar et al., "In vitro cytotoxicity testing of polycations: influence of polymer structure on cell viability and hemolysis," *Biomaterials*, 24(7):1121-1131 (Mar. 2003).
Godin, Biana et al., "Multistage nanovectors: from concept to novel imaging contrast agents and therapeutics," *Accounts Chem. Res.*, 44(10):979-989 (Oct. 18, 2011).
Gradishar, William J. et al., "Phase III trial of nanoparticle albumin-bound paclitaxel compared with polyethylated castor oil-based paclitaxel in women with breast cancer," *J. Clin. Oncol.*, 23(31):7794-7803 (Nov. 1, 2005).
Gregory, Philip A. et al., "The miR-200 family and miR-205 regulate epithelial to mesenchymal transition by targeting ZEB1 and SIP1," *Nat. Cell Biol.*, 10(5):593-601 (May 2008).
Han, Mingli et al., "Antagonism of miR-21 reverses epithelial-mesenchymal transition and cancer stem cell phenotype through AKT/ERK1/2 inactivation by targeting PTEN," *PLoS One*, 7(6):e39520, 11 pages (Jun. 2012).
Hornung, Veit et al., "Sequence-specific potent induction of IFN-α by short interfering RNA in plasmacytoid dendritic cells through TLR7," *Nat. Med.*, 11(3):263-270 (Mar. 2005).
Howard, Kenneth A. et al., "Polycation-based nanoparticle delivery for improved RNA interference therapeutics," *Exp. Opin. Biol. Ther.*, 7(12):1811-1822 (Nov. 22, 2007).

Hsu, Shu-hao et al., "Cationic lipid nanoparticles for therapeutic delivery of siRNA and miRNA to murine liver tumor," *Nanomedicine*, 9(8):1169-1180 (Nov. 13, 2013).
Hunter, AC, "Molecular hurdles in polyfectin design and mechanistic background to polycation induced cytotoxicity," *Adv. Drug Deliv. Rev.*, 58(14):1523-1531 (Sep. 28, 2006).
Iorio, MV et al., "microRNA-205 regulates HER3 in human breast cancer," *Cancer Res.*, 69(6):2195-2200 (Mar. 15, 2009).
Johnson, Steven M. et al., "RAS is regulated by the let-7 microRNA family," *Cell*, 120(5):635-647 (Mar. 11, 2005).
Jones, Sian et al., "Core signaling pathways in human pancreatic cancers revealed by global genomic analyses," *Science*, 321(5897):1801-1806 (Sep. 26, 2008).
Judge, Adam D. et al., "Confirming the RNAi-mediated mechanism of action of siRNA-based cancer therapeutics in mice," *J. Clin. Invest.*, 119(3):661-673 (Mar. 2009).
Judge, Adam D. et al., "Sequence-dependent stimulation of the mammalian innate immune response by synthetic siRNA," *Nat. Biotechnol.*, 23(4):457-462 (Apr. 2005).
Kim, Hye-Sun et al., "Functional roles of Src and Fgr in ovarian carcinoma," *Clin. Cancer Res.*, 17(7):1713-1721 (Apr. 1, 2011).
Landen, Charles N., Jr., et al., "Therapeutic EphA2 gene targeting in vivo using neutral liposomal small interfering RNA delivery," *Cancer Res.*, 65(15):6910-6918 (Aug. 1, 2005).
Lee, Jong Bum et al., "Self-assembled RNA interference microsponges for efficient siRNA delivery," *Nat. Mater.*, 11:316-322 (Feb. 26, 2012).
Lee, Ji Eun et al., "Multifunctional mesoporous silica nanocomposite nanoparticles for theranostic applications," *Accounts Chem. Res.*, 44(10):893-902 (Aug. 2011).
Li, Jiayin et al., "Leukaemia disease genes: large-scale cloning and pathway predictions," *Nat. Genet.*, 23:348-353 (Nov. 1999).
Li, S-D and Huang, L., "Gene therapy progress and prospects: non-viral gene therapy by systemic delivery," Gene Ther., 13(18):1313-1319 (Sep. 2006).
Li, Xu et al., "A mesoporous silica nanoparticle PEI fusogenic peptide system for siRNA delivery in cancer therapy," *Biomaterials*, 34(4):1391-401 (Jan. 2013).
Li, Xiaoxian et al., "Intrinsic resistance of tumorigenic breast cancer cells to chemotherapy," *J. Natl. Cancer Inst.*, 100(9):672-679 (May 7, 2008).
Lin, Jiaqi and Alexander-Katz, Alfredo, "Cell membranes open "doors" for cationic nanoparticles/biomolecules: insights into uptake kinetics," ACS Nano, 7(12):10799-10808 (Nov. 19, 2013).
MacDiarmid, Jennifer A. et al., "Sequential treatment of drug-resistant tumors with targeted minicells containing siRNA or a cytotoxic drug," *Nat. Biotechnol.*, 27(7):643-651 (Jul. 2009).
Maeda, Hiroshi, "The enhanced permeability and retention (EPR) effect in tumor vasculature: the key role of tumor-selective macromolecular drug targeting," *Adv. Enzyme Regul.*, 41:189-207 (2001).
Makley, Leah N. and Gestwicki, Jason E., "Expanding the number of 'druggable' targets: non-enzymes and protein-protein interactions," *Chem. Biol. Drug Des.*, 81(1):22-32 (Jan. 2013).
Marotta, Lauren L.C. et al., "The JAK2/STAT3 signaling pathway is required for growth of CD44+CD24-stem cell-like breast cancer cells in human tumors," *J. Clin. Invest.*, 121(7):2723-2735 (Jul. 2011).
Martello, Graziano et al., "A microRNA targeting dicer for metastasis control," *Cell*, 141(7):1195-1207 (Jun. 25, 2010).
Matsumura, Yasuhiro and Maeda, Hiroshi, "A new concept for macromolecular therapeutics in cancer chemotherapy: mechanism of tumoritropic accumulation of proteins and the antitumor agent smancs," *Cancer Res.*, 46(12 Pt 1):6387-6392 (Dec. 1986).
Merdan, Thomas et al., "Prospects for cationic polymers in gene and oligonucleotide therapy against cancer," *Adv. Drug Deliv. Rev.*, 54(5):715-758 (Sep. 2002).
Miyata, Kanjiro et al., "Rational design of smart supramolecular assemblies for gene delivery: chemical challenges in the creation of artificial viruses," *Chem. Soc. Rev.*, 41(7):2562-2574 (2012).
Moghimi, S. Moein et al., "A two-stage poly(ethylenimine)-mediated cytotoxicity: implications for gene transfer/therapy," *Mol. Ther.*, 11(6):990-995 (Jun. 2005).

(56) References Cited

OTHER PUBLICATIONS

Monteagudo, S et al., "Inhibition of p42 MAPK using a nonviral vectordelivered siRNA potentiates the antitumor effect of metformin in prostate cancer cells," Nanomedicine (Lond), 7(4):493-506 (Apr. 2012).
Na, Hee-Kyung et al., "Efficient functional delivery of siRNA using mesoporous silica nanoparticles with ultralarge pores," *Small*, 8(11):1752-1761 (Jun. 11, 2012).
Navarro, Gemma et al., "P-glycoprotein silencing with siRNA delivered by DOPE-modified PEI overcomes doxorubicin resistance in breast cancer cells," *Nanomedicine (Lond)*, 7(1):65-78 (Jan. 2012).
Nishiyama, N and Kataoka, K, "Current state, achievements, and future prospects of polymeric micelles as nanocarriers for drug and gene delivery," *Pharmacol. Therapeut.*, 112(3):630-648 (Dec. 2006).
O'Brien, ME et al., "Reduced cardiotoxicity and comparable efficacy in a phase III trial of pegylated liposomal doxorubicin HCl (CAELYX/Doxil) versus conventional doxorubicin for first-line treatment of metastatic breast cancer," *Ann. Oncol.*, 15(3):440-449 (Mar. 2004).
Ogris, M and Wagner, E, "Targeting tumors with non-viral gene delivery systems," *Drug Discov. Today*, 7(8):479-485 (Apr. 15, 2002).
Pecot, Chad V. et al., "RNA interference in the clinic: challenges and future directions," *Nat. Rev. Cancer*, 11(1):59-67 (Jan. 2011).
Petersen, Holger et al., "Polyethylenimine-graft-poly(ethylene glycol) copolymers: influence of copolymer block structure on DNA complexation and biological activities as gene delivery system," *Bioconjug. Chem.*, 13(4):845-854 (Jul.-Aug. 2002).
Ponti, Dario et al., "Isolation and in vitro propagation of tumorigenic breast cancer cells with stem/progenitor cell properties," *Cancer Res.*, 65(13):5506-5511 (Jul. 1, 2005).
Qased, Abu Baker et al., "MicroRNA-18a upregulates autophagy and ataxia telangiectasia mutated gene expression in HCT116 colon cancer cells," *Mal. Med. Report*, 7(2):559-564 (Feb. 2013).
Radu, Daniela R. et al., "A polyamidoamine dendrimer-capped mesoporous silica nanosphere-based gene transfection reagent," *J. Am. Chem. Soc.*, 126(41):13216-13217 (Sep. 25, 2004).
Russ, Verena et al., "Oligoethylenimine-grafted polypropylenimine dendrimers as degradable and biocompatible synthetic vectors for gene delivery," *J. Control Release*, 132(2):131-140 (Dec. 8, 2008).
Ryu, Seongho et al., "Suppression of miRNA-708 by polycomb group promotes metastases by calcium-induced cell migration," *Cancer Cell*, 23(1):63-76 (Jan. 14, 2013).
Sampson, Valerie B. et al., "MicroRNA let-7a down-regulates MYC and reverts MYC induced growth in Burkitt lymphoma cells," *Cancer Res.*, 67(20):9762-9770 (Oct. 15, 2007).
Santel, A et al., "A novel siRNA-lipoplex technology for RNA interference in the mouse vascular endothelium," *Gene Ther.*, 13:1222-1234 (Apr. 2006).
Schlabach, Michael R. et al., "Cancer proliferation gene discovery through functional genomics," *Science*, 319(5863):620-624 (Feb. 1, 2008).
Semple, Sean C. et al., "Rational design of cationic lipids for siRNA delivery," *Nat. Biotechnol.*, 28(2):172-176 (Feb. 2010).
Shahzad, Mian M. et al., "Dual targeting of EphA2 and FAK in ovarian carcinoma," *Cancer Biol. Ther.*, 8(11):1027-1034 (Jun. 2009).
Shen, Jianliang et al., "Cyclodextrin and polyethylenimine functionalized mesoporous silica nanoparticles for delivery of siRNA cancer therapeutics," *Theranostics*, 4(5):487-497 (Feb. 2014).
Shen, Jingshi et al., "ER stress regulation of ATF6 localization by dissociation of BiP/GRP78 binding and unmasking of Golgi localization signals," *Dev. Cell*, 3(1):99-111 (Jul. 2002).
Shen, Jianliang et al., "High capacity nanoporous silicon carrier for systemic delivery of gene silencing therapeutics," *ACS Nano*, 7(11):9867-9880 (Oct. 2013).
Shen, Haifa et al., "Cooperative, nanoparticle-enabled thermal therapy of breast cancer." *Adv. Healthcare Mater*, 1(1):84-89 (Jan. 11, 2012).
Shen, Haifa et al., "Delivery of gene silencing agents for breast cancer therapy," *Breast Cancer Res.*, 15(3):205 (May 2013).
Sonawane, N. D. et al., "Chloride accumulation and swelling in endosomes enhances DNA transfer by polyamine-DNA polyplexes," *J. Blot. Chem.*, 278(45):44826-44831 (Nov. 7, 2003).
Suzuki, Takeshi et al., "New genes involved in cancer identified by retroviral tagging," *Nat. Genet.*, 32:166-174 (Aug. 2002).
Tanaka, T et al., "Sustained small interfering RNA delivery by mesoporous silicon particles," *Cancer Res.*, 70(9):3687-3696 (May 1, 2010).
Tasciotti, Ennio et al., "Mesoporous silicon particles as a multistage delivery system for imaging and therapeutic applications," *Nat. Nanotechnol.*, 3(3):151-7 (Mar. 2008).
Tateda, Kazuhiro et al., "Lipopolysaccharide-induced lethality and cytokine production in aged mice," *Infect. Immun.*, 64(3):769-774 (Mar. 1996).
Thomas, Mini and Klibanov, Alexander M., "Conjugation to gold nanoparticles enhances polyethylenimine's transfer of plasmid DNA into mammalian cells," *Proc. Natl. Acad. Sci. USA*, 100(16):9138-9143 (Aug. 5, 2003).
Unsal-Kacmaz, Keziban et al., "The interaction of PKN3 with RhoC promotes malignant growth," *Mol. Oncol.*, 6(3):284-298 (Jun. 2012).
Van De Ven, Anne L. et al., "Rapid tumoritropic accumulation of systemically injected plateloid particles and their biodistribution," *J. Contr. Rel.*, 158(1):148-155 (Feb. 28, 2012).
Vivero-Escoto, Juan L. et al., "Mesoporous silica nanoparticles for intracellular controlled drug delivery," *Small*, 6(18):1952-1967 (Sep. 20, 2010).
Wood, Laura D. et al., "The genomic landscapes of human breast and colorectal cancers," *Science*, 318(5853):1108-1113 (Oct. 11, 2007).
Xia, Tian et al., "Polyethyleneimine coating enhances the cellular uptake of mesoporous silica nanoparticles and allows safe delivery of siRNA and DNA constructs," *ACS Nano*, 3(10):3273-3286 (Oct. 27, 2009).
Xu, Rong et al., "Multistage vectored siRNA targeting ataxia-telangiectasia mutated for breast cancer therapy," *Small*, 9(9-10):1799-1808 (May 27, 2013).
Yao, Yan-dan et al., "Targeted delivery of PLK1-siRNA by ScFv suppresses Her2+ breast cancer growth and metastasis," *Sci. Transl. Med.*, 4(130):130ra148, 12 pages (Apr. 18, 2012).
Yu, Fengyan et al., "let-7 regulates self-renewal and tumorigenicity of breast cancer cells," *Cell*, 131(6):1109-1123 (Dec. 14, 2007).
Yu, Z et al., "microRNA 17/20 inhibits cellular invasion and tumor metastasis in breast cancer by heterotypic signaling," *Proc. Natl. Acad. Sci. USA*, 107(18):8231-8236 (May 4, 2010).
Zhang, M and Kataoka, K, "Nano-structured composites based on calcium phosphate for cellular delivery of therapeutic and diagnostic agents," *Nano. Today*, 4(6):508e17 (2009).
Zhang, Mingzhen et al., "Polycation-functionalized nanoporous silicon particles for gene silencing on breast cancer cells," Biomaterials, 35(1):423-431 (Jan. 2014).
Zimmermann, Tracy S. et al., "RNAi-mediated gene silencing in non-human primates," *Nature*, 441:111-114 (May 4, 2006).
Zuckerman, JE et al., "Polycation-siRNA nanoparticles can disassemble at the kidney glomerular basement membrane," *Proc. Natl. Acad. Sci. USA*, 109(8):3137-3142 (Feb. 21, 2012).
International Searching Authority (Korea), International Search Report, Authorized Officer: Young Sihn Sihn, for Application No. PCT/US2014/042166, dated Oct. 22, 2014, 4 pages, Republic of Korea.
International Searching Authority (Korea), Written Opinion, Authorized Officer: Young Sihn Sihn, for Application No. PCT/US2014/042166, dated Oct. 22, 2014, 8 pages, Republic of Korea.

* cited by examiner

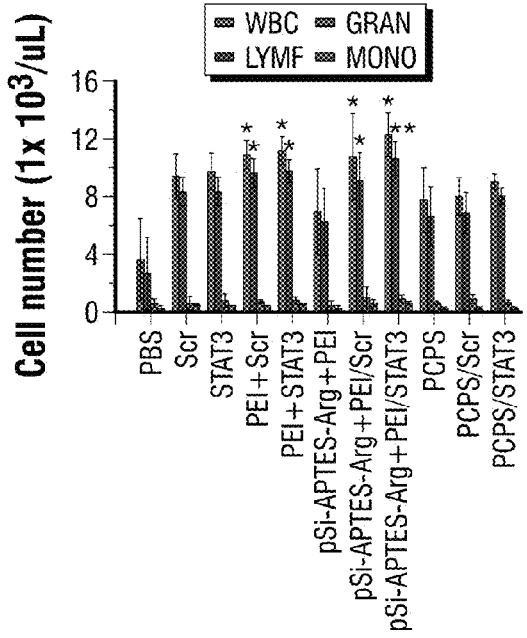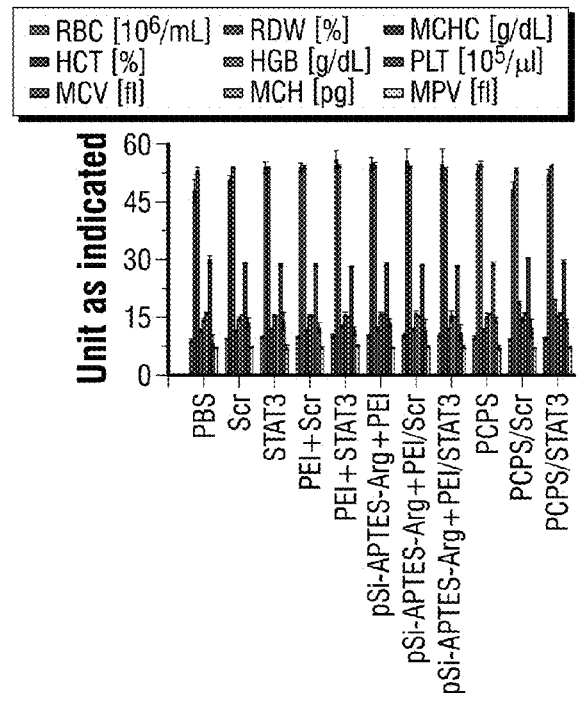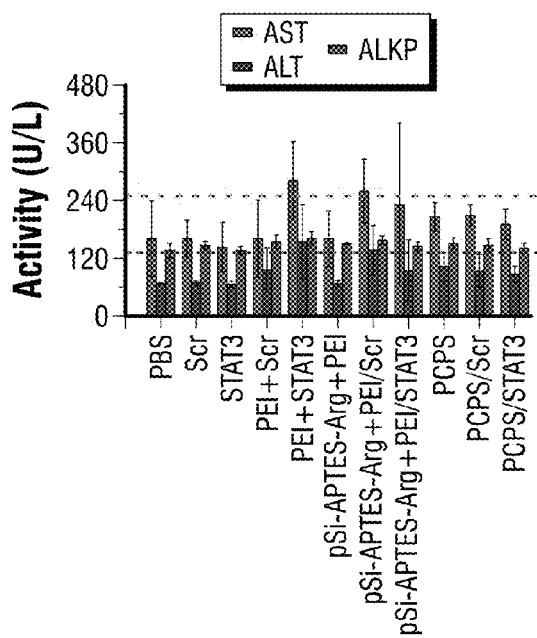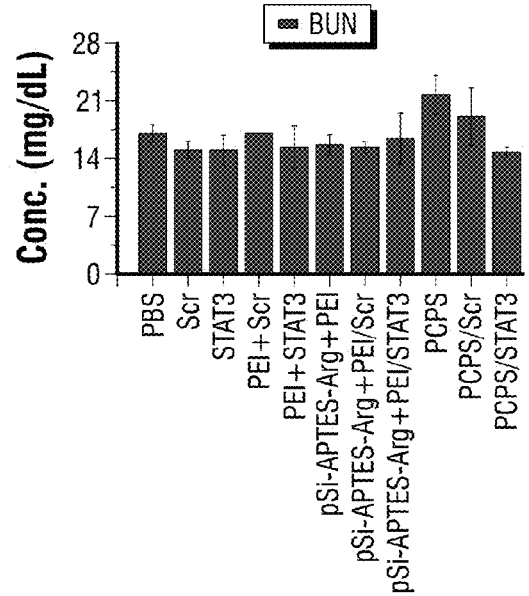
FIG. 9A-1
FIG. 9A-2
FIG. 9B-1
FIG. 9B-2

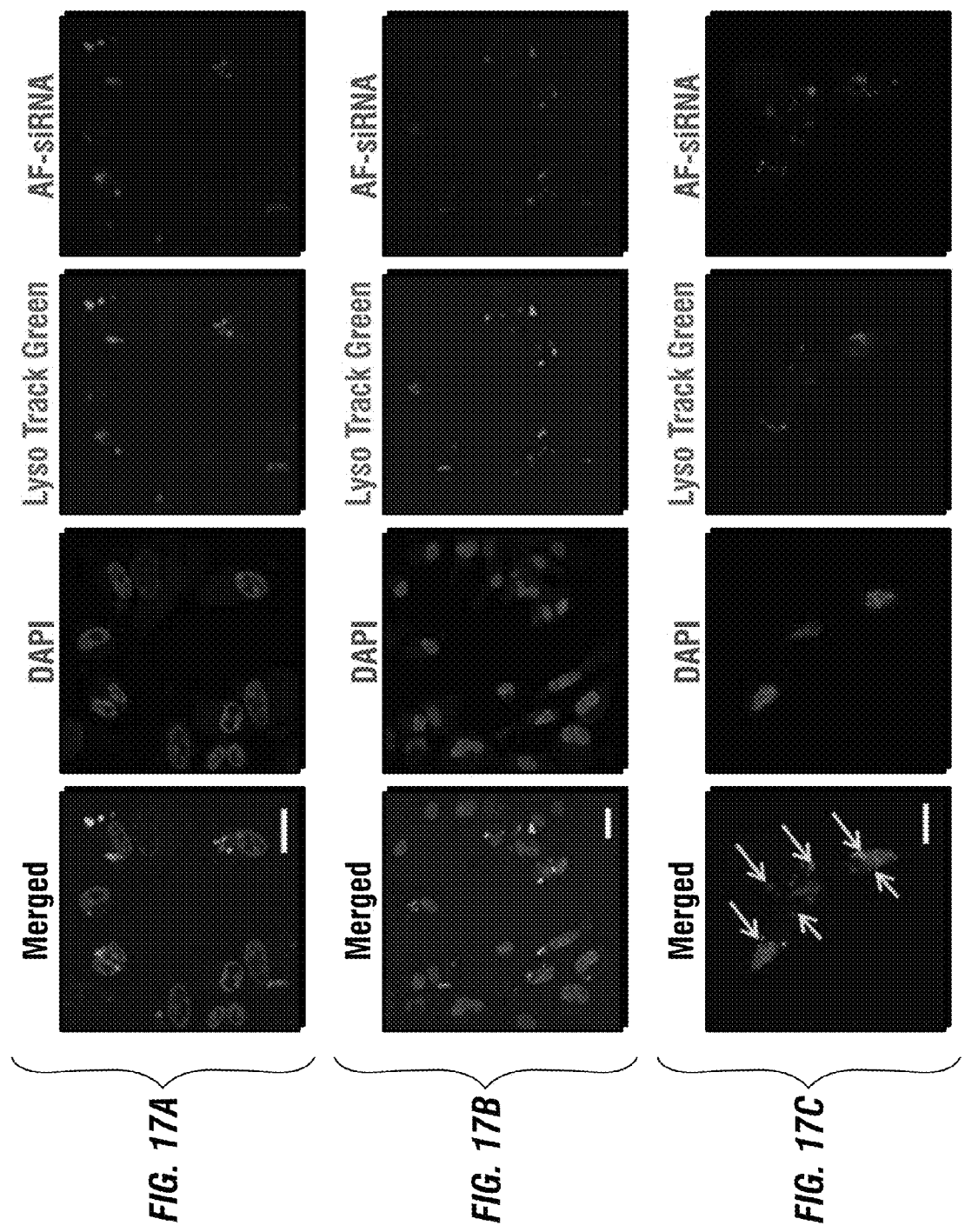

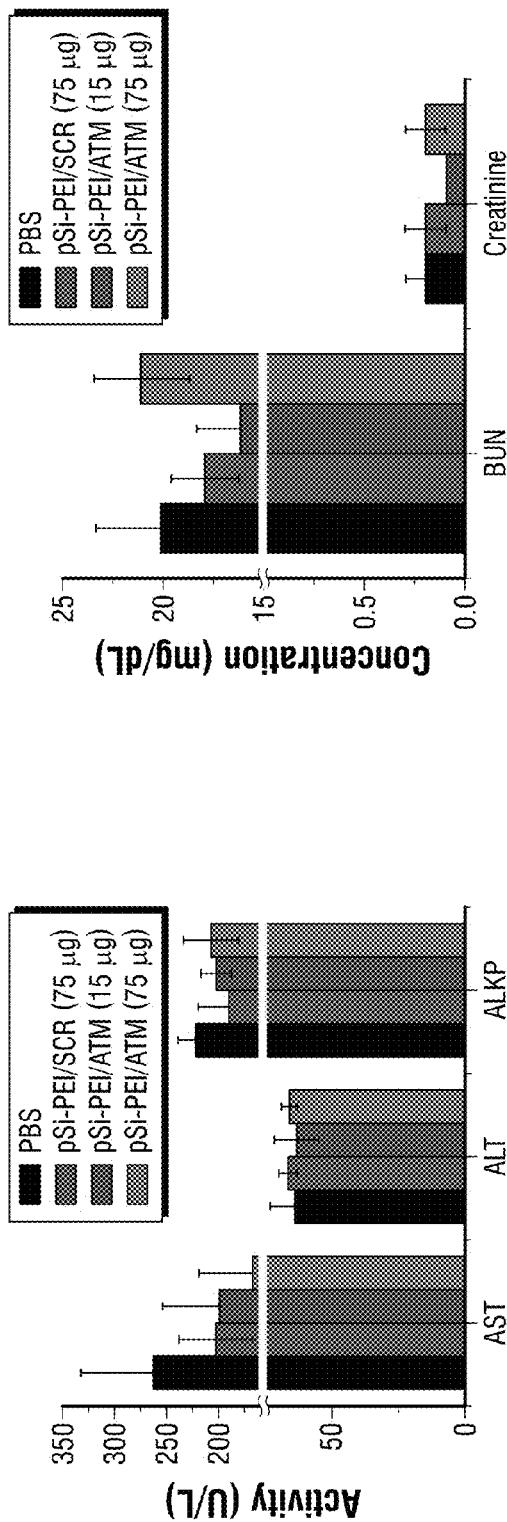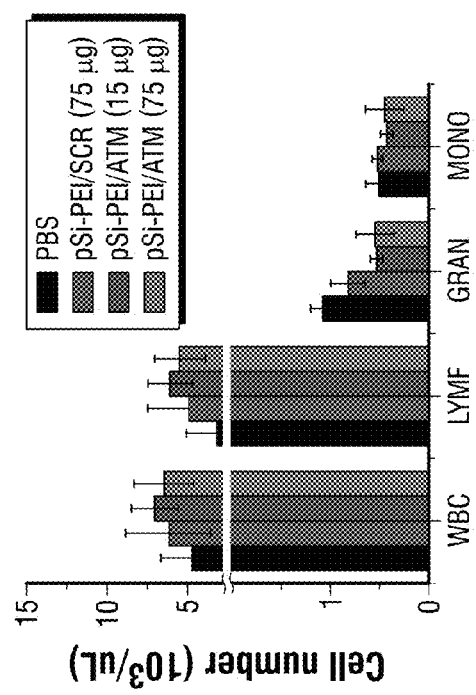
FIG. 21A  FIG. 21B  FIG. 21C

SEQUENCE LISTING

<160> NUMBER OF SEQ ID NOS: 8

<210> SEQ ID NO 1
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 1
cagcagcttg acacggta                                                    18

<210> SEQ ID NO 2
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 2
aaacaccaaa gtggcatgtg a                                                21

<210> SEQ ID NO 3
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 3
cacagtggtg cctaccaaga                                                  20

<210> SEQ ID NO 4
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 4
tgtcttttgt cagggtctt t                                                 21

<210> SEQ ID NO 5
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 5
ttcaaaggat tcatggtcca g                                                21

<210> SEQ ID NO 6
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 6
gctgtgagaa aaccatggaa                                                  20

<210> SEQ ID NO 7
<211> LENGTH: 19
<212> TYPE: DNA
<213> ORGANISM: Artificial Sequence

```
<220> FEATURE:
<223> OTHER INFORMATION: synthetic oligonucleotide

<400> SEQUENCE: 7
aaatcgtgcg tgacattaa                                                    19

<210> SEQ ID NO 8
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 8
ctcgtcatac tcctgcttg                                                    19
```

POLYCATION-FUNCTIONALIZED NANOPOROUS SILICON CARRIER FOR SYSTEMIC DELIVERY OF GENE SILENCING AGENTS

CROSS-REFERENCE TO RELATED APPLICATIONS

The present application claims priority to PCT Intl. Pat. Appl. No. PCT/US2014/42166; filed Jun. 12, 2014, which claims the benefit of U.S. Prov. Pat. Appl. No. 61/834,123, filed Jun. 12, 2013, the contents of each of which is specifically incorporated herein in its entirety by express reference thereto.

STATEMENT REGARDING FEDERALLY SPONSORED RESEARCH OR DEVELOPMENT

This invention was made with government support under contracts W81XWE-09-1-0212 and W81XWH-12-1-0414 awarded by the Department of Defense and contracts U54CA151668 and U54CA151668 awarded by the National Institutes of Health. The government has certain rights in the invention.

NAMES OF THE PARTIES TO A JOINT RESEARCH AGREEMENT

Not Applicable.

BACKGROUND OF THE INVENTION

Field of the Invention

The invention relates to the fields of nanomedicine and pharmacology. In particular, the present disclosure provides novel, non-obvious, and useful functionalized nanoporous silicon particles (and compositions containing them), for delivery of genetic constructs to one or more cells, tissues, and/or organs of interest. Also provided are methods for introducing one or more selected nucleic acid molecules into target host cells, which are useful in a variety of diagnostic and/or therapeutic regimens.

Description of Related Art

To produce a therapeutic effect in an animal, an active agent must be made available at its desired site of action within the body in therapeutically-effective amounts. Delivery of certain active agents to particular sites within the body continues to pose a significant challenge in human and veterinary medicine. The bioavailability of an active agent may be affected by numerous factors, including, for example, the quantity of active agent administered, the extent and rate of its absorption from its administration site, its distribution or localization within one or more tissues, its biotransformation, its binding to one or more cell types, its functional half-life, and even its elimination and excretion from the body. A major challenge to the delivery of active agents is the numerous biological barriers within the body that must be traversed, including, for example the organs of the reticulo-endothelial system (RES), plasma protein binding, blood vessel wall, high interstitial pressure, and such like.

To overcome these biological barriers, and to reach desired plasma drug concentrations, patients are usually administered a much higher concentration of the active agent, which can often lead to therapy-related, or therapy-induced toxicity. A related factor accompanying unfavorable accumulation of the active agent at its desired target site is the development of acquired resistance.

Accordingly, there remains a need in the medical arts for compositions and methods of delivering such compositions, which circumvent drug-resistance mechanisms, which increase the therapeutic range of one or more active agent(s) without producing unwanted toxic side effects.

Deficiencies in the Prior Art

Application of nanomedicine to fight drug-resistance has been explored by multiple laboratories. However, much remains to be done. Considering these challenges to cancer therapy, there exists a need in the art for a robust and safe drug delivery system with the ability to target and enrich its payload concentration at one or more sites within the body, such as a tumor site, or within a population of cancerous cells that would enhance the eradication of targeted cells, reduce chances of the target cell acquiring resistance, and overcome one or more drug-resistance mechanism(s), which could limit the effectiveness of the chosen therapy.

BRIEF SUMMARY OF THE INVENTION

The present invention addresses these and other unmet deficiencies inherent in the relevant oncological and pharmaceutical arts, by providing novel and non-obvious drug delivery vehicles (as well as compositions and pharmaceutical formulations comprising them) that are useful in delivering one or more therapeutic and/or diagnostic agents to one or more selected cell types within or about the body of a mammal, and in a human, in particular.

In certain embodiments, compositions are provided for delivering one or more anti-cancer compounds, including one or more chemotherapeutic and/or cytotoxic agents to one or more cells of a mammalian (and preferably, a human) tumor, or to a population of cancer cells within or about the body of the mammal.

The present disclosure also provides a method of treating or ameliorating one or more symptoms of cancer, tumor formation, or hyper-proliferative disorder in a mammal in need thereof. Such a method generally includes the step of providing or administering to the mammal, either systemically, or locally at one or more regions or sites within, or about the body of the animal an effective amount of at least a first drug delivery agent disclosed herein that comprises at least a first therapeutic agent, for a time sufficient to treat the cancer in the animal, or to ameliorate one or more symptoms thereof.

In a further aspect, the present disclosure provides a method for silencing a gene expressed in one or more cells of a mammal in need thereof. This method, in an overall and general sense includes providing to one or more cells or to one or more tissues of the body of the mammal, an amount of one or more of the drug delivery vehicles disclosed herein that comprises an effective amount of a first siRNA or microRNA that is specific for a gene that is expressed by a tumor cell, in an amount and for a time effective to knockdown or inhibit the expression of one or more genes in the one or more cells. In certain applications, the silencing agents are interfering RNAs (RNAi's) that inhibit the expression of one or more deleterious genes expressed in a human cancer cell or a tumor that comprises such cancerous cells.

As set forth in more detail below, the methods and compositions of the present disclosure have numerous variations. More specific and non-limiting embodiments of the present disclosure will now be described in more detail.

Therapeutic Agents

Exemplary therapeutic agents, which may be administered to a subject in need thereof, by incorporation of the agent(s) within one or more populations of the polycation-functionalized nanoporous silicon particles described herein, include, without limitation, one or more anti-cancer drugs, including the conventional drugs such as camptothecin, docetaxel, temozolomide, carmustine, paclitaxel, gemcitabine, and anthracyclines, including, but not limited to, doxorubicin, liposomal doxorubicin, daunorubicin, and the like, or one or more combinations thereof. The polycation-functionalized nanoporous silicon particles may preferably be configured into a shape selected from the group consisting of discoidal, spheroid, non-spheroid, oblate spheroid, and combinations thereof. Preferably, the porous particle is fabricated of a porous or mesoporous silicon material that is discoidal in shape.

An active agent's ability to reach an intended target at a desired concentration is usually affected by a multiplicity of biological barriers. The biological barrier may be, for example, an epithelial or endothelial barrier, such as the blood-brain barrier, that is based on tight junctions that prevent or limit para-cellular transport of an active agent. Cells of the reticulo-endothelial system may also act as a biological barrier against an active agent. The biological barrier may also be represented by a cell membrane or a nuclear membrane of a target cell.

In some embodiments, the polycation-functionalized nanoporous silicon particles herein are able to overcome at least one biological barrier, including one or more biological barriers selected from the group consisting of a hemo-rheology barrier, a reticulo-endothelial barrier, a blood-brain barrier, a tumor-associated osmotic interstitial pressure barrier, an ionic- or a molecular-pump barrier, a cell-membrane barrier, an enzymatic-degradation barrier, a nuclear membrane barrier, and combinations thereof. In a related embodiment, the porous particle may have at least one targeting moiety on its surface specifically directed against a target cell. In some embodiments, the at least one targeting moiety is selected from the group consisting of ligands, antibodies, antibody fragments, peptides, aptamers, small molecules, and combinations thereof. For example, ligands can be chemically linked to appropriate reactive groups on the surface of the particle. Protein ligands can be linked to amino- and thiol-reactive groups under conditions effective to form thioether or amide bonds respectively. Methods of attaching antibody or other polymer-binding agents to an inorganic or polymeric support are detailed elsewhere (see, e.g., Taylor, 1991).

Any active agent, a small molecule drug or a biomolecular drug, may be delivered using the composition of the present disclosure. In some embodiments, the at least one active agent is a biologically active compound selected from the group consisting of peptides, proteins, therapeutic agents, diagnostic agents, non-biological materials, and combinations thereof. The therapeutic agent may be any physiologically or pharmacologically active substance that can produce a desired biological effect. The therapeutic agent may be a chemotherapeutic agent, an immunosuppressive agent, a cytokine, a cytotoxic agent, a nucleolytic compound, an anti-inflammatory compound, or a pro-drug enzyme, which may be naturally occurring, or produced by synthetic or recombinant methods, or by a combination thereof.

Drugs that are affected by classical multi-drug resistance, such as the vinca alkaloids (e.g., vinblastine, vincristine), the anthracyclines (e.g., doxorubicin and daunorubicin), RNA transcription inhibitors (e.g., actinomycin-D), and microtubule stabilizing drugs (e.g., paclitaxel) can have particular utility as the therapeutic agent. In some embodiments, the therapeutic agent may be a hydrophobic drug or a hydrophilic drug. Cytokines may be also used as the therapeutic agent. Examples of such cytokines are lymphokines, monokines, and traditional polypeptide hormones. A cancer chemotherapy agent may be a preferred therapeutic agent. For a more detailed description of anticancer agents and other therapeutic agents, those skilled in the art are referred to any number of instructive manuals including, but not limited to, the *Physician's Desk Reference* and to the reference by Goodman and Gilman (2001).

In some embodiments, the therapeutic agent may be selected from the group consisting of genes, nucleic acids, shRNAs, siRNAs, microRNAs, DNA fragments, RNA fragments, plasmids, and combinations thereof. In an illustrative embodiment, the therapeutic agent is a siRNA or a microRNA that silences one or more genes expressed by the cancer cells or the tumor. The therapeutic agent can also be applied to engineer the genome of cancer cells and/or stromal cells in the tumor, such as a CRISPR/Cas9 system.

The composition of the disclosure may be designed, formulated and processed so as to be suitable for a variety of therapeutic and diagnostic uses and modes of administration.

The composition of the disclosure may be administered to a subject, such as a human, via any suitable administration method in order to treat, prevent, and/or monitor a physiological condition, such as a disease. Embodiments of the composition may be particularly useful for oncological applications, i.e., for treatment and/or monitoring cancer or a condition, such as tumor associated with cancer. Preferably, however, it is adapted for parenteral administration. As used herein, parenteral administration includes any invasive route of administration, such as intravenous, subdermal, intradermal, subcutaneous, intramuscular, locoregional, intratumoral, intraperitoneal, interstitial, and intralesional. Preferred routes of administration of the compositions of the present disclosure may include, without limitation, intravenous, subcutaneous, and intraperitoneal. The compositions of the present disclosure and their suspension for injection can be adapted for parenteral administration, which means that they can be formulated and processed to meet the requirements of parenteral dosage forms. Such requirements are outlined in the major pharmacopoeias.

Chemotherapeutic Compounds and Pharmaceutical Formulations

The polycation-functionalized nanoporous silicon carriers of the present disclosure may be employed as a single cancer treatment modality, or alternatively may be combined with one or more additional therapeutic, diagnostic, and/or prophylactic agents, including, without limitation, one or more proteins, peptides, polypeptides (including, without limitation, enzymes, antibodies, antigens, antigen binding fragments etc.); RNA molecules (including, without limitation, siRNAs, microRNAs, iRNAs, mRNAs, tRNAs, or catalytic RNAs, such as ribozymes, and the like), DNA molecules (including, without limitation, oligonucleotides, polynucleotides, genes, coding sequences (CDS), introns, exons, plasmids, cosmids, phagemids, baculovirus, vectors [including, without limitation, viral vectors, virions, viral particles and such like]); peptide nucleic acids, detection agents, imaging agents, contrast agents, detectable gas, radionuclides, or such like, and one or more additional chemotherapeutic agents, surgical intervention (e.g., tumor resection), radiotherapy, and the like, or any combination thereof as part of a multifactorial, or multifocal treatment plan for the affected patient.

The polycation-functionalized nanoporous silicon carriers of the present disclosure may also further optionally include one or more additional active ingredients, including, without limitation, one or more anti-cancer agents, one or more anti-tumorigenic agents, one or more antineoplastic or cytotoxic agents, one or more transcription factors, immunomodulating agents, immuno stimulating agents, neuroactive agents, anti-inflammatory agents, chemotherapeutic agents, hormones, so called "trophic factors," cytokines, chemokines, receptor agonists or antagonists, or such like, or any combination thereof.

The polycation-functionalized nanoporous silicon formulations of the present disclosure may also further optionally include one or more additional components to aid, facilitate, or improve delivery of a pro-drug and/or an active metabolite contained therein, including, without limitation, one or more liposomes, lipid particles, lipid complexes, and may further optionally include one or more binding agents, cell surface active agents, surfactants, lipid complexes, niosomes, ethosomes, transferosomes, phospholipids, sphingolipids, sphingosomes, or any combination thereof, and may optionally be provided within a pharmaceutical formulation that includes one or more additional nanoparticles, microparticles, nanocapsules, microcapsules, nano spheres, microspheres, or any combination thereof.

Preferably, the polycation-functionalized nanoporous silicon carriers of the present disclosure will generally be formulated for systemic and/or localized administration to an animal, or to one or more cells or tissues thereof, and in particular, will be formulated for systemic and/or localized administration to a mammal, or to one or more cancerous cells, tumor tissues, or affected organs thereof. In certain embodiments, the compounds and methods disclosed herein will find particular use in the systemic and/or localized administration of one or more antineoplastic agents to one or more cells or tissues of a human being.

Preferably, drug-delivery formulations of the active compounds disclosed herein will be at least substantially stable at a pH from about 4.2 to about 8.2, and more preferably, will be substantially stable at a pH of from about 5 to about 7.5. Preferably, the active ingredient(s) and targeted drugs will be substantially active at physiological conditions of the animal into which they are being administered.

The present disclosure also provides for the use of one or more of the disclosed polycation-functionalized nanoporous silicon carriers in the manufacture of a medicament for therapy and/or for the amelioration of one or more symptoms of a disease, disorder, dysfunction, or condition, and particularly for use in the manufacture of a medicament for treating, one or more diseases, dysfunctions, or disorders such as cancers, carcinomas, and/or solid tumors in a mammal, and, in a human, in particular.

The present disclosure also provides for the use of one or more of the disclosed polycation-functionalized nanoporous silicon drug delivery systems in the manufacture of a medicament for the treatment of cancer, and in particular, those cancers that can be affected by the silencing of one or more expressed gene using small interfering RNA, or microRNA to facilitate knock-down or inhibition of the expressed gene. In certain embodiments, the invention also includes diagnostic and/or targeting compounds that may be optionally included in or on the surface of the silicon nanoparticle carriers to facilitate improvements in the treatment or prognosis of a mammalian cancer, and a human breast tumor in particular.

Chemotherapeutic Methods

Another important aspect of this disclosure concerns methods for using the polycation-functionalized nanoporous silicon carriers to facilitate treatment or the amelioration of one or more symptoms of the disease in a mammal having, suspected of having, or at risk for developing such a condition, and in particular for those mammalian diagnosed with one or more cancers. Such methods generally involve administering to a mammal (and in particular, to a human in need thereof), one or more of the disclosed polycation-functionalized nanoporous silicon carriers formulated to contain one or more anticancer compounds, in an amount and for a time sufficient to treat (or, alternatively, to ameliorate one or more symptoms of) a cancer in a mammal to which the composition has been administered.

In certain embodiments, the therapeutic formulations described herein may be provided to the animal as a single treatment modality, as a single administration, or alternatively provided to the patient in multiple administrations over a period of from several hours to several days, from several days to several weeks, or even over a period of several weeks to several months or longer, as needed to treat the cancer. In some aspects, it may be desirable to continue the treatment throughout the lifetime of the patient. In other embodiments, it may be desirable to provide the therapy in combination with one or more existing, or conventional, treatment regimens, including surgery, radiotherapy, brachytherapy, chemotherapy, and combinations thereof.

Chemotherapeutic Kits

Therapeutic kits that include one or more of the disclosed chemotherapeutic drug delivery compositions (and instructions for using the kit) also represent an important aspect of the present disclosure. Such kits may further optionally include one or more diagnostic agents, one or more therapeutic agents, or any combination thereof, either alone or further in combination with one or more additional compounds, pharmaceuticals, or such like.

The chemotherapeutic kits of the present disclosure may be packaged for commercial distribution, and may further optionally include one or more delivery devices adapted to deliver the polycation-functionalized nanoporous silicon carrier-based chemotherapeutic composition(s) to an animal (e.g., syringes, injectables, and the like). Such kits typically include at least one vial, test tube, flask, bottle, syringe or other container, into which the polycation-functionalized nanoporous silicon carrier-based chemotherapeutic composition(s) may be placed, and preferably suitably aliquotted. Where a second pharmaceutical compound is also provided, the kit may also contain a second distinct container into which this second composition may be placed. Alternatively, a plurality of polycation-functionalized nanoporous silicon carrier-based compositions as disclosed herein may be prepared in a single mixture, including those prepared as a suspension or in solution, and may be packaged in a single container, such as a vial, flask, syringe, catheter, cannula, bottle, or other suitable containment.

The chemotherapeutic kits of the present disclosure may also typically include a retention mechanism adapted to contain or retain the vial(s) or other container(s) in close confinement for commercial sale, such as, e.g., injection or blow-molded plastic containers into which the desired vial(s) or other container(s) may be retained to minimize or Preparation of Medicaments Another important aspect of the present disclosure concerns methods for using the disclosed polycation-functionalized nanoporous silicon carriers as agents for delivering therapeutic or diagnostic compounds to selected cells or tissues of a vertebrate mammal, and particularly one that has been diagnosed with one or more types of hyperproliferative diseases, such as cancer. Such use generally involves administration to an animal in need thereof one or more of the disclosed therapeutic delivery vehicles, in an amount and for a time sufficient to prevent, treat, lessen, or cure the disease, disorder, dysfunction, condition, or deficiency in the affected animal, and/or to ameliorate one or more symptoms thereof.

Pharmaceutical Formulations

In certain embodiments, the present disclosure provides one or more chemotherapeutic and/or diagnostic compounds in a pharmaceutically-acceptable formulation of the disclosed polycation-functionalized nanoporous silicon carriers for delivering these compounds of interest to one or more cells or tissues of an animal, in need thereof. Such delivery may include the polycation-functionalized nanoporous silicon carrier-based chemotherapeutics alone, or in combination with one or more other modalities of diagnosis, prophylaxis and/or therapy, as may be deemed necessary for treatment of the particular subject. The formulation of pharmaceutically-acceptable excipients and carrier solutions is well known to those of ordinary skill in the art, as is the development of suitable dosing and treatment regimens for using the particular compositions described herein in a variety of treatment regimens.

In certain circumstances it will be desirable to deliver the polycation-functionalized nanoporous silicon carrier-based-chemotherapeutic compositions disclosed herein in one or more suitably-formulated pharmaceutical vehicles, using one or more delivery devices, including, without limitation, by one or more conventional administration methods, including, but not limited to, subcutaneously, parenterally, intravenously, intramuscularly, intrathecally, orally, intraperitoneally, transdermally, topically, by oral or nasal inhalation, or by direct injection to one or more cells, tissues, or organs within or about the body of an animal.

The methods of administration may also include those modalities as described in U.S. Pat. Nos. 5,543,158; 5,641,515; and 5,399,363 (each of which is specifically incorporated herein in its entirety by express reference thereto). Solutions of the active compounds as freebase or pharmacologically acceptable salts may be prepared in sterile water, and may be suitably mixed with one or more surfactants, such as hydroxypropylcellulose. Dispersions may also be prepared in glycerol, liquid polyethylene glycols, oils, or mixtures thereof. Under ordinary conditions of storage and use, these preparations contain a preservative to prevent the growth of microorganisms.

For administration of an injectable aqueous solution, without limitation, the solution may be suitably buffered, if necessary, and the liquid diluent first rendered isotonic with sufficient saline or glucose. These particular aqueous solutions are especially suitable for intravenous, intramuscular, subcutaneous, transdermal, subdermal, and/or intraperitoneal administration. In this regard, the compositions disclosed herein may be formulated in one or more pharmaceutically acceptable vehicles, including for example sterile aqueous media, buffers, diluents, etc. For example, a given dosage of active ingredient(s) may be dissolved in a particular volume of an isotonic solution (e.g., an isotonic NaCl-based solution), and then injected at the proposed site of administration, or further diluted in a vehicle suitable for intravenous infusion (see, e.g., "*Remington's Pharmaceutical Sciences*" 15$^{th}$ Edition, pp. 1035-1038 and 1570-1580). While some variation in dosage will necessarily occur depending on the condition of the subject being treated, the extent of the treatment, and the site of administration, the person responsible for administration will nevertheless be able to determine the correct dosing regimens appropriate for the individual subject using ordinary knowledge in the medical and pharmaceutical arts.

Sterile injectable compositions may be prepared by incorporating the disclosed polycation-functionalized nanoporous silicon carrier-based drug delivery systems in the required amount in the appropriate solvent with several of the other ingredients enumerated above, as required, followed by filtered sterilization. Generally, dispersions can be prepared by incorporating the selected sterilized active ingredient(s) into a sterile vehicle that contains the basic dispersion medium and the required other ingredients from those enumerated above. The compositions disclosed herein may also be formulated in a neutral or salt form. Pharmaceutically-acceptable salts include the acid addition salts (formed with the free amino groups of the protein), and which are formed with inorganic acids such as, without limitation, hydrochloric or phosphoric acids, or organic acids such as, without limitation, acetic, oxalic, tartaric, mandelic, and the like. Salts formed with the free carboxyl groups can also be derived from inorganic bases such as, without limitation, sodium, potassium, ammonium, calcium, or ferric hydroxides, and such organic bases as isopropylamine, trimethylamine, histidine, procaine, and the like. Upon formulation, solutions will be administered in a manner compatible with the dosage formulation, and in such amount as is effective for the intended application. The formulations are readily administered in a variety of dosage forms such as injectable solutions, topical preparations, oral formulations, including sustain-release capsules, hydrogels, colloids, viscous gels, transdermal reagents, intranasal and inhalation formulations, and the like.

The amount, dosage regimen, formulation, and administration of chemotherapeutics comprised within a population of one or more of the polycation-functionalized nanoporous silicon carriers disclosed herein will be within the purview of the ordinarily-skilled artisan having benefit of the present teaching. It is contemplated, however, in an overall and general sense that administration of therapeutically-effective (i.e., pharmaceutically-effective) amounts of the disclosed chemotherapeutic compositions may be achieved by one or more administrations ("doses"), such as, without limitation, a single injection of a sufficient quantity of the polycation-functionalized nanoporous silicon carrier-based drug delivery systems comprising one or more active agents to provide the desired benefit to the patient or the test subject undergoing such a procedure. Alternatively, in some circumstances, it may be desirable to provide multiple, or successive administrations of the compositions, either over a relatively short, or even a relatively prolonged period, as may be determined by the medical practitioner overseeing the administration of such compositions to the selected individual.

Typically, formulations of one or more of the drug delivery nanoparticles described herein will contain at least a chemotherapeutically-effective amount of a first active agent Preferably, the formulation may contain at least about 0.001% of each active ingredient, preferably at least about 0.01% of the active ingredient, although the percentage of the active ingredient(s) may, of course, be varied, and may conveniently be present in amounts from about 0.01 to about 90 weight % or volume %, or from about 0.1 to about 80 weight % or volume %, or more preferably, from about 0.2 to about 60 weight % or volume %, based upon the total formulation. Naturally, the amount of active compound(s) in each composition may be prepared in such a way that a suitable dosage will be obtained in any given unit dose of the compound. Factors such as solubility, bioavailability, biological $t_{1/2}$, route of administration, product shelf-life, as well as other pharmacological considerations will be contemplated by one of ordinary skill in the art of preparing such pharmaceutical formulations, and as such, a variety of dosages and treatment regimens may be desirable.

Pharmaceutical formulations adapted for injectable administration include, but are not limited to, sterile aqueous solutions, dispersions, and sterile powders for the extemporaneous preparation of sterile injectable solutions or dispersions including, without limitation, one or more of those described in U.S. Pat. No. 5,466,468 (specifically incorporated herein in its entirety by express reference thereto). In all cases, the form is preferably sterile, and is preferably fluid to the extent that easy syringability and/or ready administration to the patient is achievable. It is also preferably at least sufficiently stable under the conditions of manufacture and storage, and must be preserved against the contaminating action of microorganisms, such as viruses, bacteria, fungi, and such like.

The carrier(s) can be a solvent or dispersion medium including, without limitation, water, ethanol, polyol (e.g., glycerol, propylene glycol, and liquid polyethylene glycol, and the like, or a combination thereof), one or more vegetable oils, or any combination thereof, although additional pharmaceutically-acceptable components may be included.

Proper fluidity of the pharmaceutical formulations disclosed herein may be maintained, for example, by the use of a coating, such as, e.g., a lecithin, by the maintenance of the required particle size in the case of dispersion, by the use of a surfactant, or any combination of these techniques. The inhibition or prevention of the action of microorganisms can be brought about by one or more antibacterial or antifungal agents, for example, without limitation, a paraben, chlorobutanol, phenol, sorbic acid, thimerosal, or the like. In many cases, it will be preferable to include an isotonic agent, for example, without limitation, one or more sugars or sodium chloride, or any combination thereof. Prolonged absorption of the injectable compositions can be brought about by the use in the compositions of agents delaying absorption, for example without limitation, aluminum monostearate, gelatin, or a combination thereof.

While systemic administration is contemplated to be effective in many embodiments as disclosed herein, it is also contemplated that formulations of the disclosed drug delivery compositions may be suitable for direct injection into one or more organs, tissues, or cell types in the body. Administration of the disclosed compositions may be conducted using suitable means, including those known to the one of ordinary skill in the relevant medical arts.

The pharmaceutical formulations comprising mesoporous silicon drug delivery particles as disclosed herein are not in any way limited to use only in humans, or even to primates, or mammals. In certain embodiments, the methods and compositions disclosed herein may be employed using avian, amphibian, reptilian, or other animal species. In preferred embodiments, however, the compositions disclosed herein are preferably formulated for administration to a mammal, and in particular, to humans, in a variety of diagnostic, therapeutic, and/or prophylactic regimens. The compositions disclosed herein may also be provided in formulations that are acceptable for veterinary administration, including, without limitation, to selected livestock, exotic or domesticated animals, companion animals (including pets and such like), non-human primates, as well as zoological or otherwise captive specimens, and such like.

Gene-Silencing Agents

Research on gene-silencing agents including small interfering RNA (siRNA) and non-coding microRNA has exploded in the last decade. These agents can be developed as drugs for the treatment of human diseases such as cancer and cardiovascular diseases. Delivery vehicles are needed to package the gene-silencing agents and deliver them to the disease site, since the naked molecule:

1) would be destroyed by plasma and tissue nucleases immediately;

2) will be trapped in liver and spleen even if they survive the attack from nucleases; and 3) cannot pass the cellular membrane to enter the cell for drug action since an unmodified molecule carries a net negative charge.

However, there are not many choices available for a suitable delivery vehicle. Most current ones, such as liposomes, lipid nanoparticles, and polymeric nanoparticles are designed for targeting the liver. The present inventors have designed and developed a new platform—polycation-functionalized nanoporous silicon (PCPS)—to deliver therapeutic agents (including, for example, nucleic acid molecules such as small interfering RNA-derived gene-silencing agents) to selected cells of interest such as cancer cells or tumor tissues. The PCPS particles disclosed herein have a high binding capacity to siRNA and microRNA, and can deliver the agents to solid tumors in multiple tissues/organs including, for example, breast, liver, lung, and bone.

There is no toxicity associated with the new delivery system, and it has been demonstrated to be capable of delivering a broad range of polynucleotides to selected cells, and as such, has broad potential in the development of new therapeutics.

siRNAs siRNA oligonucleotides have been delivered to target cells using conventional delivery vehicles, such as liposomes (Nishimura et al., 2013). Most siRNA products in current clinical trials are packaged either in liposomes or in lipid nanoparticles. The disease indications are liver-related metabolic diseases, liver cancer, or other cancer types that have metastasized to the liver (Fitzgerald et al., 2014; Sehgal et al., 2013).

The reason for the disease indications is that the nanoparticles are enrichment in the liver. The inventors and their collaborators have previously developed a multistage-vector platform to deliver siRNAs to other tissues for cancer treatment (Shen et al., 2013; Dave et al., 2014). In those studies, the resulting siRNAs were packaged in nanoliposomes. That platform, however, has some important limitations: 1) loading efficiency is low; and 2) nanoliposomes are easy to break. Thus, there is a significant problem when storing and transporting MSV/siRNAs for periods longer than a few hours.

With the current system, the inventors have demonstrated that they can load a lot more siRNA into the same amount of porous silicon particles (up to 100-fold more nucleic acids) since the siRNA or microRNA molecules are not pre-packaged into nanoparticles, and thereby reducing the total amount of porous silicon for each treatment. Less silicon translates to less toxicity. Moreover, the loaded PCPS particles can be dried down, and stored/transported over periods of several days to several weeks without a significant loss in activity or efficacy.

Thus, the compositions described herein, offer many significant improvements to existing techniques and delivery regimens in the conventional arts.

BRIEF DESCRIPTION OF THE DRAWINGS

For promoting an understanding of the principles of the invention, reference will now be made to the embodiments, or examples, illustrated in the drawings and specific language will be used to describe the same. It will, nevertheless be understood that no limitation of the scope of any invention disclosed herein is thereby intended. Any alterations and further modifications in the described embodiments, and any further applications of the principles of the invention as described herein are contemplated as would normally occur to one of ordinary skill in the art to which the present disclosure relates.

The following drawings form part of the specification, and are included to demonstrate certain aspects of the disclosure. For applications that contain at least one drawing that is executed in color, copies of the application publication, or a patent granted thereon containing color drawing(s) may be obtained from the United States Patent and Trademark Office upon request and payment of the necessary fee.

The invention(s) disclosed herein may be better understood by reference to the following description taken in conjunction with the accompanying drawings, in which like reference numerals identify like elements, and in which:

Figure 1:
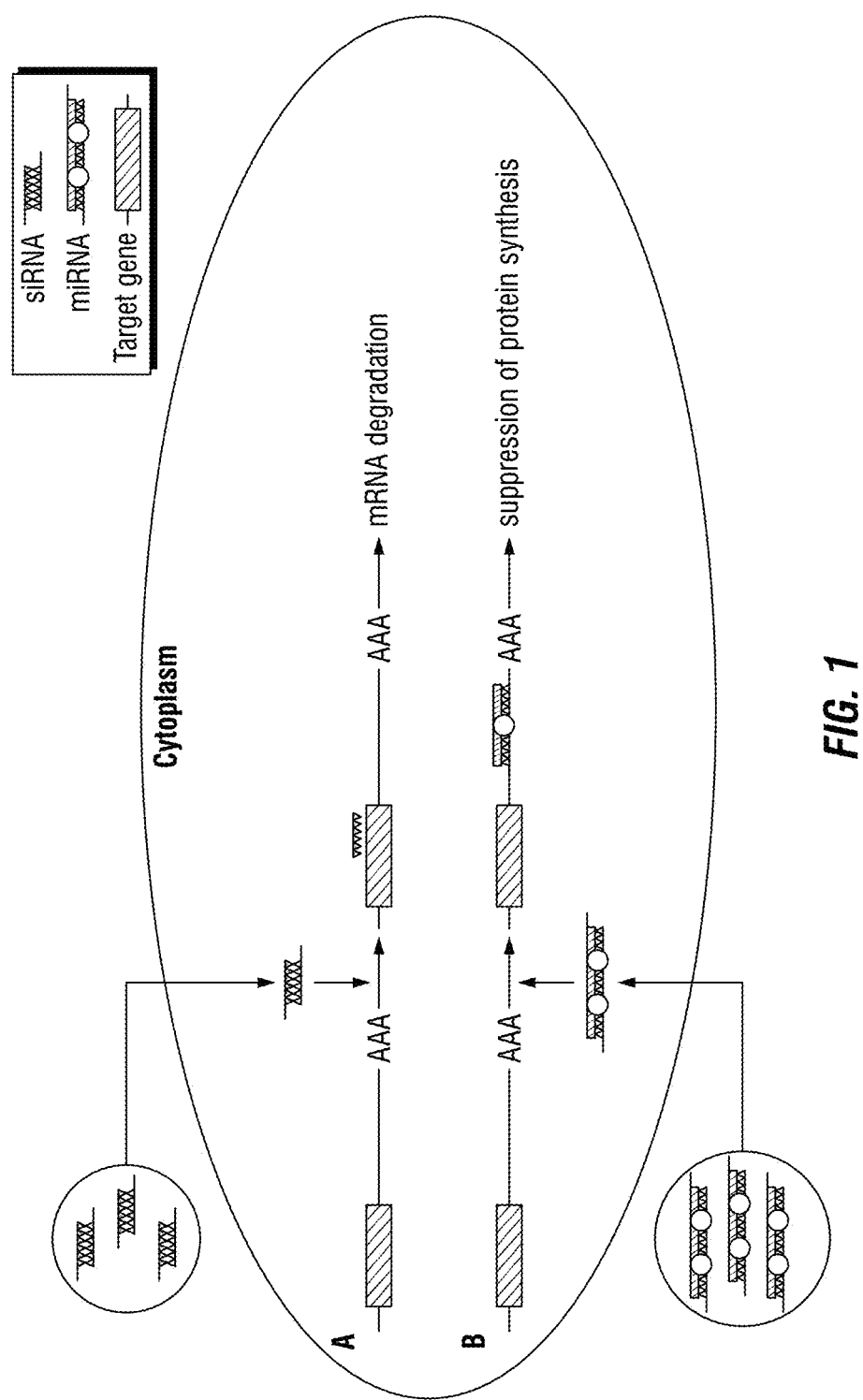
Figure 2A:
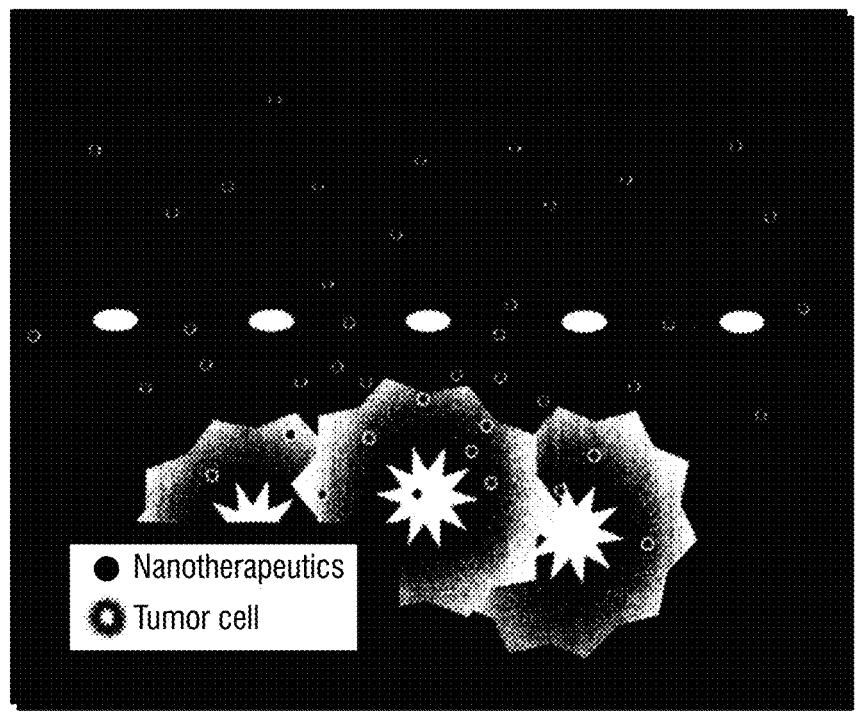
Figure 2B:
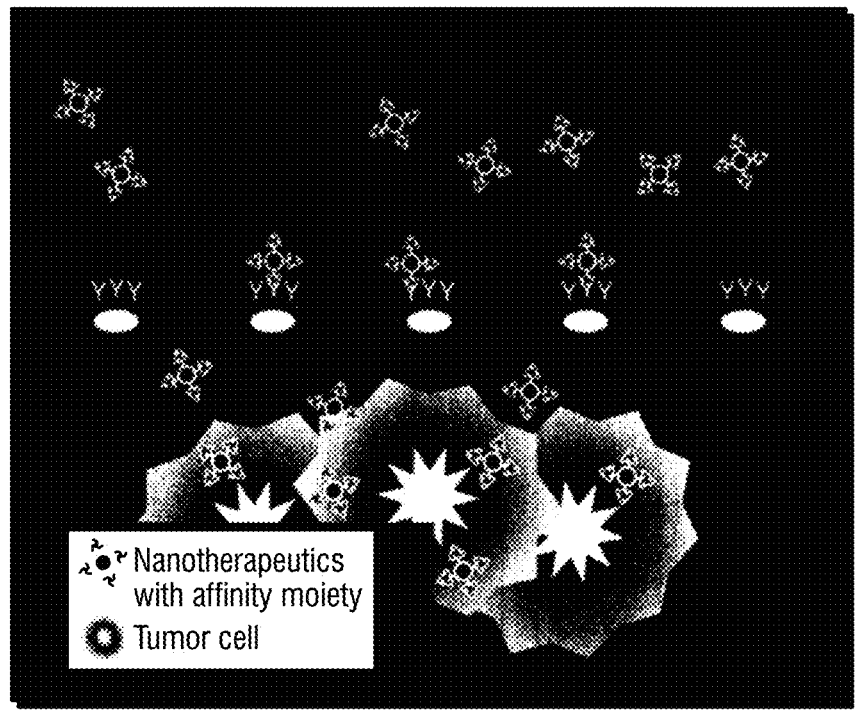
Figure 3:
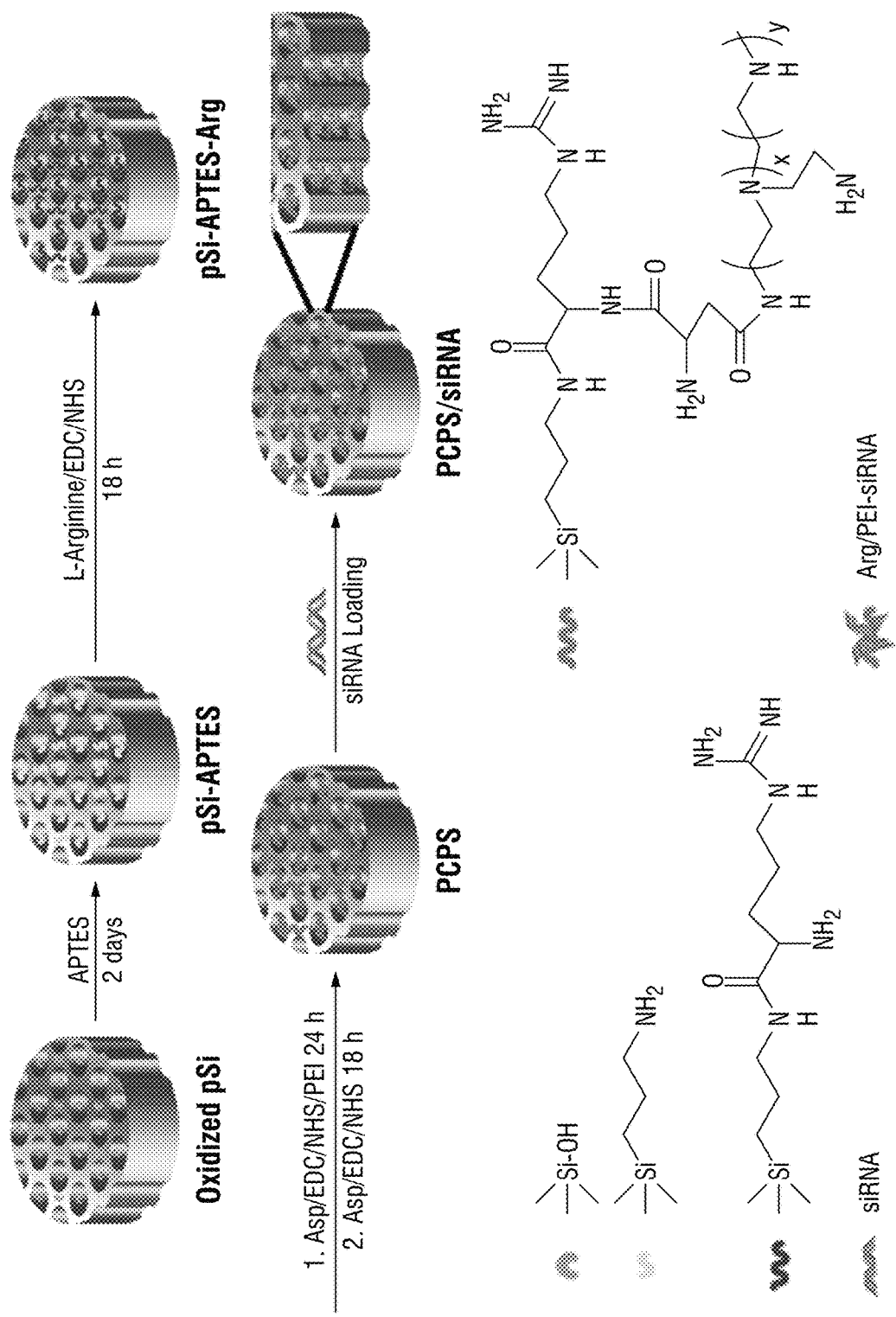
Figure 4A:
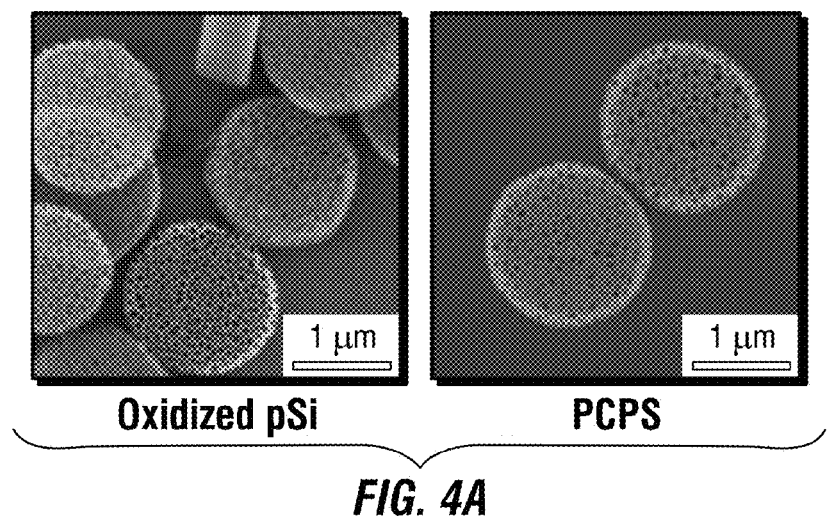
Figure 4B:
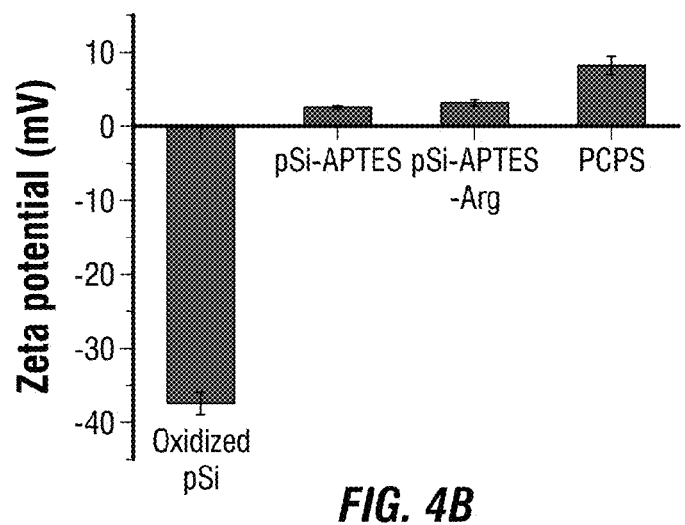
Figure 4C:
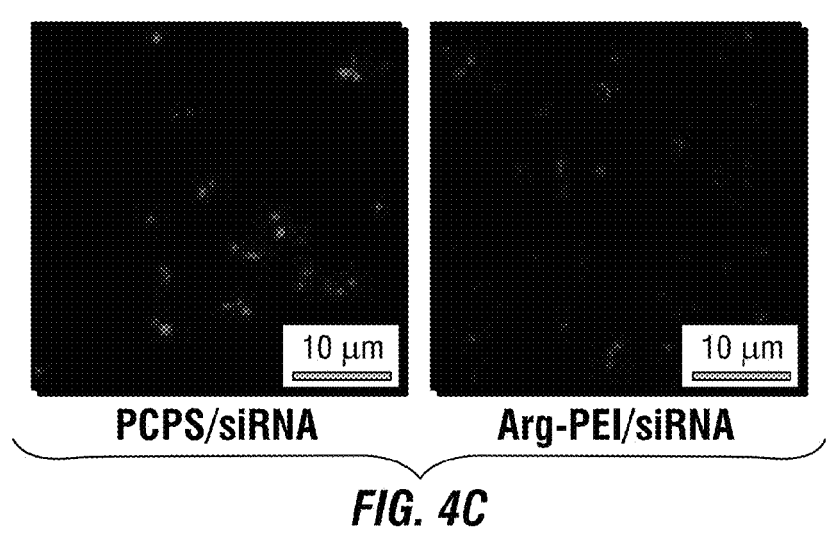
Figure 4D:
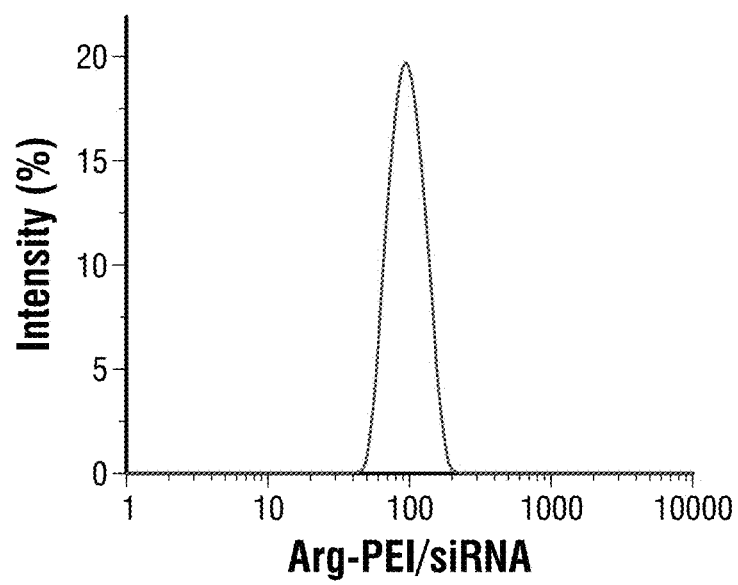
Figure 4E:
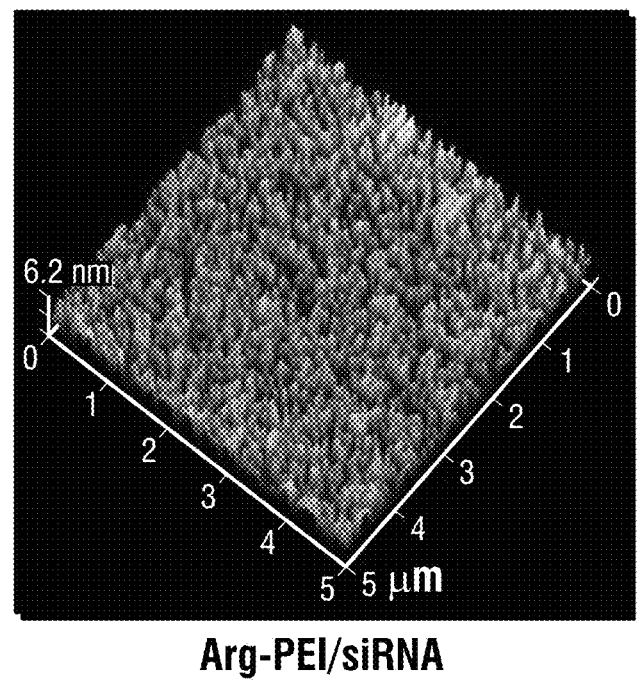
Figure 5A:
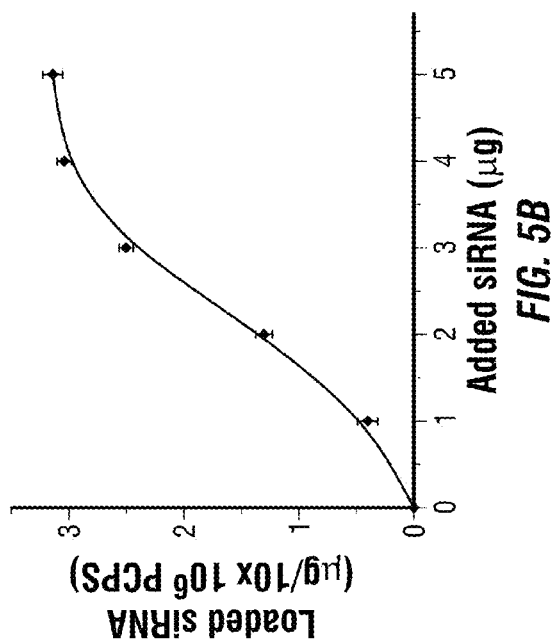
Figure 5B:
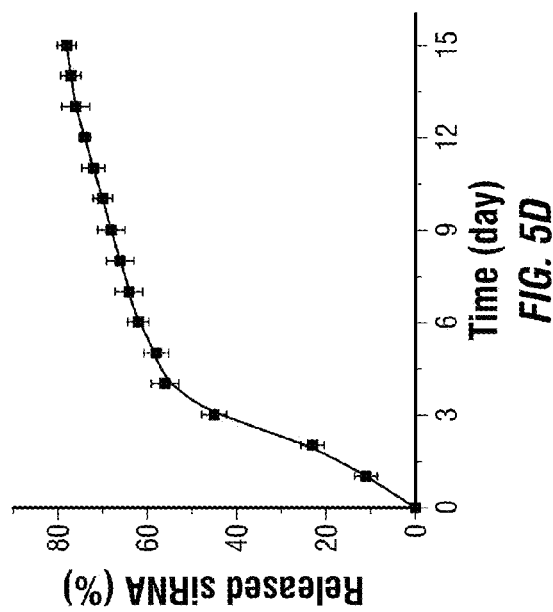
Figure 5C:
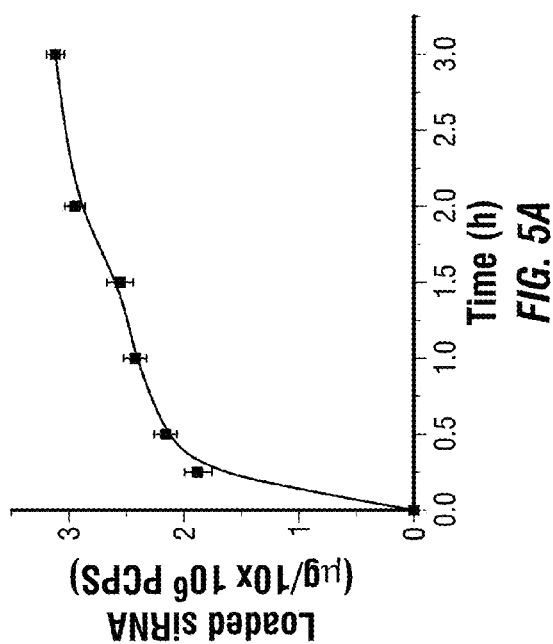
Figure 5D:
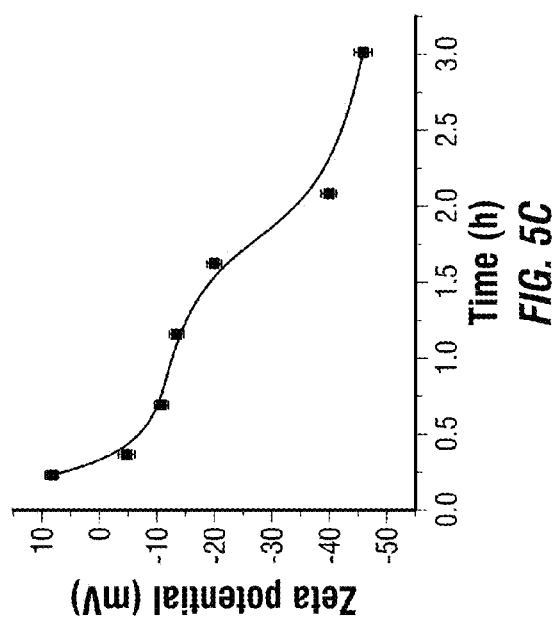
Figure 6A:
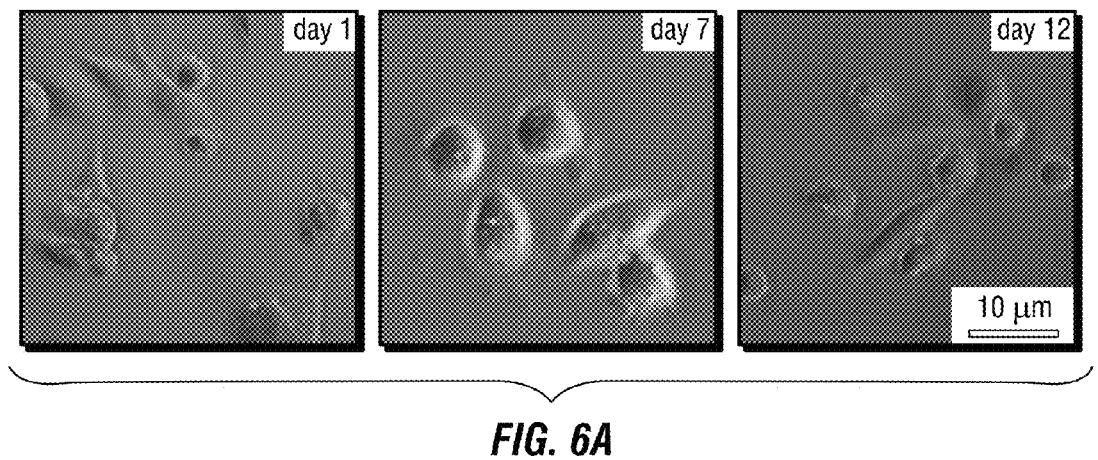
Figure 6B:
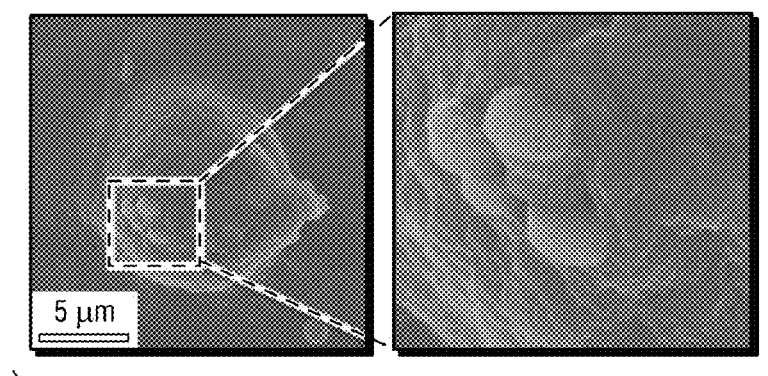
Figure 6C:
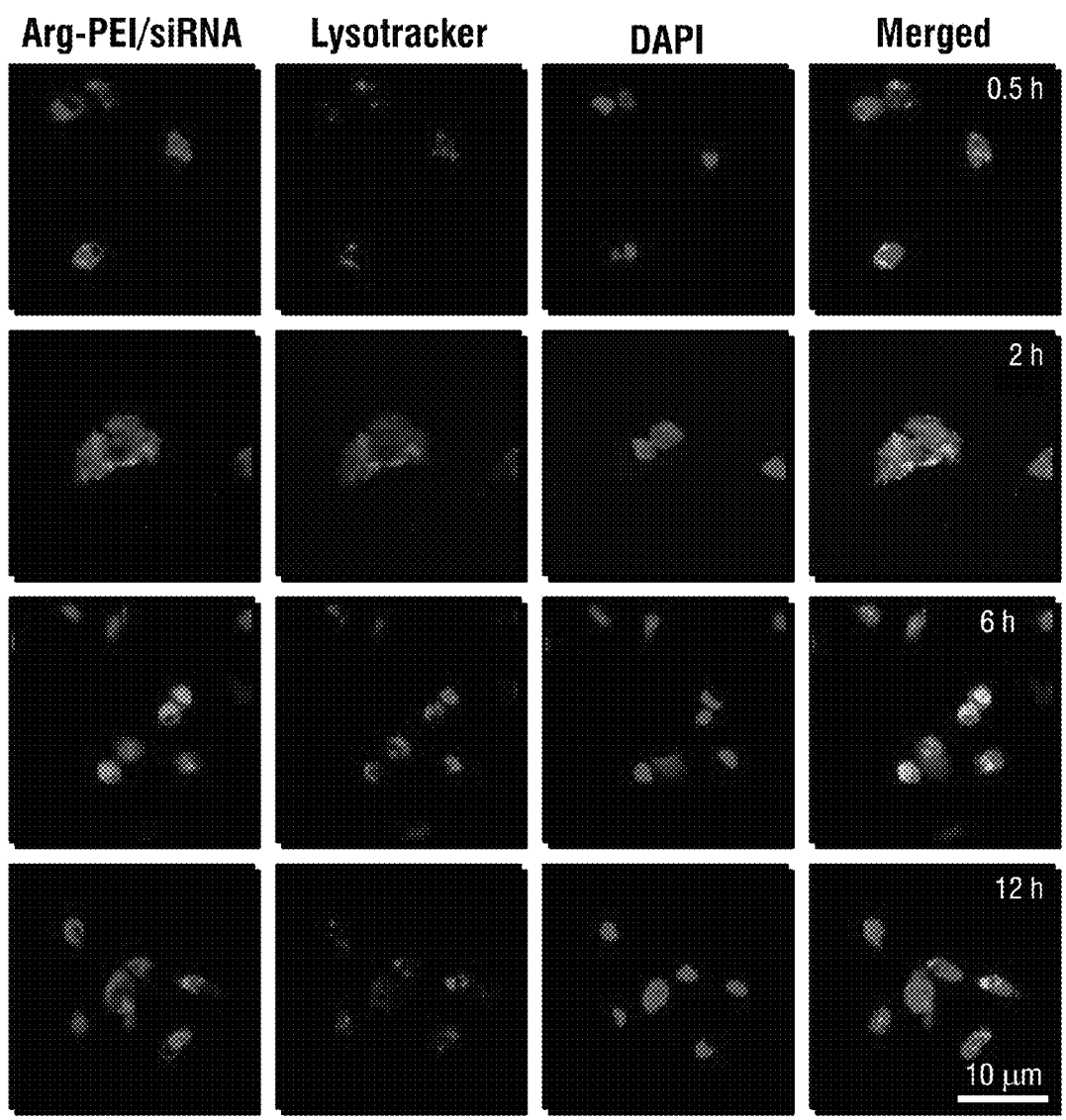
Figure 7A:
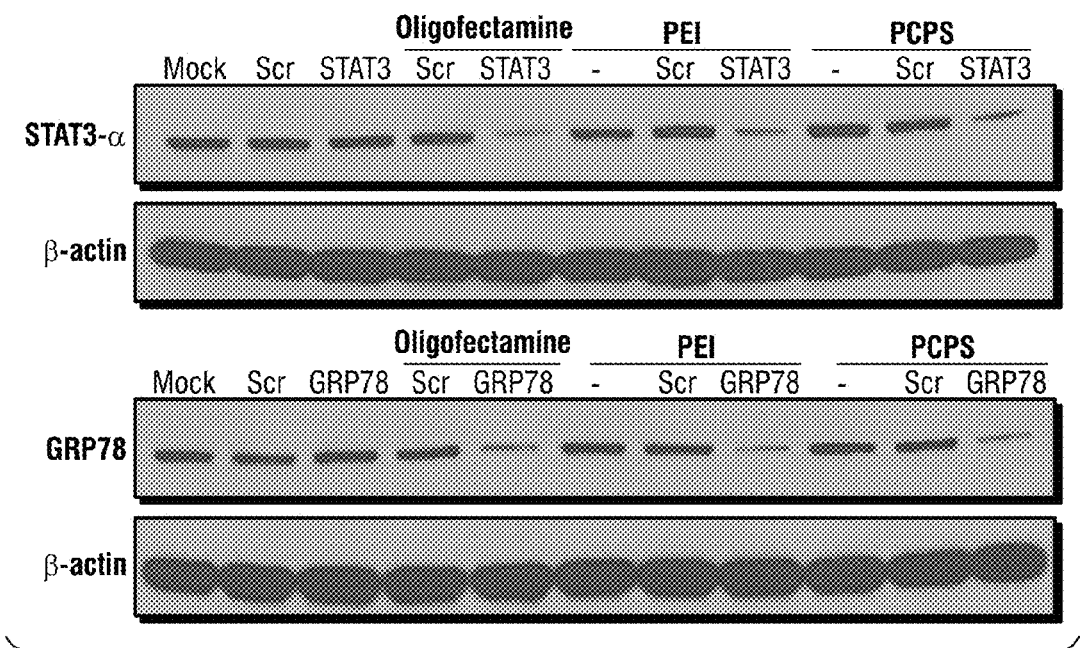
Figure 7B:
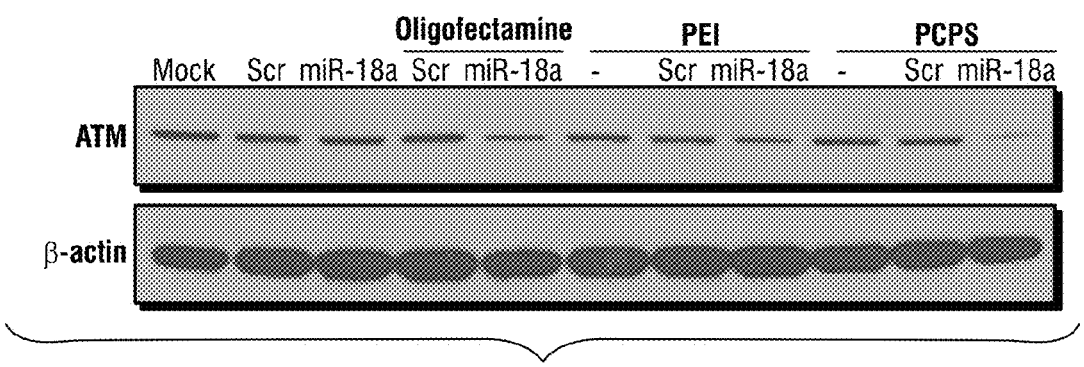
Figure 7C:
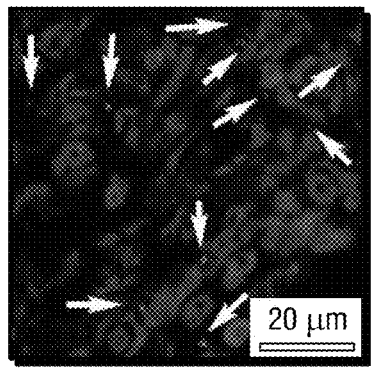
Figure 7D:
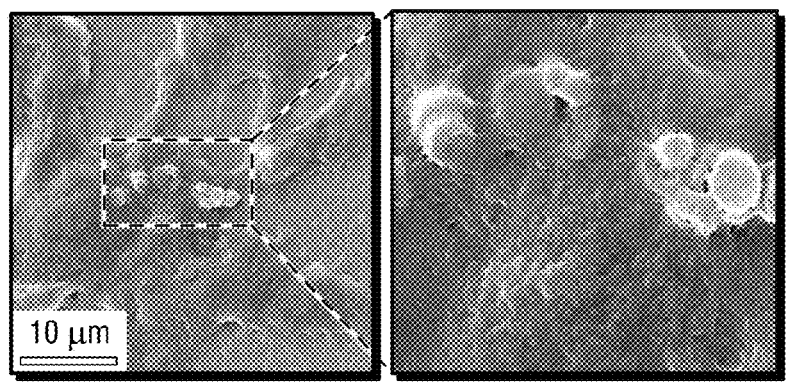
Figure 7E:
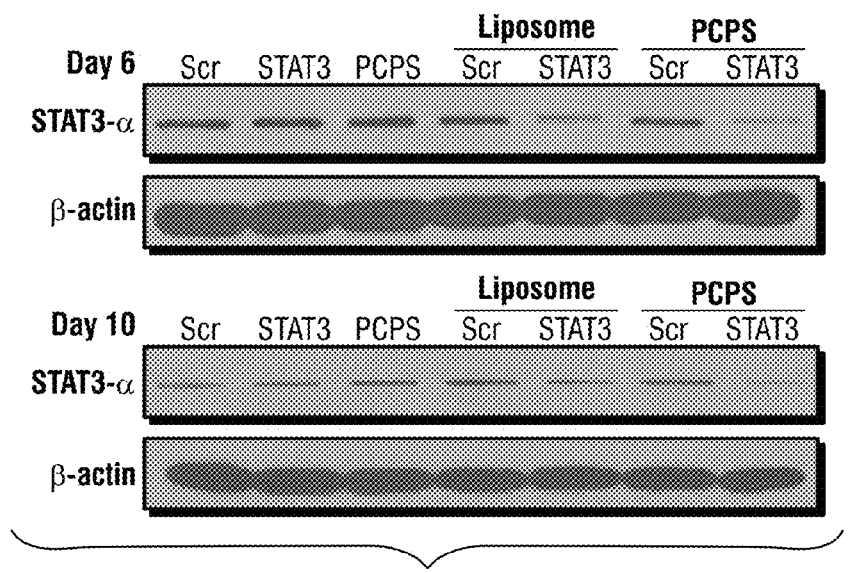
Figure 7F:
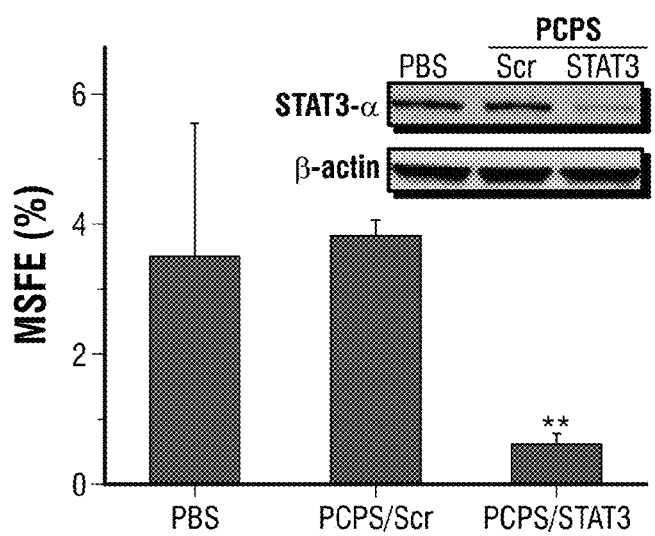
Figure 9C:
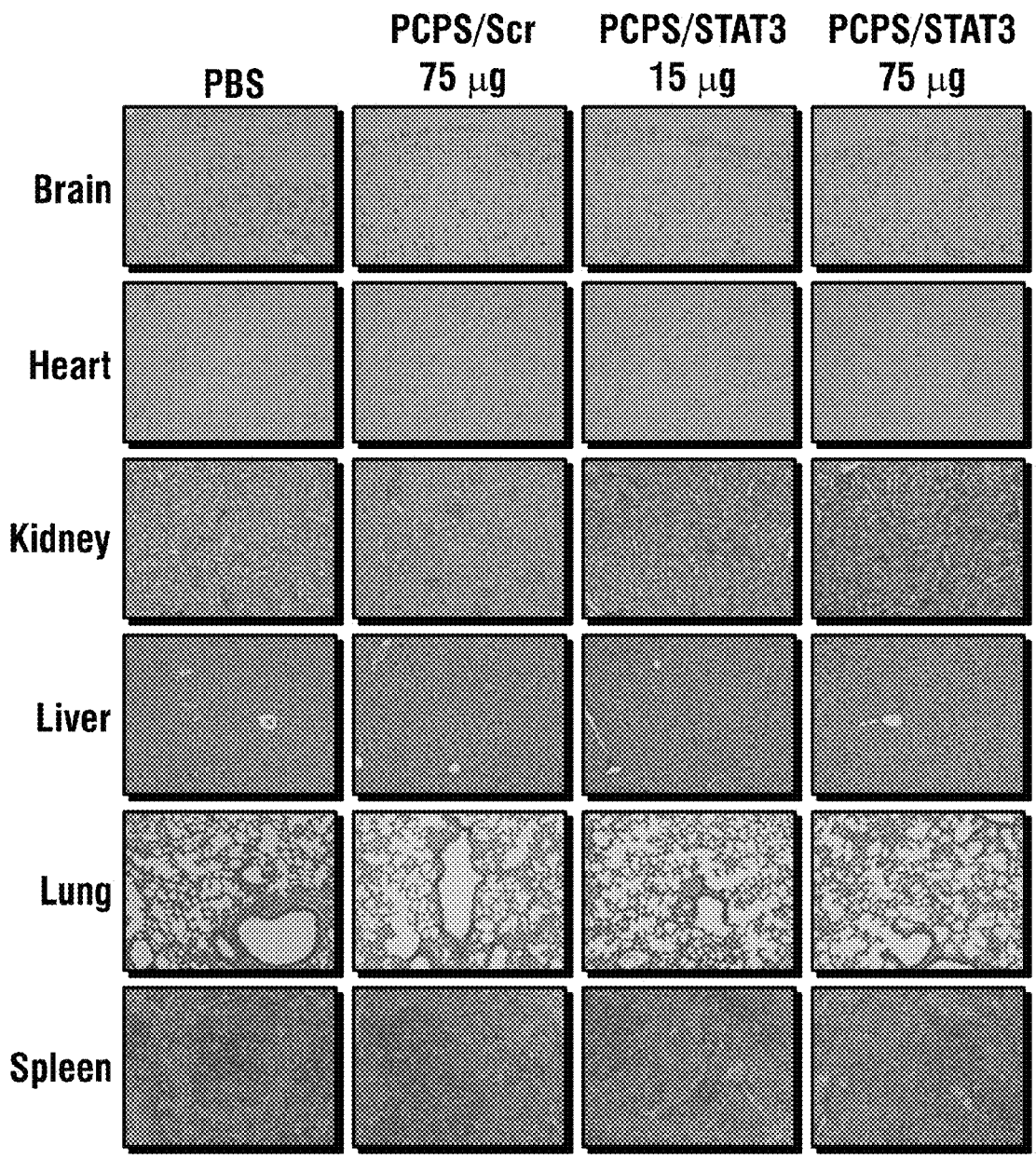
Figure 10A:
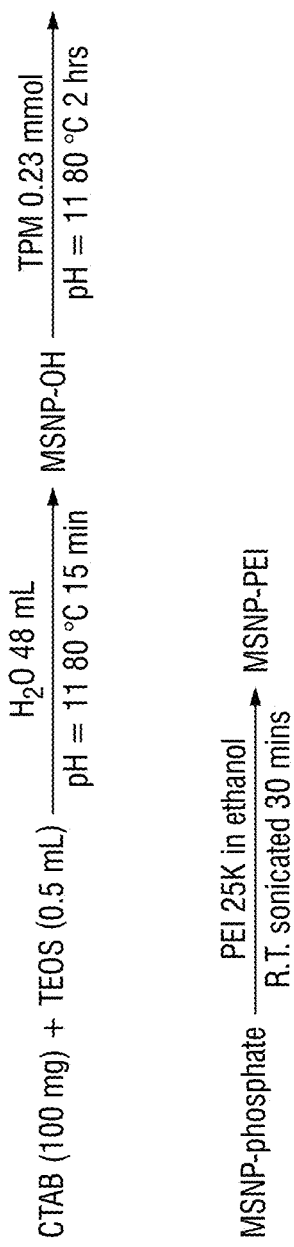
Figure 10B:
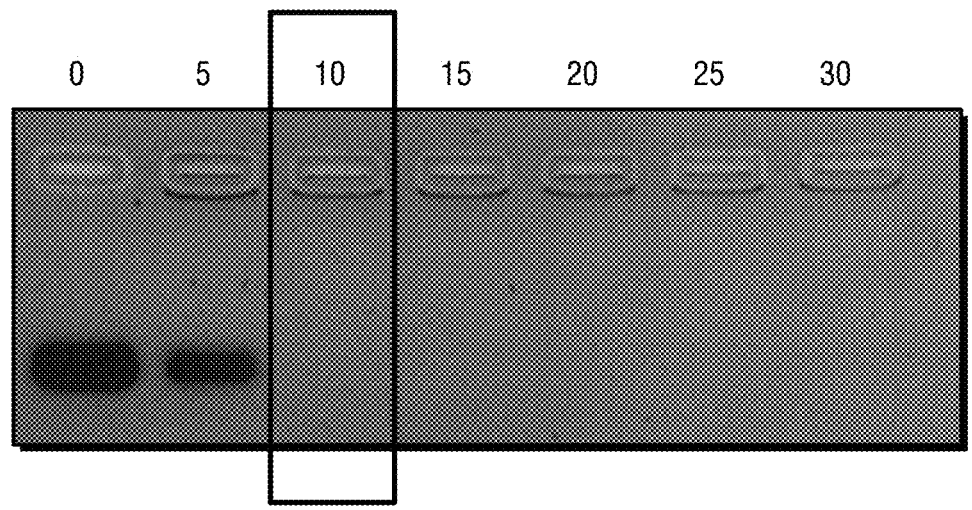
Figure 11A:
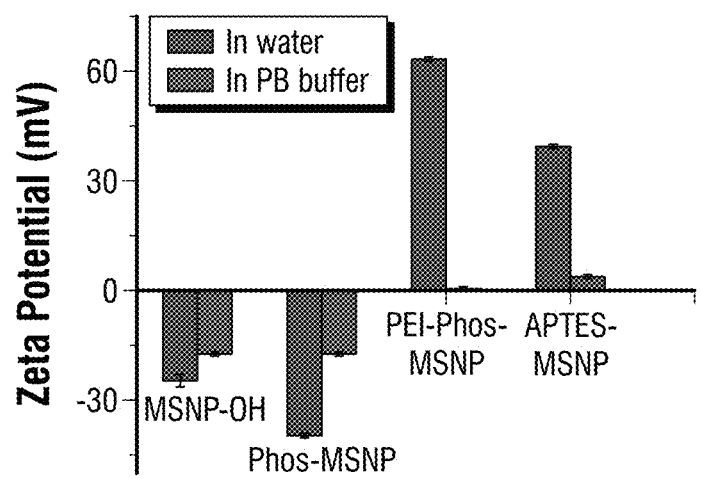
Figure 11B:
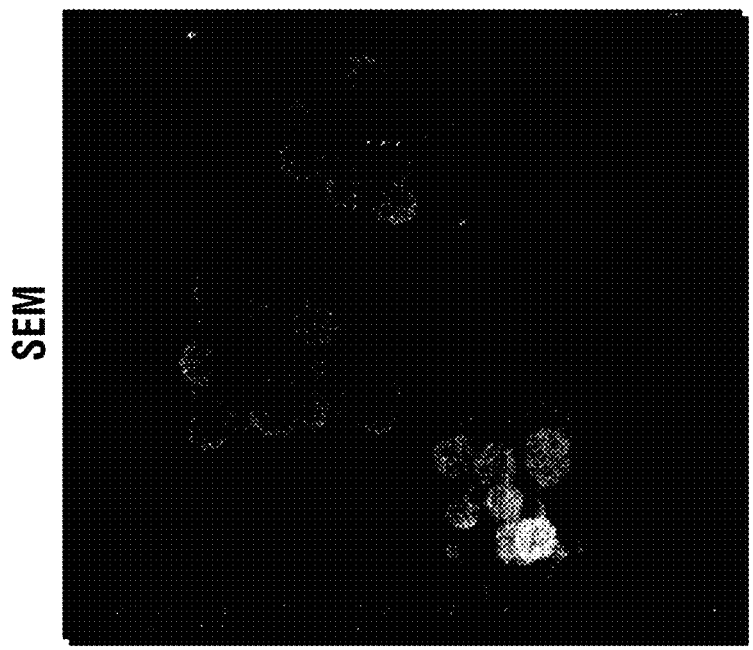
Figure 11C:
Figure 11D:
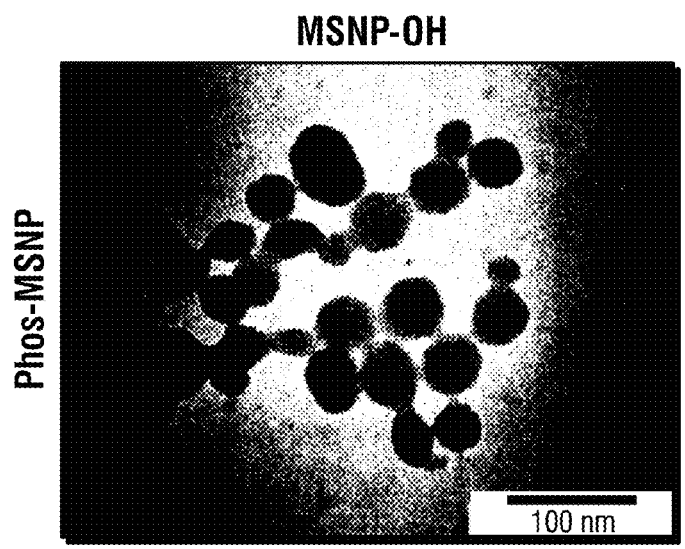
Figure 11E:
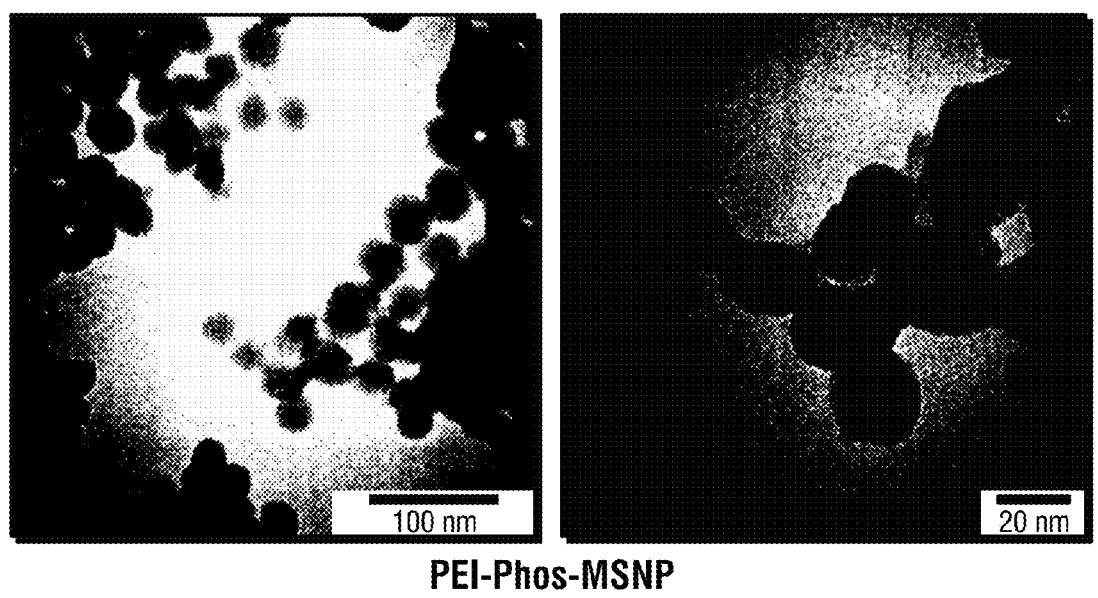
Figure 12A:
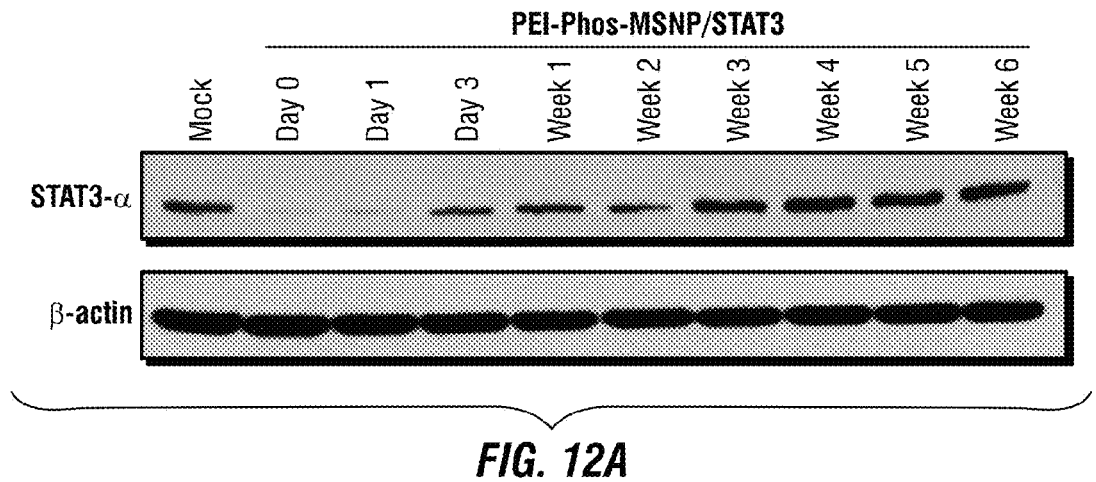
Figure 12B:
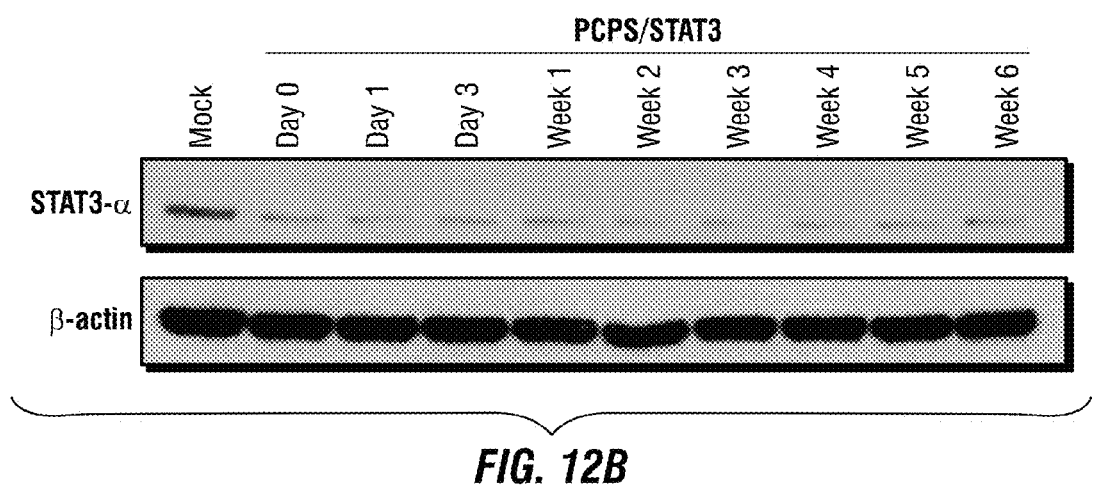
Figure 13:
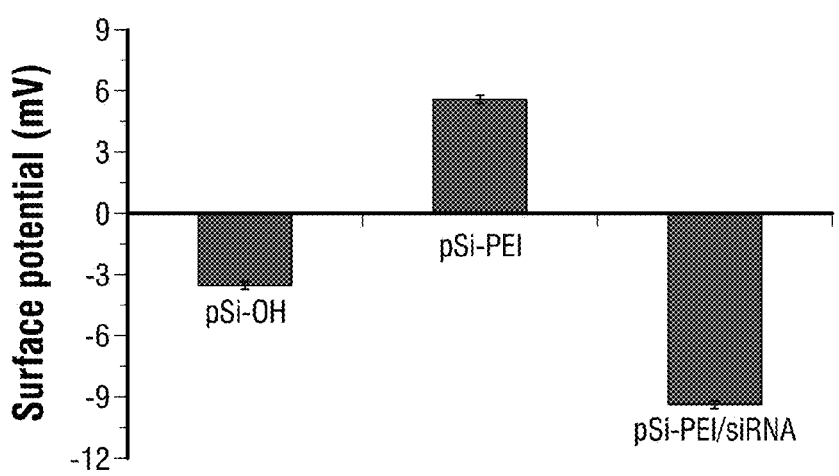
Figure 14A:
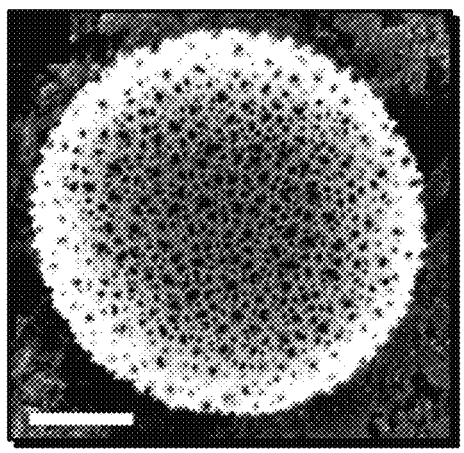
Figure 14B:
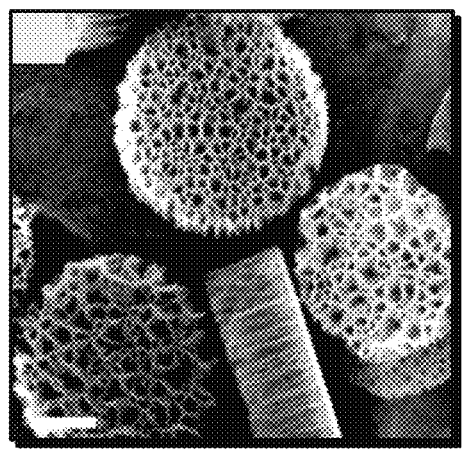
Figure 14C:
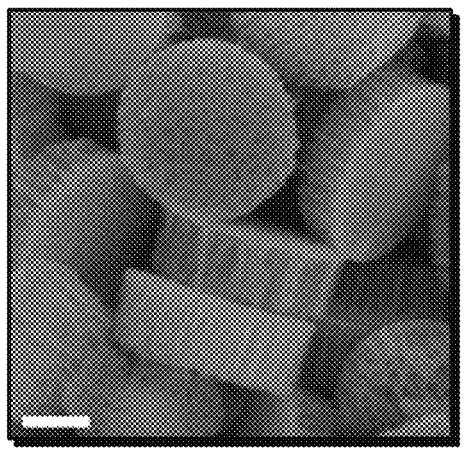
Figure 14D:
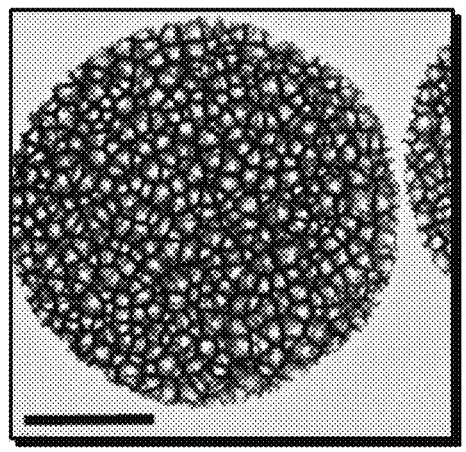
Figure 14E:
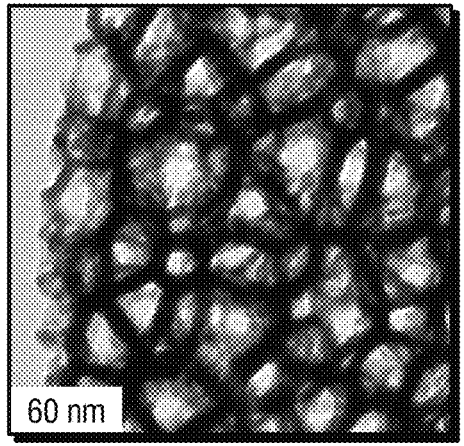
Figure 14F:
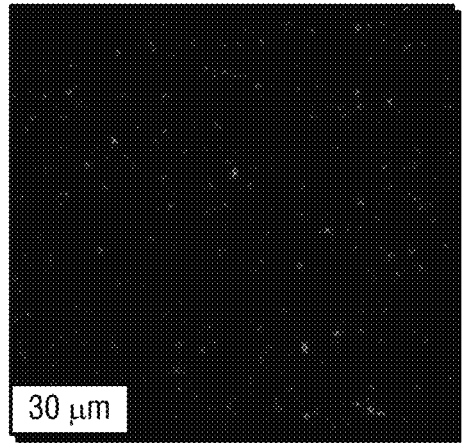
Figure 16A:
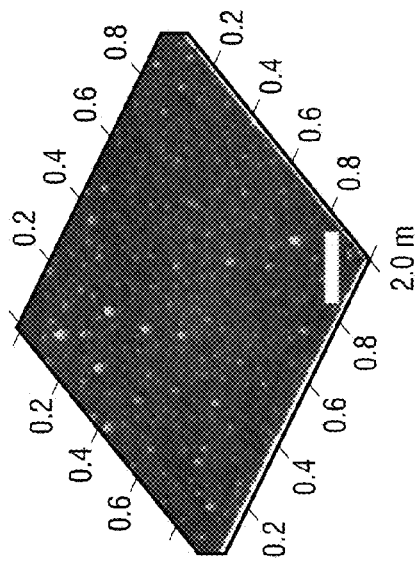
Figure 16B:
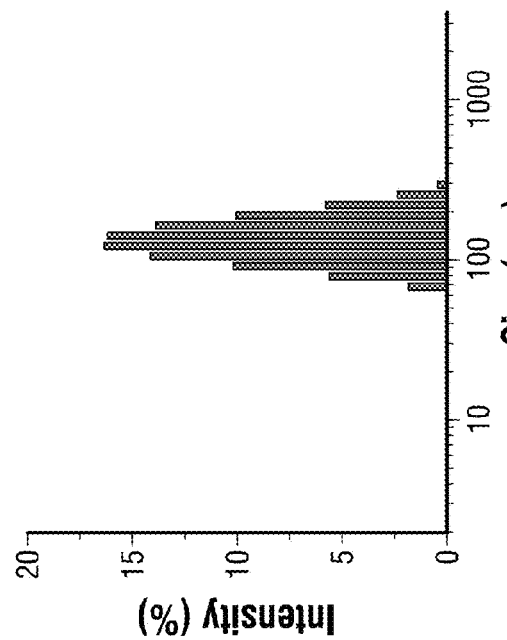
Figure 15:
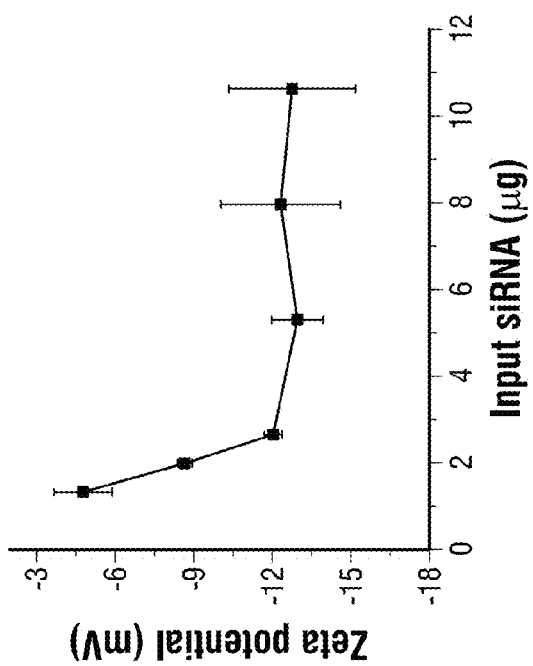
Figure 18:
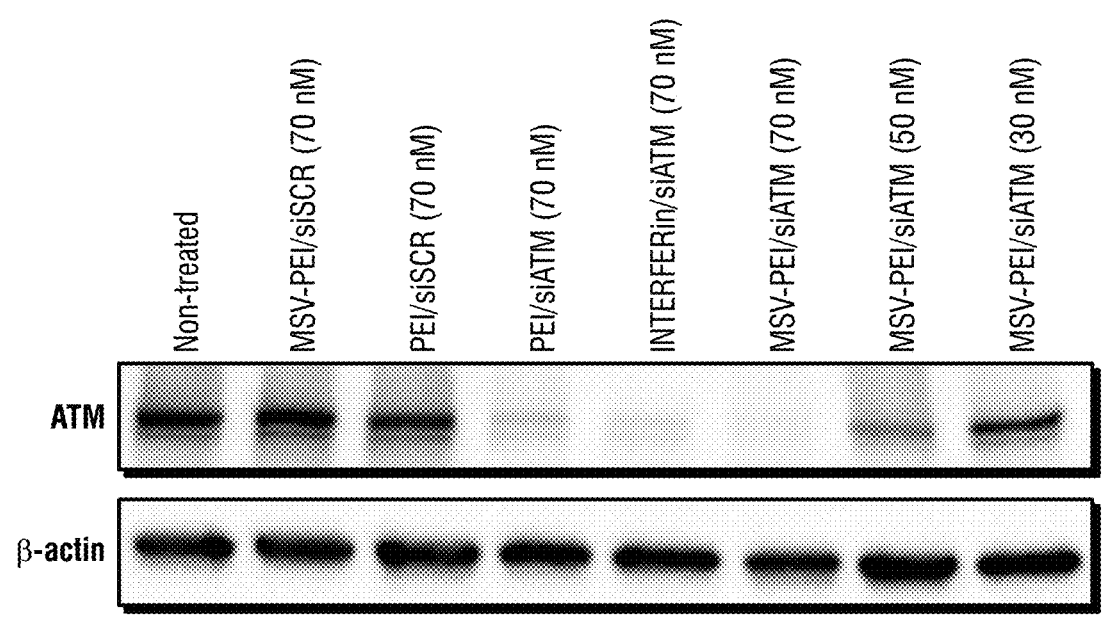
Figure 19A:
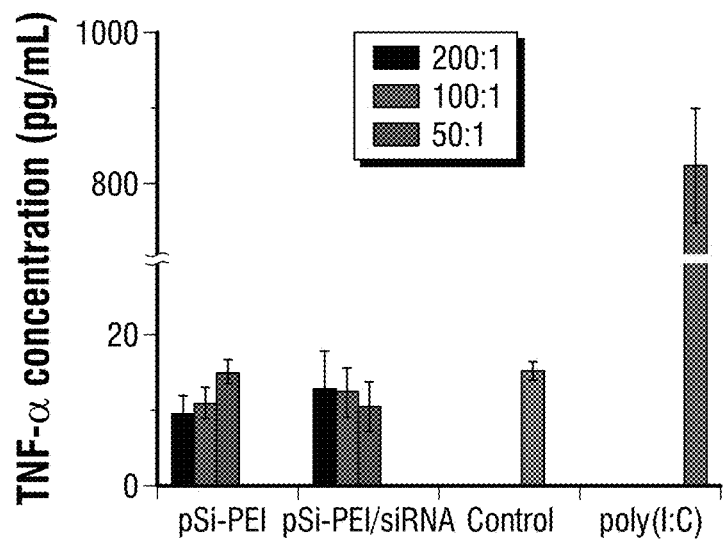
Figure 19B:
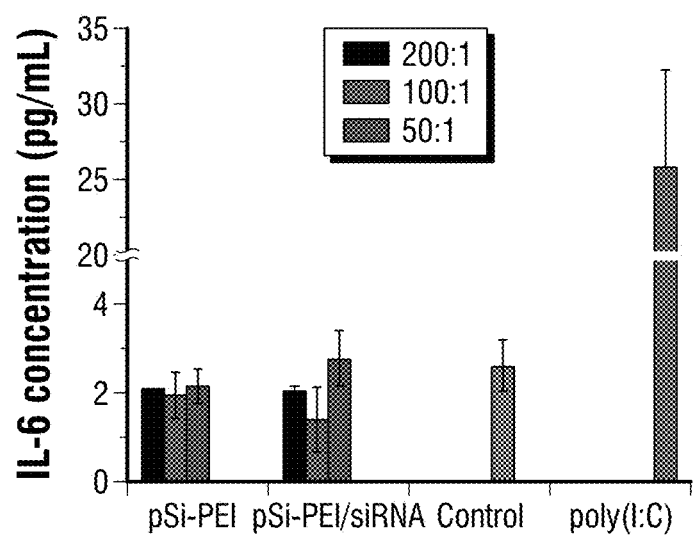
Figure 20:
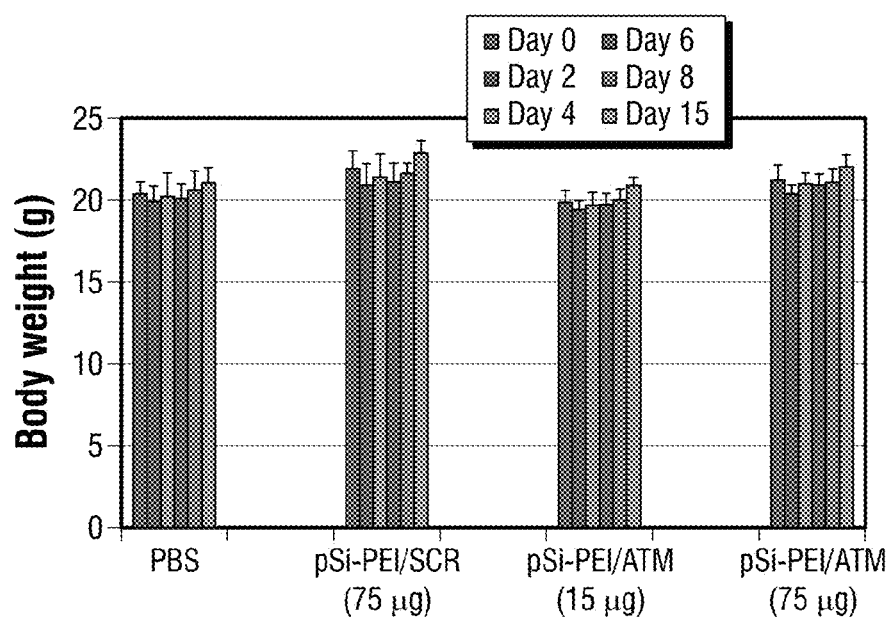
Figure 22:
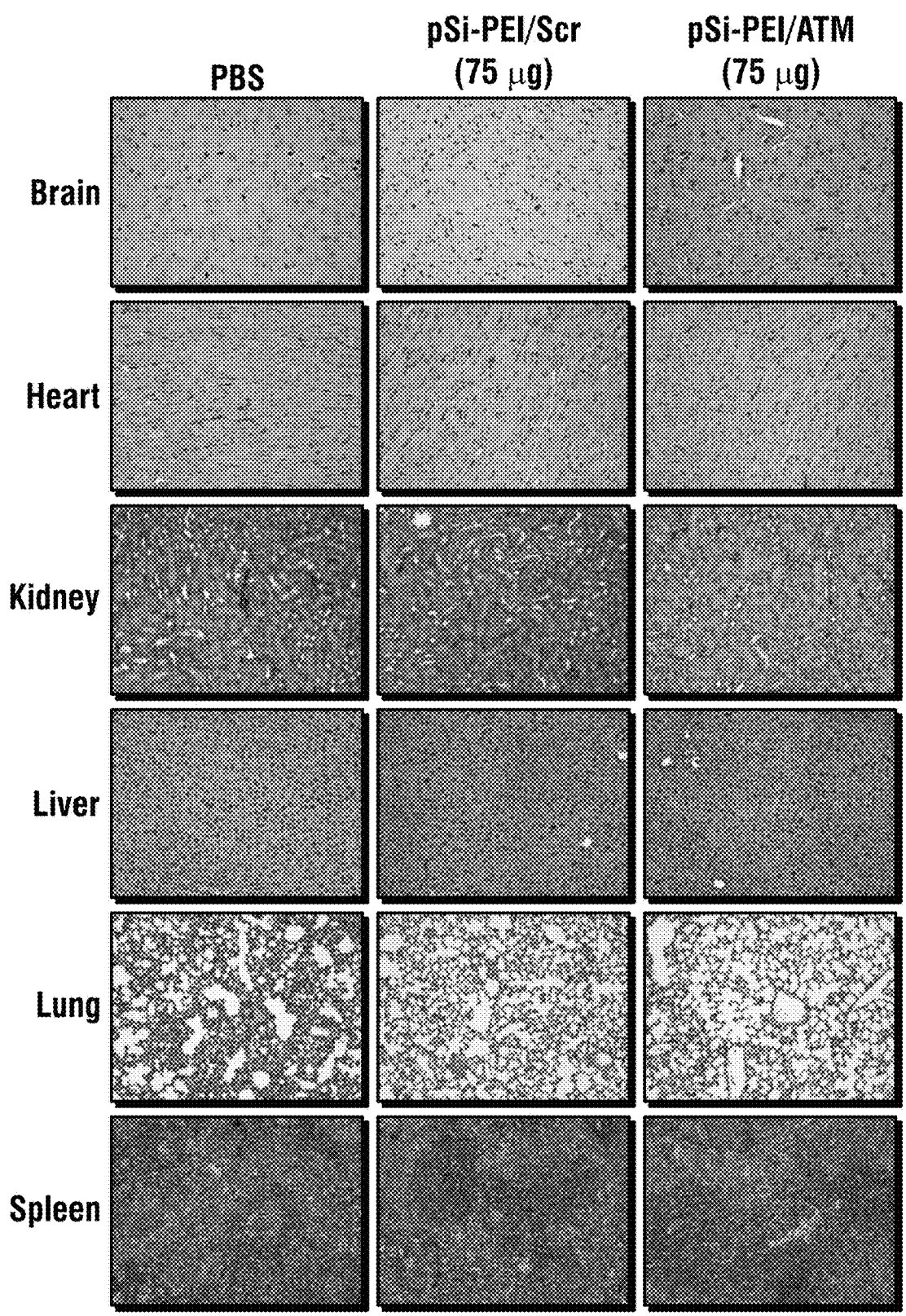

FIG. 1 illustrates a schematic view of the mechanisms of small interfering RNA (siRNAs) and microRNAs (miRNAs). siRNAs and miRNAs are packaged into nanoparticles for effective delivery. Strand A: Once inside the cell, the anti-sense strand of the siRNA duplex anneals to the corresponding mRNA molecule (inside or outside of the open-reading frame) and triggers mRNA degradation. Strand B: On the other hand, the microRNA targets the 3' un-translated region of the mRNA, and suppresses protein synthesis;

FIG. 2A and FIG. 2B show schematic views of an exemplary nanoparticle delivery in accordance with one aspect of the present invention. In FIG. 2A, exemplary nanoparticle delivery by targeting is shown. In this mode, nanoparticles pass through the leaky vasculature and enter tumor tissues. In FIG. 2B, an exemplary nanoparticle delivery by active targeting is depicted. In this mode, the surface of nanoparticles is coated and/or conjugated with an active targeting moiety, such as a peptide, an antibody, or an aptamer. Binding of the targeting moiety with cell-surface molecules then facilitates tumor tissue entry of the nanoparticles;

FIG. 3 shows a schematic illustration of an exemplary fabrication of PCPS as a delivery carrier for gene silencing agents in accordance with one aspect of the present invention;

FIG. 4A, FIG. 4B, FIG. 4C, FIG. 4D, and FIG. 4E show the characterization of PCPS as a delivery carrier for gene silencing agents. FIG. 4A: SEM images of oxidized porous silicon (pSi) as the starting material and PCPS as the final product. FIG. 4B: Changes in zeta potential of particles at various stages of fabrication. Results are presented as the mean of five measurements±standard deviation. FIG. 4C: Confocal microscopic images of PCPS/siRNA (left panel) and the released Arg-PEI-siRNA polyplex nanoparticles. Red fluorescence was from the Alexa Fluor© 555-conjugated siRNA. FIG. 4D: Size distribution of released siRNA polyplex nanoparticles measured by dynamic light scattering. FIG. 4E: atomic force microscopic image for size analysis of siRNA polyplex nanoparticle;

FIG. 5A, FIG. 5B, FIG. 5C, and FIG. 5D illustrate the loading of siRNA into PCPS and release of siRNA polyplex nanoparticles in accordance with one aspect of the present invention. FIG. 5A: Time-dependent loading of siRNA into PCPS. Scramble siRNA was used to test time-dependent loading, and UV absorbance of the supernatant at 260-nm was measured to assess loading capacity. FIG. 5B: Dose-dependent loading of siRNA into PCPS. FIG. 5C: Zeta potential changes during siRNA loading into PCPS. FIG. 5D: Release of siRNA nanoparticle from the carrier. PCPS/Alexa Fluor© 555-siRNA was incubated in PBS with 10% fetal bovine serum. Supernatant was separated from the particles, and fluorescence intensity was measured at Ex543/Em590. Results are presented as the mean of five measurements±standard deviation;

FIG. 6A FIG. 6B, and FIG. 6C show the cellular uptake of PCPS/siRNA and intra-cellular trafficking of Arg-PEI/siRNA polyplex nanoparticles. FIG. 6A: Time-dependent release of Alexa Fluor© 555-siRNA inside tumor cells. PCPS/Alexa Fluor© 555 siRNA particles (in red) were added into MDA-MB-231 cell culture, and fluorescence from particles was monitored with a confocal microscope on days 1, 7, and 12 after incubation. FIG. 6B: SEM images of cellular internalization of PCPS/siRNA. Multiple particles were at various stages of cellular entry. FIG. 6C: Intra-cellular trafficking of Arg-PEI/siRNA polyplex nanoparticles. Arg-PEI/FAM-siRNA polyplex nanoparticles (in green) were added into MDA-MB-231 cell culture. Cells were harvested at the indicated timepoints, and stained with LysoTracker® for late endosomes/lysosomes (in red) and DAPI for nuclei (in blue). Fluorescent images was captured with a confocal microscope;

FIG. 7A, FIG. 7B, FIG. 7C, FIG. 7D, FIG. 7E, and FIG. 7F show the knockdown of gene expression in vitro, and in a murine model of MDA-MB-231 primary tumors. FIG. 7A: Western blot analyses on knockdown of STAT3 and GRP78 expression in MDA-MB-231 cells following siRNA treatment. Cells were treated with the indicated agents, and harvested 72 hrs later for protein analysis. The (3-actin level indicated equal protein loading. FIG. 7B: Knockdown of ATM expression in MCF-7 cells. FIG. 7C: Accumulation of PCPS/siRNA in primary MDA-MB-231 tumor. Mice bearing MDA-MB-231 primary tumor were administrated with $150 \times 10^6$ PCPS/Alexa Fluor© 555 siRNA by tail vein injection. They were sacrificed 6 hrs later, and tumor samples were processed for confocal analysis. PCPS/siRNA particles were in red (Alexa Fluor© 555) and highlighted by the white arrows, and nuclei of tumor cells were stained in blue by DAPI. FIG. 7D: SEM image of PCPS/siRNA in tumor tissue. FIG. 7E: Knockdown of STAT3-α expression in vivo. Each mouse bearing MDA-MB-231 primary tumor received $150 \times 10^6$ PCPS loaded with 15 μg siRNA by i.v. on Day 1. Mice were sacrificed 6 or 10 days later for expression analysis by Western blot. FIG. 7F: Mammosphere formation efficiency (MSFE) in MDA-MB-231 primary tumor cells treated with PCPS/siRNA. The inserted Western blot result shows gene expression levels in the cells used for the MSFE assay. MSFE results were averaged from three mice/group;

FIG. 8A-1, FIG. 8A-2, FIG. 8B-1, FIG. 8B-2, FIG. 8B-3, FIG. 8B-4, FIG. 8B-5, and FIG. 8B-6 show in vitro and in vivo acute toxicity. RAW-264.7 mouse macrophage cells were incubated with the indicated agents for 24 hrs, and TNF-α and IL-6 levels in supernatant were measured by ELISA. Results are presented as the mean of three measurements±standard deviation. Changes in levels of selected serum cytokine/chemokine/colony-stimulating factors in post-treatment mice are shown. Blood samples were collected either 2- or 24-hrs after i.v. dosing of treatment agents. A multiplexed bead-based immunoassay was used to measure levels of the cytokines/chemokines/colony-stimulating factors. Results were the average from three mice per group. *p<0.05; **p<0.01;

FIG. 9A-1, FIG. 9A-2, FIG. 9B-1, FIG. 9B-2, FIG. 9B-3, FIG. 9B-4, FIG. 9B-5, FIG. 9B-6, and FIG. 9C show the analysis on sub-acute toxicity from PCPS/STAT3 siRNA. Mice (n=3/group) were treated once a week for four weeks with the indicated agents. They were sacrificed 24 hrs after the final treatment, with hematological analysis (FIG. 9A-1 and FIG. 9A-2), blood chemistry analysis (FIG. 9B-1, FIG. 9B-2, FIG. 9B-3, FIG. 9B-4, FIG. 9B-5, and FIG. 9B-6), and histological analysis ( ) performed to evaluate potential toxicity. Abbreviations: ALT, alanine aminotransferase; ALB, albumin; ALKP, alkaline phosphatase; Arg, arginine; AST, aspartate aminotransferase; BUN, blood urea nitrogen; GRAN, granulocytes; HCT, hematocrit; HGB, hemoglobin; LDH, lactate dehydrogenase; LYMPH, lymphocytes; MCH, Mean Corpuscular Hemoglobin; MCHC, mean corpuscular hemoglobin concentration; MCV, mean corpuscular volume; MONO, monocytes; MPV, mean platelet volume; PBS, phosphate buffer saline; PLT, platelet count; RBC, red blood cells; RDW, red blood cell distribution width; and WBC, white blood cells;

FIG. 10A and FIG. 10B illustrate mesoporous silica nanoparticles (MSNP) in accordance with one aspect of the present invention. Shown in FIG. 10A is the synthesis and surface modification of MSNP. MSNP-phosphate: refluxing in the mixture of methanol and HCl 24 hrs, wash with methanol; MSNP-PEI: wash with ethanol and PBS; abbreviations: CTAB: cetyltrimethylammonium bromide; TEOS: tetraethylosilicate; TPM: 3-trihydroxysilylpropyl methylphosphonate. FIG. 10B shows an agarose gel electrophoresis of exemplary PEI-Phos-MSNP particles containing siRNA prepared in accordance with one aspect FIG. 9C of the present invention;

FIG. 11A, FIG. 11B, FIG. 11C, FIG. 11D, and FIG. 11E show the characterization of exemplary mesoporous silica nanoparticles (MSNP) in accordance with one aspect of the present invention. FIG. 11A shows the Zeta potential in milliovlts of exemplary particles; FIG. 11B is a scanning electron micrograph of exemplary MSNP-OH particles; FIG. 11C, FIG. 11D, and FIG. 11E are transmission electron micrographs of MSNP-OH, Phos-MSNP, and PEI-Phos-MSNP particles, respectively;

FIG. 12A and FIG. 12B show exemplary stability comparisons of PEI-Phos-MSNP/STAT3 particles (FIG. 12A) prepared in accordance with the present invention, to PCPS/STAT3 particles (FIG. 12B) prepared in accordance with conventional methods available in the prior art; samples were stored at 4° C., siRNA 50 nM, transfection 3 days;

FIG. 13 shows the Zeta potential values of pSi particles with various surface functionalities prepared in accordance with various aspects of the present invention;

FIG. 14A, FIG. 14B, FIG. 14C, FIG. 14D, FIG. 14E and FIG. 14F. Morphological observations of discoidal pSi particles by SEM (FIG. 14A, FIG. 14B, and FIG. 14C), TEM (FIG. 14D and FIG. 14E), and CLSM (FIG. 14F). SEM images of pSi particles (FIG. 14A), pSi-PEI (FIG. 14B), and pSi-PEI/siRNA (FIG. 14C). TEM images of pSi-PEI/siRNA particles were taken at 20000× (FIG. 14D) and 80000× (FIG. 14E) magnifications, respectively. Confocal image of the pSi-PEI/AF 555-siRNA particles (FIG. 14D). Scale bars represent 300 nm unless indicated;

FIG. 15 shows surface potential changes as a function of input siRNA for a given amount of pSi-PEI particles;

FIG. 16A and FIG. 16B show morphological observation (FIG. 16A) and DLS measurement (FIG. 16B) for PEI/siRNA nanoparticles obtained after complete degradation of the pSi matrix (scale bar: 200 nm);

FIG. 17A, FIG. 17B, and FIG. 17C show cellular trafficking study of pSi-PEI/siRNA (FIG. 17A) and PEI/siRNA nanoparticles (FIG. 17B and FIG. 17C). Internalization of particles was performed at 4 hrs (FIG. 17A and FIG. 17B) and 18 hrs post-transfection (scale bar: 20 μm);

FIG. 18 shows gene silencing effect against ATM cancer gene at 60 hrs' post-transfection;

FIG. 19A and FIG. 19B show in vitro biocompatability evaluation by determination of pro-inflammatory cytokines secretion, including: FIG. 19A: TNF-α and FIG. 19B: IL-6, using ELISA analysis (n=3);

FIG. 20 shows a change of body weight during the period of treatment;

FIG. 21A, FIG. 21B, and FIG. 21C show blood chemistry analysis. Serum samples were collected from mice 15 days after treatment. Levels of hepatic enzymes (FIG. 21A) such as aspartate aminotransferase (AST), analine aminotransferase (ALT), and alkaline phosphatase (ALKP); renal function biomarkers (FIG. 21B), including blood urea nitrogen (BUN) and creatinine; and hematological paremeters (FIG. 21C), including white blood cells (WBC), lymphocytes (LYM), granulocytes (GRAN), and monocytes (MONO) were determined for each sample. Each value represents the mean±SD (n=4); and FIG. 22 shows histological examination. Major organs were collected 15 days after injection, and evaluated for potential tissue damages by H&E staining. Representative images (10×) of brain, heart, kidney, liver, lung, and spleen from mice in the control groups (PBS and pSi-PEI/Scr 75 μg) and the treatment groups (pSi-PEI/ATM 75 μg) are shown.

BRIEF DESCRIPTION OF THE DISCLOSED NUCLEIC ACID SEQUENCES

SEQ ID NO:1 is a synthetic oligonucleotide primer useful according to particular aspects of the present disclosure;

SEQ ID NO:2 is a synthetic oligonucleotide primer useful according to particular aspects of the present disclosure;

SEQ ID NO:3 is a synthetic oligonucleotide primer useful according to particular aspects of the present disclosure;

SEQ ID NO:4 is a synthetic oligonucleotide primer useful according to particular aspects of the present disclosure;

SEQ ID NO:5 is a synthetic oligonucleotide primer useful according to particular aspects of the present disclosure;

SEQ ID NO:6 is a synthetic oligonucleotide primer useful according to particular aspects of the present disclosure;

SEQ ID NO:7 is a synthetic oligonucleotide primer useful according to particular aspects of the present disclosure; and SEQ ID NO:8 is a synthetic oligonucleotide primer useful according to particular aspects of the present disclosure.

DESCRIPTION OF ILLUSTRATIVE EMBODIMENTS

Illustrative embodiments of the present disclosure are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would be a routine undertaking for those of ordinary skill in the art having the benefit of this disclosure.

The discovery of RNA interference has opened the door for the development of a new class of cancer therapeutics. Small inhibitory RNA oligonucleotides have been designed to specifically suppress expression of proteins that were traditionally considered non-druggable, and microRNAs are being evaluated to exert broad control of gene expression for inhibition of tumor growth. Since most naked molecules are not optimized for in vivo applications, the gene silencing agents need to be packaged into delivery vehicles in order to reach the target tissues as their destinations. Thus, the selection of the right delivery vehicles serves as a crucial step in the development of cancer therapeutics. The following sections summarize the status of gene silencing agents in breast cancer and recent development of candidate cancer drugs in clinical trials. Nanotechnology-based delivery vectors for the formulation and packaging of gene silencing agents are also described.

Challenges in Breast Cancer Treatment

Breast cancer is the most frequently diagnosed malignancy in women. In 2012, an estimated 229,060 new cases of invasive breast cancer and 39,920 cancer deaths were expected in women in the United States (Cantley et al., 2012). With the availability of modern diagnostic tools and increased use of adjuvant systemic therapies, significant progress has been made on early stage breast cancer treatment, and consequently the overall survival rates in breast cancer patients. However, only marginal improvements have been achieved in patients with relapsed metastatic cancer, making it an urgent medical need to develop new, effective therapeutics to treat late-stage breast cancer.

Small molecule inhibitors targeting selected protein kinases and monoclonal antibodies targeting cell-surface receptors have shown promising results in the fight against cancer, including breast cancer, in the past decade. However, the success stories have been limited to only a handful of drug targets. Many of the key cancer-causing genes are traditionally considered 'nondruggable' (Fauman et al., 2011), and thus not enough effort has been dedicated to these genes. Moreover, tumor heterogeneity and genetic instability make it unlikely that a single target will suffice for long-term treatment of most solid tumors.

Since its discovery, RNA interference has been considered to be capable of rapidly and efficiently knocking down the expression of any gene in any cell type, thus opening a door to treat cancer by targeting every cancer-causing gene (Fire et al., 1998). Recent research in gene silencing agents and their delivery systems has shed light on the potential of these therapeutic agents for cancer treatment.

Gene Silencing Agents in Breast Cancer.

Two classes of gene silencing agents have been the focus of intense study in recent years: small interfering RNA (siRNA) and small non-coding microRNA. The siRNA molecule regulates expression of a specific protein via degradation of the mRNA molecule. It usually demands a perfect match between the siRNA oligo and the corresponding sequence in mRNA. On the other hand, microRNA molecules regulate gene expression via suppression of translation. One microRNA molecule often modulates the expression of a group of genes.

Small Inhibitory RNA.

Although originally discovered as long double-stranded RNA molecules, double-stranded siRNA constructs of 30 nucleotides or less have been the default choice to avoid interferon response from longer molecules (Elbashir et al., 2001). Thousands of siRNA-related research articles have since been published that demonstrate the essential roles of the individual genes in cell growth and viability. Key cancer genes have also been identified through screening of siRNA/small hairpin RNA (shRNA) libraries for cell proliferation and survival (Schlabach et al., 2008). These genes are involved in almost all the important signal transduction pathways that control tumor initiation, progression, metastasis, and tumor angiogenesis. Detailed information on the individual genes has been published elsewhere, and is not the scope of this article. It has been estimated that there are about 80 mutations in an individual breast tumor, of which a dozen are driving mutations (Wood et al., 2007). Adding to the complexity, every cancer patient carries a unique spectrum of gene mutations, making the pool of mutant genes unimaginably large. While the current small molecule cancer drugs can only impact a very small portion of cancer-causing genes, the availability of the specially designed siRNAs targeting the large number of genes makes it possible for personalized treatment of breast cancer based on the genetic and epigenetic changes of every patient.

Genes and pathways that contribute to resistance to current cancer therapy have also been identified. Trastuzumab has been a key drug to treat Her2-positive breast cancer patients, but not everyone who is positive for Her2 responds to the treatment. In a large-scale RNA interference screening with the Her2-overexpressing BT474 breast cancer cell line (Berns et al., 2007), loss of PTEN expression caused resistance to trastuzumab treatment. Since PTEN is a negative regulator of the phosphoinositide 3-kinase (PI3K)/AKT pathway, it is speculated that activation of PI3K signaling confers therapy resistance to trastuzumab. To support this notion, it was found that overexpression of PI3K also caused therapy resistance (Berns et al., 2007). Another application of siRNA is to sensitize chemotherapy by knocking down expression of multidrug resistant genes in breast cancer cells.

microRNA. MicroRNAs can be arbitrarily divided into two groups based on their target genes in breast cancer. The group I micro-RNAs regulate key genes in cancer cell growth and survival. These include let-7, miR-17/20, miR-21, miR-103/107, the miR-200 family and miR-708. One of the first identified microRNAs was let-7. This molecule regulates expression of such important cancer genes as KRAS and MYC (Johnson et al., 2005). Another example is miR-21, which is overexpressed in breast cancer. It modulates the activity of PI3K/AKT and ERK1/2 pathways via control of PTEN expression. Consequently, treatment of MDA-MB-231 human breast cancer cells with a miR-21 antagomir reversed the oncogenic phenotype of the cell line (Han et al., 2012). In contrast to those described above, miR-103/107 exert their global control of gene expression through modulating dicer expression (Martello et al., 2010). Owing to the pivotal role of Dicer in processing and maturation of all non-coding microRNAs, fluctuation of miR-103/107 levels could have a genome-wide impact on gene expression.

Molecules such as miR-205, miR-206, and miR-221/222 represent members of the group II microRNA family.

Besides regulating expression of many other genes, members in this group also affect the expression of breast cancer surface markers such as HER3 and ERα. For example, miR-205 is one of the regulators of HER3 expression (Iorio et al., 2009). Interestingly, a recent report revealed that the expression of miR-205 itself was down-regulated by Her2 (Adachi et al., 2011).

It is noteworthy that expression of one specific gene could be controlled by several microRNA molecules. Both the miR-200 family and miR-205 modulate epithelial-mesenchymal transition through regulating ZEB1 expression, and ERa expression is regulated by miR206 and miR-221/222.

Systemic Delivery of Gene Silencing Agents in Cancer Therapy

Challenges in Delivery of Therapeutic Agents.

Most studies on the biological functions of gene silencing agents have so far been performed using cell-based assays. The excitement and effort in this research field have not been successfully translated into Food and Drug Administration-approved drugs for treatment of human cancers. The fundamental problem with in vivo application of gene silencing agents is the lack of effective carriers for systemic delivery in order to overcome the multiple biological barriers (Ferrari, 2010). Once inside the circulation, the therapeutic agent needs to survive attack from plasma ribonucleases. Without effective protection, most double-stranded RNA oligos are digested within minutes. They will also need to escape elimination by the reticulo-endothelial system (the sinusoids of the liver, the spleen, and the alveolar beds of the lung). Upon reaching the tumor vasculature, the agents will have to fight against the unfavorable tumor interstitial pressure in order to cross the blood vessel wall. Once inside the tumor tissue, they still need to cross the extracellular matrix and bypass the connective tissues before reaching tumor cells. Since the unmodified, double-stranded, RNA oligonucleotides are negatively charged, they cannot cross the cytoplasmic membrane to reach the cytosol where they are active. The default choice to facilitate cell entry of siRNA or microRNA into cells has been to package them in cationic nanoparticles. To date, nanotechnology has played an important role in the design of various forms of carriers for in vivo delivery of gene silencing agents.

Nanotechnology in Breast Cancer Therapy.

Interestingly, nanotechnology has been used in breast cancer therapy for decades. Doxil, the liposomal formulation of doxorubicin, is the first nano-drug approved for breast cancer therapy; doxorubicin is a potent anticancer drug for breast cancer treatment. However, it tends to accumulate in the heart, thus causing severe cardiac side-effects. Nano-formulation of doxorubicin dramatically reduced cardiac side effects (O'Brien et al., 2004) while preserving or even enhancing the therapeutic effect of the active drug (Batist et al., 2001). Abraxane©, (Celgene Corp., Summit, N.J., USA) the nanoparticle albumin-bound paclitaxel, is another success story of nanotechnology in breast cancer therapy. Paclitaxel has been widely used to treat multiple cancer types, including breast cancer. Traditionally, paclitaxel has been formulated in Cremophor EL since the active drug is hydrophobic. However, this solvent itself can cause severe side effects, such as allergic reactions and neutropenia. Packaging of paclitaxel into the 1303 nm albumin-bound formulation allows for a 50% increase in drug dosage as a result of decreased overall toxicity compared to the solvent-based formulation (Gradishar et al., 2005).

Nanotechnology-Based Delivery Systems for Gene Silencing Agents.

Multiple technology platforms have been developed to deliver gene-silencing agents for cancer therapy. The most common approach is to package double-stranded RNA into nanoparticles that are less than 2003 nm in diameter. This approach takes advantage of the enhanced permeability and retention effect of the leaky tumor vasculature (Maeda, 2001). Since the tumor blood vessel endothelium is disorganized with gaps ranging from 100 to 5003 nm at the cell juncture (Baluk et al., 2005), the nanoparticles can easily cross the fenestration to reach tumor interstitium (FIG. 1B). Based on the nature of the packaging material, this group of delivery carriers can be divided into 1) lipid-based, and 2) non lipid-based nanovectors.

The lipid-based nanovectors include liposomes (Fenske et al., 2008), stable nucleic acid lipid particles (SNALPs) (Zimmermann et al., 2006), and lipidoid nanoparticles (Akinc et al., 2008).

Non-lipid-based nanovectors contain chitosan (Kim et al., 2011), poly(amido amine) dendrimers (Monteagudo et al., 2011), polyethylenimines (Cubillos-Ruiz et al., 2009), or other polymeric materials as the building blocks.

Conjugates composed of lipid-polymers or polymer-polymers have also been frequently used for siRNA delivery (Navarro et al., 2012).

Another commonly used siRNA carrier is gold nanoparticles. In addition, nanoparticles free of any added materials except the siRNA building block itself have also been reported (Lee et al., 2012). Depending upon whether there are targeting moieties on the surface of the particles, these delivery carriers can also be divided into active-targeting and passive-targeting vectors.

RNA Delivery by Passive Targeting. siRNA oligonucleotides have taken the lead in reaching clinical trials for cancer therapy. Most of the current candidate drugs are formulated into lipid-based nanovectors without active targeting moieties on the surface. Both TKM-PLK-1 from Tekmira Pharmaceuticals (Burnaby, BC, Canada) and ALN-VSPO2 from Alnylam Pharmaceuticals (Cambridge, Mass., USA) use SNALPs as the delivery vector. These SNALPs consist of the ionizable cationic lipid 1,2-dilinoleyloxy-3-dimethylaminopropane (DLinDMA) as the core lipid component. They have a high siRNA encapsulation capacity, and a small, uniform size.

TKM-PLK-1 consists of a polo-like kinase31 (PLK1)-specific siRNA packaged in SNALPs. PLK1 is involved in cell cycle progression, and targeted delivery of PLK1 siRNA suppresses growth and metastasis of Her2+ breast cancer in orthotopic xenograft models (Yao et al., 2012). ALN-VSP2 is the first product with dual targeting agents, consisting of siRNA oligos specific to the vascular endothelial growth factor (VEGF) and kinesin spindle protein (KSP) (Judge et al., 2009). It is hypothesized that knocking down both genes in the same cancer cells might have an additive or even synergistic effect on cell growth and viability.

New cationic lipid molecules have recently been identified to prepare more effective SNALP for siRNA delivery (Semple et al., 2010). It is anticipated that more gene silencing products based on SNALP will be developed in the coming years. Since SNALP tends to accumulate in the liver, the main indication of these drugs is to treat liver cancer or liver metastasis of other solid cancers.

Atu027 from Silence Therapeutics (London, England) is composed of a protein kinase N3 (PKN3)-specific siRNA in positively-charged liposomes prepared with a mixture of cationic and fusogenic lipids (Santel et al., 2006). PKN3 is a downstream effector of the PI3K pathway, one of the most important pathways in breast cancer biology. Knockdown of PKN3 impairs growth of primary breast and prostate tumor, and blocks tumor metastasis (Unsal-Kacmaz et al., 2012). A phase I trial with advanced solid cancer has been completed with this agent (Strumberg et al., 2012).

siRNA-EphA2-DOPC is formulated by mixing the EphA2 siRNA with the neutral lipid, 1,2-dioleoyl-sn-glycero-3-phosphocholine, in an excess of tbutanol, followed by lyophilization (Landen et al., 2005). EphA2 encodes the ephrin receptor tyrosine kinase that is overexpressed in multiple cancer types, including breast cancer. Blocking EphA2 activity by antibody-drug conjugates, or through knockdown of gene expression inhibits tumor growth (Landen et al., 2005). Additionally, dual targeting of EphA2 and other cancer genes has resulted in enhanced tumor growth inhibition (Shahzad et al., 2009). Although most of the initial studies were focused on ovarian cancer, the disease indication for the current clinical trial includes all solid tumors.

RNA Delivery by Active Targeting.

CALAA-01 from Calando Pharmaceutics (Duarte, Calif., USA) is not only the first siRNA therapeutic in a human cancer clinical trial, but is also the first siRNA-based therapeutic that is formulated with an active targeting mechanism (Davis et al., 2010). This siRNA is specific for the M2-subunit of ribonucleotide reductase (RRM2), and is encapsulated within a cyclodextrin nanoparticle. An affinity moiety of the human transferrin protein targeting ligand is also decorated on the surface of the nanoparticle. It has been well documented that the transferrin receptor protein is overexpressed on the surface of cancer cells, and can thus be used for effective tumor targeting (Bellocq et al., 2003). The 70-nm nanoparticles of CALAA-01 are small enough to cross the fenestration following systemic administration. Once inside the tumor tissue, the targeting moiety directs the nanoparticles to tumor cells that express the transferrin receptor protein on their surfaces.

The first-in-human cancer trial has demonstrated accumulation of RRM2. siRNA in tumor tissues and gene-specific knockdown of expression (Davis et al., 2010). Although the clinical trial was carried out with melanoma patients, there is no reason to believe that CALAA-01 cannot be used to treat other cancer types such as breast cancer given that RRM2 controls DNA synthesis and damage repair during the cell cycle.

Multistage Vectors for RNA Delivery.

The multistage vector (MSV) delivery system described herein was designed to maximize delivery of therapeutic agents to tumor cells through sequential negotiation of various biological barriers (Ferrari, 2010). The system consists of a first-stage, nanoporous silicon microparticle and a second-stage, liposomal particle, which is loaded into the nanopores of the first-stage microparticle. For delivery of gene silencing agents, double-stranded RNA molecules are packaged into 30- to 40-nm liposomes that are then loaded into the 60- to 80-nm pores of the nanoporous silicon microparticle (Shen et al., 2013; Tanaka et al., 2010). Once inside the bloodstream, the first-stage microparticles travel with the blood flow and settle at tumor vasculature, where the liposomal siRNAs are released therefrom. The rate of siRNA release is determined by the diameter of the nanopores, the size of the liposome, and the rate of silicon degradation.

The first-stage microparticles are designed based on size, shape, and surface chemical properties to achieve maximal tumor enrichment. Hemispherical and discoidal-shaped particles are more effective in adhesion to tumor vasculature than particles with other shapes such as spherical and cylindrical (van de Ven et al., 2011). The size of the microparticle is a major determinant of particle accumulation. For example, 1-μm discoidal particles accumulate more readily in melanoma tissue than do sub-micrometer particles, or larger (e.g., 3.2-μm) particles having the same shape (van de Ven et al., 2011). Interestingly, the size of the particle also affects the efficiency of affinity targeting. Surface conjugation of an RDG targeting moiety also significantly enhances tumor accumulation of sub-micrometer particles, but has minimum impact once the size exceeds ~1 μm (van de Ven et al., 2011). Surface chemical modification not only affects protein binding, but also determines the loading efficiency of the second-stage liposomal particles into the microparticle nanopores. Since the liposomal siRNA carries a negative Zeta potential, the surface of the nanopores is modified with polyamine to facilitate loading of nanoparticles (Godin et al., 2011).

This system has been successfully applied to deliver siRNA for cancer treatment with experimental tumor models (Shen et al., 2013; Tanaka et al., 2010; Xu et al., 2013). Treatment of tumor mice with one dose of MSV/EphA2 siRNA resulted in knockdown of EphA2 expression for up to 3 weeks due to sustained release of liposomal siRNA (Tanaka et al., 2010). It is suspected that the MSV/siRNA in tumor vasculature and other organs serves as a depot for constant supply of the gene-silencing agent (Ferrari, 2010). Xu and colleagues (Xu et al., 2013) recently treated an orthotopic model of MDA-MB-231 primary tumor with siRNA targeting the ATM gene delivered in the MSV. Effective knockdown of ATM expression resulted in dramatic inhibition of tumor growth. Since efficacy and toxicity constitute the two major aspects of siRNA therapeutics, they also performed studies to systematically evaluate toxicity that might have been caused by MSV/ATM. After careful evaluation, it was determined that no acute immunotoxicity or sub-acute toxicity was associated with administration of MSV/ATM siRNA, which paved the pathway for development of MSV/ATM siRNA as a therapeutic agent for breast cancer (Xu et al., 2013).

Overcoming Therapy Resistance.

One area of siRNA therapeutics that has shown great promise is sensitization to chemotherapy. Overexpression of multidrug-resistant genes has been attributed to chemoresistance. MacDiarmid and colleagues used a short hairpin RNA to knock down expression of the MDR1 gene in vivo, and subsequently treated murine models of human cancers with chemotherapy drugs (MacDiarmid et al., 2009). Navarro and colleagues synthesized a DOPE-PEI (dioleoylphosphatidylethanolamine-polyethylenimine) conjugate to enhance transfection capacity of the low molecular weight PEI (Navarro et al., 2012). They used the conjugate to deliver MDR1-specific siRNA, and demonstrated sensitization to doxorubicin treatment of the otherwise resistant MCF-7 cells. The inventors and their colleagues have demonstrated sensitization of docetaxel treatment by EphA2 siRNA in a murine model of human ovarian cancer (Shen et al., 2013).

Another area that has gained increasing attention in breast cancer therapy is the target of cancer stem cells. These cells are resistant to conventional chemotherapy, and are the lethal seeds for tumor recurrence and local and distant metastasis (Li et al., 2008). By comparing differential expression between the bulk of cancer cells and cancer stem cells, a group of candidate genes have been identified that may be essential for growth and survival of cancer stem cells (Dave et al., 2012). Recent studies with MSV-vectored delivery of cancer stem cell-gene-specific siRNA oligonucleotides have facilitated the development of new cancer therapeutics, and these agents are expected to play a significant role in the fight against human breast cancer.

Gene silencing agents will also continue to contribute significantly to breast oncology treatment. Recent advances in RNA interference have resulted in the development of multiple candidate siRNA therapeutics being evaluated in the clinic. It is expected that non-coding microRNAs will also follow suit, and be added to the candidate drug list soon.

On the other hand, development of delivery vectors for most solid tumor types has lagged, and there remain few options available for delivering siRNA/microRNA-based therapeutics to primary breast cancer tumors. It is ever harder to deliver therapeutics to distant organs of breast cancer metastasis, such as the brain and/or bone. The present invention expands on the design and development of tissue-specific and tumor-type-specific delivery systems to facilitate a broader use of siRNAs and microRNAs in breast cancer therapy.

In particular, the present invention describes the design and development of a new platform for in vivo delivery of therapeutic compounds, such as siRNA and microRNA. It has shown facile application to the treatment of human conditions, such as cancer and cardiovascular disease. An exemplary murine cancer model was used to demonstrate its effectiveness in vivo, and its use can likely be expanded to organ transplant, tissue engineering, and other medical areas.

Polycation materials, such as poly-arginine (poly-Arg), poly-lysine (poly-Lys), chitosan, dendrimer, polyethylenimine (PEI), have a high binding capacity to the negatively-charged siRNA, or microRNA molecules. Nanoporous silicon particles can be tailored with the right size and shape to accumulate into the vasculature of the tissue/organ of interest, such as tumor tissues. In the present invention, polycations have been chemically conjugated inside the nanopores of porous silicon by covalent bonds. These polycation-functionalized nanoporous silicon (PCPS) are then loaded with one or more therapeutic agents, such as an siRNA, a microRNA, or a combination thereof. High-capacity loading is achieved due to the interaction between the positively-charged polycations, and the negatively-charged siRNA or microRNA. Formation of the complex protects the RNA molecules from degradation by nucleases once they are delivered inside the body. Upon systemic delivery, the RNA-loaded PCPS particles have been shown to travel in the circulatory system, cross multiple biological barriers, and accumulate significantly in the tumor vasculature. When the porous silicon is degraded by the cell, the RNA-bound polycation is released from confinement in the nanopores, and nanoparticles are formed. These siRNA/microRNA-packaged nanoparticles then enter the tumor cells, and exert their biological function.

In the first example that follows, PEI molecules were conjugated into porous silicon. In the second example, ArqPEI was used as the polycation. The results obtained from these two studies led to the following conclusions:

1) Polycation is conjugated to nanoporous silicon by covalent linkers;

2) PCPS has a high binding capacity to siRNA/microRNA;

3) The polycation/RNA complex was confined inside the nanopores of porous silicon, and thereby cannot form nanoparticles there;

4) When porous silicon is degraded, the polycation/RNA complex is released from confinement, and forms nanoparticles. The average diameter of the nanoparticles is bigger than the diameter of the nanopores;

5) The polycation/RNA nanoparticles enter cells via vesicular transport, and the RNA molecules escape endosomes to enter the cytosol for biological function;

6) Excellent knockdown of gene expression by PCPS/siRNA in cell culture was demonstrated;

7) Good accumulation of PCPS/siRNA in tumor tissues when tested with murine model of MDA-MB-231 human breast cancer, and good knockdown of gene expression in tumor tissues were achieved; and 8) No acute or sub-acute toxicity was found with the PCPS delivery system upon porous silicon degradation.

EXEMPLARY DEFINITIONS

In accordance with the present invention, polynucleotides, nucleic acid segments, nucleic acid sequences, and the like, include, but are not limited to, DNAs (including and not limited to genomic or extragenomic DNAs), genes, peptide nucleic acids (PNAs) RNAs (including, but not limited to, rRNAs, mRNAs and tRNAs), nucleosides, and suitable nucleic acid segments either obtained from natural sources, chemically synthesized, modified, or otherwise prepared or synthesized in whole or in part by the hand of man.

Unless defined otherwise, all technical and scientific terms used herein have the same meaning as commonly understood by one of ordinary skill in the art to which this invention belongs. Although any methods and compositions similar or equivalent to those described herein can be used in the practice or testing of the present invention, the preferred methods and compositions are described herein. For purposes of the present invention, the following terms are defined below:

In accordance with long standing patent law convention, the words "a" and "an" when used in this application, including the claims, denote "one or more."

As used herein, an "antigenic polypeptide" or an "immunogenic polypeptide" is a polypeptide which, when introduced into a vertebrate, reacts with the vertebrate's immune system molecules, i.e., is antigenic, and/or induces an immune response in the vertebrate, i.e., is immunogenic.

The terms "about" and "approximately" as used herein, are interchangeable, and should generally be understood to refer to a range of numbers around a given number, as well as to all numbers in a recited range of numbers (e.g., "about 5 to 15" means "about 5 to about 15" unless otherwise stated). Moreover, all numerical ranges herein should be understood to include each whole integer within the range.

Biocompatible" refers to a material that, when exposed to living cells, will support an appropriate cellular activity of the cells without causing an undesirable effect in the cells, such as a change in a living cycle of the cells, a change in a proliferation rate of the cells, or a cytotoxic effect.

As used herein, the term "buffer" includes one or more compositions, or aqueous solutions thereof, that resist fluctuation in the pH when an acid or an alkali is added to the solution or composition that includes the buffer. This resistance to pH change is due to the buffering properties of such solutions, and may be a function of one or more specific compounds included in the composition. Thus, solutions or other compositions exhibiting buffering activity are referred to as buffers or buffer solutions. Buffers generally do not have an unlimited ability to maintain the pH of a solution or composition; rather, they are typically able to maintain the pH within certain ranges, for example from a pH of about 5 to 7.

As used herein, the term "carrier" is intended to include any solvent(s), dispersion medium, coating(s), diluent(s), buffer(s), isotonic agent(s), solution(s), suspension(s), colloid(s), inert(s) or such like, or a combination thereof, that is pharmaceutically acceptable for administration to the relevant animal. The use of one or more delivery vehicles for chemical compounds in general, and chemotherapeutics in particular, is well known to those of ordinary skill in the pharmaceutical arts. Except insofar as any conventional media or agent is incompatible with the active ingredient, its use in the diagnostic, prophylactic, and therapeutic compositions is contemplated. One or more supplementary active ingredient(s) may also be incorporated into, or administered in association with, one or more of the disclosed chemotherapeutic compositions.

As used herein, the term "DNA segment" refers to a DNA molecule that has been isolated free of total genomic DNA of a particular species. Therefore, a DNA segment obtained from a biological sample using one of the compositions disclosed herein refers to one or more DNA segments that have been isolated away from, or purified free from, total genomic DNA of the particular species from which they are obtained. Included within the term "DNA segment," are DNA segments and smaller fragments of such segments, as well as recombinant vectors, including, for example, plasmids, cosmids, phage, viruses, and the like.

The term "effective amount," as used herein, refers to an amount that is capable of treating or ameliorating a disease or condition or otherwise capable of producing an intended therapeutic effect.

The term "for example" or "e.g.," as used herein, is used merely by way of example, without limitation intended, and should not be construed as referring only those items explicitly enumerated in the specification.

As used herein, the terms "engineered" and "recombinant" cells are intended to refer to a cell into which an exogenous polynucleotide segment (such as DNA segment that leads to the transcription of a biologically active molecule) has been introduced. Therefore, engineered cells are distinguishable from naturally occurring cells, which do not contain a recombinantly-introduced exogenous DNA segment. Engineered cells are, therefore, cells that comprise at least one or more heterologous polynucleotide segments introduced through the hand of man.

As used herein, the term "epitope" refers to that portion of a given immunogenic substance that is the target of, i.e., is bound by, an antibody or cell-surface receptor of a host immune system that has mounted an immune response to the given immunogenic substance as determined by any method known in the art. Further, an epitope may be defined as a portion of an immunogenic substance that elicits an antibody response or induces a T-cell response in an animal, as determined by any method available in the art (see, for example, Geysen et al., 1984). An epitope can be a portion of any immunogenic substance, such as a protein, polynucleotide, polysaccharide, an organic or inorganic chemical, or any combination thereof. The term "epitope" may also be used interchangeably with "antigenic determinant" or "antigenic determinant site."

As used herein, the term "homology" refers to a degree of complementarity between two polynucleotide or polypeptide sequences. The word "identity" may substitute for the word "homology" when a first nucleic acid or amino acid sequence has the exact same primary sequence as a second nucleic acid or amino acid sequence. Sequence homology and sequence identity can be determined by analyzing two or more sequences using algorithms and computer programs known in the art. Such methods may be used to assess whether a given sequence is identical or homologous to another selected sequence.

As used herein, "homologous" means, when referring to polypeptides or polynucleotides, sequences that have the same essential structure, despite arising from different origins. Typically, homologous proteins are derived from closely related genetic sequences, or genes. By contrast, an "analogous" polypeptide is one that shares the same function with a polypeptide from a different species or organism, but has a significantly different form to accomplish that function. Analogous proteins typically derive from genes that are not closely related.

The terms "identical" or percent "identity," in the context of two or more peptide sequences, refer to two or more sequences or subsequences that are the same or have a specified percentage of amino acid residues that are the same, when compared and aligned for maximum correspondence over a comparison window, as measured using a sequence comparison algorithm or by manual alignment and visual inspection.

The phrases "isolated" or "biologically pure" refer to material that is substantially, or essentially, free from components that normally accompany the material as it is found in its native state. Thus, an isolated peptide in accordance with the invention preferably does not contain materials normally associated with that peptide in its in situ environment.

As used herein, the term "kit" may be used to describe variations of the portable, self-contained enclosure that includes at least one set of reagents, components, or pharmaceutically-formulated compositions to conduct one or more of the diagnostic methods of the invention.

"Link" or "join" refers to any method known in the art for functionally connecting peptides, including, without limitation, recombinant fusion, covalent bonding, disulfide bonding, ionic bonding, hydrogen bonding, electrostatic bonding, and such like.

As used herein, the phrase "in need of treatment" refers to a judgment made by a caregiver such as a physician or veterinarian that a patient requires (or will benefit in one or more ways) from treatment. Such judgment may made based on a variety of factors that are in the realm of a caregiver's expertise, and may include the knowledge that the patient is ill as the result of a disease state that is treatable by one or more compound or pharmaceutical compositions such as those set forth herein.

"Microparticle" means a particle having a maximum characteristic size from 1 micron to 1000 microns or from 1 micron to 100 microns. Preferably, the porous particle of this disclosure should have a relatively high porosity to enable loading of the polymeric-active agent conjugate in the pores of the porous particles. Optionally, the porous particles of the present disclosure may be coated with a targeting moiety. Such embodiments may be useful for targeted delivery of the active compound to the desired disease site.

"Nanoparticle" means a particle having a maximum characteristic size of less than 1 micron. Preferably, the polymeric-active agent conjugate of this disclosure forms nanoparticles upon release from the porous silicon particle upon physiological degradation of the porous particle, and upon coming in contact with an aqueous environment.

As used herein, the term "nucleic acid" includes one or more types of: polydeoxyribonucleotides (containing 2-deoxy-D-ribose), polyribonucleotides (containing D-ribose), and any other type of polynucleotide that is an N-glycoside of a purine or pyrimidine base, or modified purine or pyrimidine bases (including abasic sites). The term "nucleic acid," as used herein, also includes polymers of ribonucleosides or deoxyribonucleosides that are covalently bonded, typically by phosphodiester linkages between subunits, but in some cases by phosphorothioates, methylphosphonates, and the like. "Nucleic acids" include single- and double-stranded DNA, as well as single- and double-stranded RNA. Exemplary nucleic acids include, without limitation, gDNA; hnRNA; mRNA; rRNA, tRNA, micro RNA (miRNA), small interfering RNA (siRNA), small nucleolar RNA (snORNA), small nuclear RNA (snRNA), and small temporal RNA (stRNA), and the like, and any combination thereof.

The term "naturally occurring" as used herein as applied to an object refers to the fact that an object can be found in nature. For example, a polypeptide or polynucleotide sequence that is present in an organism (including viruses) that can be isolated from a source in nature and which has not been intentionally modified by the hand of man in a laboratory is naturally-occurring. As used herein, laboratory strains of rodents that may have been selectively bred according to classical genetics are considered naturally occurring animals.

The term "operably linked," as used herein, refers to that the nucleic acid sequences being linked are typically contiguous, or substantially contiguous, and, where necessary to join two protein coding regions, contiguous and in reading frame. However, since enhancers generally function when separated from the promoter by several kilobases, and intronic sequences may be of variable lengths; some polynucleotide elements may be operably linked, but not contiguous.

As used herein, the term "patient" (also interchangeably referred to as "host" or "subject") refers to any host that can receive one or more of the pharmaceutical compositions disclosed herein. Preferably, the subject is a vertebrate animal, which is intended to denote any animal species (and preferably, a mammalian species such as a human being). In certain embodiments, a "patient" refers to any animal host including without limitation any mammalian host. Preferably, the term refers to any mammalian host, the latter including but not limited to, human and non-human primates, bovines, canines, caprines, cavines, corvines, epines, equines, felines, hircines, lapines, leporines, lupines, murines, ovines, porcines, ranines, racines, vulpines, and the like, including livestock, zoological specimens, exotics, as well as companion animals, pets, and any animal under the care of a veterinary practitioner. A patient can be of any age at which the patient is able to respond to inoculation with the present vaccine by generating an immune response. In particular embodiments, the mammalian patient is preferably human.

The phrase "pharmaceutically-acceptable" refers to molecular entities and compositions that preferably do not produce an allergic or similar untoward reaction when administered to a mammal, and in particular, when administered to a human. As used herein, "pharmaceutically acceptable salt" refers to a salt that preferably retains the desired biological activity of the parent compound and does not impart any undesired toxicological effects. Examples of such salts include, without limitation, acid addition salts formed with inorganic acids (e.g., hydrochloric acid, hydrobromic acid, sulfuric acid, phosphoric acid, nitric acid, and the like); and salts formed with organic acids including, without limitation, acetic acid, oxalic acid, tartaric acid, succinic acid, maleic acid, fumaric acid, gluconic acid, citric acid, malic acid, ascorbic acid, benzoic acid, tannic acid, pamoic (embonic) acid, alginic acid, naphthoic acid, polyglutamic acid, naphthalenesulfonic acids, naphthalenedisulfonic acids, polygalacturonic acid; salts with polyvalent metal cations such as zinc, calcium, bismuth, barium, magnesium, aluminum, copper, cobalt, nickel, cadmium, and the like; salts formed with an organic cation formed from N,N'-dibenzylethylenediamine or ethylenediamine; and combinations thereof.

As used herein, the term "polypeptide" is intended to encompass a singular "polypeptide" as well as plural "polypeptides," and includes any chain or chains of two or more amino acids. Thus, as used herein, terms including, but not limited to "peptide," "dipeptide," "tripeptide," "protein," "enzyme," "amino acid chain," and "contiguous amino acid sequence" are all encompassed within the definition of a "polypeptide," and the term "polypeptide" can be used instead of, or interchangeably with, any of these terms. The term further includes polypeptides that have undergone one or more post-translational modification(s), including for example, but not limited to, glycosylation, acetylation, phosphorylation, amidation, derivatization, proteolytic cleavage, post-translation processing, or modification by inclusion of one or more non-naturally occurring amino acids. Conventional nomenclature exists in the art for polynucleotide and polypeptide structures. For example, one-letter and three-letter abbreviations are widely employed to describe amino acids: Alanine (A; Ala), Arginine (R; Arg), Asparagine (N; Asn), Aspartic Acid (D; Asp), Cysteine (C; Cys), Glutamine (Q; Gln), Glutamic Acid (E; Glu), Glycine (G; Gly), Histidine (H; His), Isoleucine (I; Leu), Methionine (M; Met), Phenylalanine (F; Phe), Proline (P; Pro), Serine (S; Ser), Threonine (T; Thr), Tryptophan (W; Trp), Tyrosine (Y; Tyr), Valine (V; Val), and Lysine (K; Lys). Amino acid residues described herein are preferred to be in the "L" isomeric form. However, residues in the "D" isomeric form may be substituted for any L-amino acid residue provided the desired properties of the polypeptide are retained.

"Protein" is used herein interchangeably with "peptide" and "polypeptide," and includes both peptides and polypeptides produced synthetically, recombinantly, or in vitro and peptides and polypeptides expressed in vivo after nucleic acid sequences are administered into a host animal or human subject. The term "polypeptide" is preferably intended to refer to any amino acid chain length, including those of short peptides from about 2 to about 20 amino acid residues in length, oligopeptides from about 10 to about 100 amino acid residues in length, and longer polypeptides including from about 100 amino acid residues or more in length. Furthermore, the term is also intended to include enzymes, i.e., functional biomolecules including at least one amino acid polymer. Polypeptides and proteins of the present invention also include polypeptides and proteins that are or have been post-translationally modified, and include any sugar or other derivative(s) or conjugate(s) added to the backbone amino acid chain.

The term "promoter," as used herein refers to a region or regions of a nucleic acid sequence that regulates transcription.

As used herein, the term "substantially free" or "essentially free" in connection with the amount of a component preferably refers to a composition that contains less than about 10 weight percent, preferably less than about 5 weight percent, and more preferably less than about 1 weight percent of a compound. In preferred embodiments, these terms refer to less than about 0.5 weight percent, less than about 0.1 weight percent, or less than about 0.01 weight percent.

The term "pharmaceutically acceptable salt" as used herein refers to a compound of the present disclosure derived from pharmaceutically acceptable bases, inorganic or organic acids. Examples of suitable acids include, but are not limited to, hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, formic, benzoic, malonic, naphthalene-2-sulfonic, trifluoroacetic and benzenesulfonic acids. Salts derived from appropriate bases include, but are not limited to, alkali such as sodium and ammonia.

As used herein, the terms "prevent," "preventing," "prevention," "suppress," "suppressing," and "suppression" as used herein refer to administering a compound either alone or as contained in a pharmaceutical composition prior to the onset of clinical symptoms of a disease state so as to prevent any symptom, aspect or characteristic of the disease state. Such preventing and suppressing need not be absolute to be deemed medically useful.

"Purified," as used herein, means separated from many other compounds or entities. A compound or entity may be partially purified, substantially purified, or pure. A compound or entity is considered pure when it is removed from substantially all other compounds or entities, i.e., is preferably at least about 90%, more preferably at least about 91%, 92%, 93%, 94%, 95%, 96%, 97%, 98%, 99%, or greater than 99% pure. A partially or substantially purified compound or entity may be removed from at least 50%, at least 60%, at least 70%, or at least 80% of the material with which it is naturally found, e.g., cellular material such as cellular proteins and/or nucleic acids.

The term "regulatory element," as used herein, refers to a region or regions of a nucleic acid sequence that regulates transcription. Exemplary regulatory elements include, but are not limited to, enhancers, post-transcriptional elements, transcriptional control sequences, and such like.

The term "RNA segment," as used herein, refers to an RNA molecule that has been isolated free of total cellular RNA of a particular species. Therefore, RNA segments can refer to one or more RNA segments (either of native or synthetic origin) that have been isolated away from, or purified free from, other RNAs. Included within the term "RNA segment," are RNA segments and smaller fragments of such segments.

As used herein, the term "structural gene" is intended to generally describe a polynucleotide, such as a gene, that is expressed to produce an encoded peptide, polypeptide, protein, ribozyme, catalytic RNA molecule, or antisense molecule.

The term "subject," as used herein, describes an organism, including mammals such as primates, to which treatment with the compositions according to the present invention can be provided. Mammalian species that can benefit from the disclosed methods of treatment include, but are not limited to, humans, non-human primates such as apes; chimpanzees; monkeys, and orangutans, domesticated animals, including dogs and cats, as well as livestock such as horses, cattle, pigs, sheep, and goats, or other mammalian species including, without limitation, mice, rats, guinea pigs, rabbits, hamsters, and the like.

As used herein, the term "substantially free" or "essentially free," in connection with the amount of a component, preferably refers to a composition that contains less than about 10 weight percent, preferably less than about 5 weight percent, and more preferably less than about 1 weight percent of a compound. In preferred embodiments, these terms refer to less than about 0.5 weight percent, less than about 0.1 weight percent, or less than about 0.01 weight percent.

The term "sequence," when referring to amino acids, relates to all or a portion of the linear N-terminal to C-terminal order of amino acids within a given amino acid chain, e.g., polypeptide or protein; "subsequence" means any consecutive stretch of amino acids within a sequence, e.g., at least 3 consecutive amino acids within a given protein or polypeptide sequence. With reference to nucleotide chains, "sequence" and "subsequence" have similar meanings relating to the 5' to 3' order of nucleotides.

The term "a sequence essentially as set forth in SEQ ID NO:X" means that the sequence substantially corresponds to a portion of SEQ ID NO:X and has relatively few amino acids (or nucleotides in the case of polynucleotide sequences) that are not identical to, or a biologically-functional equivalent of, the amino acids (or nucleic acids) of SEQ ID NO:X. The term "biologically-functional equivalent" is well understood in the art, and is further defined in detail herein. Accordingly, sequences that have about 85% to about 90%; or more preferably, about 91% to about 95%; or even more preferably, about 96% to about 99%; of amino acids that are identical or functionally-equivalent to one or more of the amino acid sequences provided herein are particularly contemplated to be useful in the practice of the invention and in the detection of pathogen-specific biomarkers from one or more biological samples or specimens.

Suitable standard hybridization conditions for the present invention include, for example, hybridization in 50% formamide, 5×Denhardt's solution, 5×SSC, 25 mM sodium phosphate, 0.1% SDS and 100 μg/mL of denatured salmon sperm DNA at 42° C. for 16 hr followed by 1 hr sequential washes with 0.1×SSC, 0.1% SDS solution at 60° C. to remove the desired amount of background signal. Lower stringency hybridization conditions for the present invention include, for example, hybridization in 35% formamide, 5×Denhardt's solution, 5×SSC, 25 mM sodium phosphate, 0.1% SDS and 100 μg/mL denatured salmon sperm DNA or *E. coli* DNA at 42° C. for 16 hr followed by sequential washes with 0.8×SSC, 0.1% SDS at 55° C. Those of skill in the art will recognize that conditions can be readily adjusted to obtain the desired level of stringency.

Naturally, the present invention also encompasses nucleic acid segments that are complementary, essentially complementary, and/or substantially complementary to at least one or more of the specific nucleotide sequences specifically set forth herein. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to one or more of the specific nucleic acid segments disclosed herein under relatively stringent conditions such as those described immediately above.

As described above, the probes and primers of the present invention may be of any length. By assigning numeric values to a sequence, for example, the first residue is 1, the second residue is 2, etc., an algorithm defining all probes or primers contained within a given sequence can be proposed:

n to n+y, where n is an integer from 1 to the last number of the sequence, and y is the length of the probe or primer minus one, where n+y does not exceed the last number of the sequence. Thus, for a 25-basepair probe or primer (i.e., a "25-mer"), the collection of probes or primers correspond to bases 1 to 25, bases 2 to 26, bases 3 to 27, bases 4 to 28, and so on over the entire length of the sequence. Similarly, for a 35-basepair probe or primer (i.e., a "35-mer"), exemplary primer or probe sequence include, without limitation, sequences corresponding to bases 1 to 35, bases 2 to 36, bases 3 to 37, bases 4 to 38, and so on over the entire length of the sequence. Likewise, for 40-mers, such probes or primers may correspond to the nucleotides from the first basepair to by 40, from the second by of the sequence to by 41, from the third by to by 42, and so forth, while for 50-mers, such probes or primers may correspond to a nucleotide sequence extending from by 1 to by 50, from by 2 to by 51, from by 3 to by 52, from by 4 to by 53, and so forth.

The terms "substantially corresponds to," "substantially homologous," or "substantial identity," as used herein, denote a characteristic of a nucleic acid or an amino acid sequence, wherein a selected nucleic acid or amino acid sequence has at least about 70 or about 75 percent sequence identity as compared to a selected reference nucleic acid or amino acid sequence. More typically, the selected sequence and the reference sequence will have at least about 76, 77, 78, 79, 80, 81, 82, 83, 84 or even 85 percent sequence identity, and more preferably, at least about 86, 87, 88, 89, 90, 91, 92, 93, 94, or 95 percent sequence identity. More preferably still, highly homologous sequences often share greater than at least about 96, 97, 98, or 99 percent sequence identity between the selected sequence and the reference sequence to which it was compared.

As used herein, the term "substantially homologous" encompasses sequences that are similar to the identified sequences such that antibodies raised against peptides having the identified sequences will specifically bind to peptides possessing the "substantially homologous" amino acid sequence. In some variations, the amount of detectable antibodies induced by the homologous sequence is identical to the amount of detectable antibodies induced by the identified sequence. In other variations, the amounts of detectable antibodies induced are substantially similar, thereby providing immunogenic properties. For example, "substantially homologous" can refer to at least about 75%, preferably at least about 80%, and more preferably at least about 85% or at least about 90% identity, and even more preferably at least about 95%, more preferably at least about 97% identical, more preferably at least about 98% identical, more preferably at least about 99% identical, and even more preferably still, at least substantially or entirely 100% identical (i.e., "invariant").

The percentage of sequence identity may be calculated over the entire length of the sequences to be compared, or may be calculated by excluding small deletions or additions which total less than about 25 percent or so of the chosen reference sequence. The reference sequence may be a subset of a larger sequence, such as a portion of a gene or flanking sequence, or a repetitive portion of a chromosome. However, in the case of sequence homology of two or more polynucleotide sequences, the reference sequence will typically comprise at least about 18-25 nucleotides, more typically at least about 26 to 35 nucleotides, and even more typically at least about 40, 50, 60, 70, 80, 90, or even 100 or so nucleotides.

When highly-homologous fragments are desired, the extent of percent identity between the two sequences will be at least about 80%, preferably at least about 85%, and more preferably about 90% or 95% or higher, as readily determined by one or more of the sequence comparison algorithms well-known to those of skill in the art, such as e.g., the FASTA program analysis described by Pearson and Lipman (1988).

"Targeting moiety" is any factor that may facilitate targeting of a specific site by a particle. For example, the targeting moiety may be a chemical targeting moiety, a physical targeting moiety, a geometrical targeting moiety, or a combination thereof. The chemical targeting moiety may be a chemical group or molecule on a surface of the particle; the physical targeting moiety may be a specific physical property of the particle, such as a surface such or hydrophobicity; the geometrical targeting moiety includes a size and a shape of the particle. Further, the chemical targeting moiety may be a dendrimer, an antibody, an aptamer, which may be a thioaptamer, a ligand, an antibody, or a biomolecule that binds a particular receptor on the targeted site. A physical targeting moiety may be a surface charge. The charge may be introduced during the fabrication of the particle by using a chemical treatment such as a specific wash. For example, immersion of porous silica or oxidized silicon surface into water may lead to an acquisition of a negative charge on the surface. The surface charge may be also provided by an additional layer or by chemical chains, such as polymer chains, on the surface of the particle. For example, polyethylene glycol chains may be a source of a negative charge on the surface. Polyethylene glycol chains may be coated or covalently coupled to the surface using methods known to those of ordinary skill in the art.

The expression "zero-order or near-zero-order" as applied to the release kinetics of the active agent delivery composition disclosed herein is intended to include a rate of release of the active agent in a controlled manner over a therapeutically practical time period following administration of the composition, such that a therapeutically effective plasma concentration of the active agent is achieved.

The term "therapeutically practical time period" means a time period necessary for the active agent to be therapeutically effective. The term "therapeutically effective" refers to reduction in severity and/or frequency of symptoms, elimination of symptoms and/or underlying cause, prevention of the occurrence of symptoms and/or their underlying cause, and improvement or remediation of damage.

As used herein, a "transcription factor recognition site" and a "transcription factor binding site" refer to a polynucleotide sequence(s) or sequence motif(s), which are identified as being sites for the sequence-specific interaction of one or more transcription factors, frequently taking the form of direct protein-DNA binding. Typically, transcription factor binding sites can be identified by DNA footprinting, gel mobility shift assays, and the like, and/or can be predicted on the basis of known consensus sequence motifs, or by other methods known to those of skill in the art.

"Transcriptional unit" refers to a polynucleotide sequence that comprises at least a first structural gene operably linked to at least a first cis-acting promoter sequence and optionally linked operably to one or more other cis-acting nucleic acid sequences necessary for efficient transcription of the structural gene sequences, and at least a first distal regulatory element as may be required for the appropriate tissue-specific and developmental transcription of the structural gene sequence operably positioned under the control of the promoter and/or enhancer elements, as well as any additional cis sequences that are necessary for efficient transcription and translation (e.g., polyadenylation site(s), mRNA stability controlling sequence(s), etc.

The term "substantially complementary," when used to define either amino acid or nucleic acid sequences, means that a particular subject sequence, for example, an oligonucleotide sequence, is substantially complementary to all or a portion of the selected sequence, and thus will specifically bind to a portion of an mRNA encoding the selected sequence. As such, typically the sequences will be highly complementary to the mRNA "target" sequence, and will have no more than about 1, about 2, about 3, about 4, about 5, about 6, about 7, about 8, about 9, or about 10 or so base mismatches throughout the complementary portion of the sequence. In many instances, it may be desirable for the sequences to be exact matches, i.e., be completely complementary to the sequence to which the oligonucleotide specifically binds, and therefore have zero mismatches along the complementary stretch. As such, highly complementary sequences will typically bind quite specifically to the target sequence region of the mRNA and will therefore be highly efficient in reducing, and/or even inhibiting the translation of the target mRNA sequence into polypeptide product.

Substantially complementary nucleic acid sequences will be greater than about 80 percent complementary (or "% exact-match") to a corresponding nucleic acid target sequence to which the nucleic acid specifically binds, and will, more preferably be greater than about 85 percent complementary to the corresponding target sequence to which the nucleic acid specifically binds. In certain aspects, as described above, it will be desirable to have even more substantially complementary nucleic acid sequences for use in the practice of the invention, and in such instances, the nucleic acid sequences will be greater than about 90 percent complementary to the corresponding target sequence to which the nucleic acid specifically binds, and may in certain embodiments be greater than about 95 percent complementary to the corresponding target sequence to which the nucleic acid specifically binds, and even up to and including about 96%, about 97%, about 98%, about 99%, and even about 100% exact match complementary to all or a portion of the target sequence to which the designed nucleic acid specifically binds.

Percent similarity or percent complementary of any of the disclosed nucleic acid sequences may be determined, for example, by comparing sequence information using the GAP computer program, version 6.0, available from the University of Wisconsin Genetics Computer Group (UWGCG). The GAP program utilizes the alignment method of Needleman and Wunsch (1970). Briefly, the GAP program defines similarity as the number of aligned symbols (i.e., nucleotides or amino acids) that are similar, divided by the total number of symbols in the shorter of the two sequences. The preferred default parameters for the GAP program include: (1) a unary comparison matrix (containing a value of 1 for identities and 0 for non-identities) for nucleotides, and the weighted comparison matrix of Gribskov and Burgess (1986), (2) a penalty of 3.0 for each gap and an additional 0.10 penalty for each symbol in each gap; and (3) no penalty for end gaps.

As used herein, the term "transformed cell" is intended to mean a host cell whose nucleic acid complement has been altered by the introduction of one or more exogenous polynucleotides into that cell.

As used herein, the term "transformation" is intended to generally describe a process of introducing an exogenous polynucleotide sequence (e.g., a viral vector, a plasmid, or a recombinant DNA or RNA molecule) into a host cell or protoplast in which the exogenous polynucleotide is incorporated into at least a first chromosome or is capable of autonomous replication within the transformed host cell. Transfection, electroporation, and "naked" nucleic acid uptake all represent examples of techniques used to transform a host cell with one or more polynucleotides.

In certain embodiments, it will be advantageous to employ one or more nucleic acid segments of the present invention in combination with an appropriate detectable marker (i.e., a "label,"), such as in the case of employing labeled polynucleotide probes in determining the presence of a given target sequence in a hybridization assay. A wide variety of appropriate indicator compounds and compositions are known in the art for labeling oligonucleotide probes, including, without limitation, fluorescent, radioactive, enzymatic or other ligands, such as avidin/biotin, etc., which are capable of being detected in a suitable assay. In particular embodiments, one may also employ one or more fluorescent labels or an enzyme tag such as urease, alkaline phosphatase or peroxidase, instead of radioactive or other environmentally less-desirable reagents. In the case of enzyme tags, colorimetric, chromogenic, or fluorigenic indicator substrates are known that can be employed to provide a method for detecting the sample that is visible to the human eye, or by analytical methods such as scintigraphy, fluorimetry, spectrophotometry, and the like, to identify specific hybridization with samples containing one or more complementary or substantially complementary nucleic acid sequences. In the case of so-called "multiplexing" assays, where two or more labeled probes are detected either simultaneously or sequentially, it may be desirable to label a first oligonucleotide probe with a first label having a first detection property or parameter (for example, an emission and/or excitation spectral maximum), which also labeled a second oligonucleotide probe with a second label having a second detection property or parameter that is different (i.e., discreet or discernible from the first label. The use of multiplexing assays, particularly in the context of genetic amplification/detection protocols are well-known to those of ordinary skill in the molecular genetic arts.

The section headings used throughout are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

EXAMPLES

The following examples are included to demonstrate illustrative embodiments of the invention. It should be appreciated by those of ordinary skill in the art that the techniques disclosed in these examples represent techniques discovered to function well in the practice of the invention, and thus can be considered to constitute preferred modes for its practice. However, those of ordinary skill in the art should, in light of the present disclosure appreciate that many changes can be made in the specific embodiments which are disclosed and still obtain a like or similar result without departing from the spirit and scope of the invention.

Example 1—High Capacity Nanoporous Silicon Carrier for Systemic Delivery of Gene Silencing Therapeutics Drug development has traditionally been focused on a limited number of targets such as enzymes, transporters, G-protein-coupled receptors, and secreted proteins (Makley and Gestwicki, 2013). Most gene products are deemed as nondruggable since it is difficult to develop assays to measure their activities, and hence to carry out drug screening. As a result, many important proteins have been excluded from drug development efforts. This is especially true for cancer drug development. Many key cancer-causing genes encode transcription factors and these involved in protein-protein interaction (Suzuki et al., 2002; Li et al., 1999; Schlabach et al., 2008). The discovery of RNA interference (RNAi) has opened the door for the development of a new class of therapeutic agents for the treatment of human diseases (Fire et al., 1998). RNAi is considered to have the capability of knocking down any gene in any cell type. Consequently, a large number of gene silencing agents including small inhibitory RNAs (siRNA) and microRNAs are being evaluated for their anti-cancer activities.

As unformulated nucleotide oligos are rapidly degraded in body fluids, they are delivered in nanocarriers to enable the gene silencing agents to reach the designated tissues and exert function in vivo. The most commonly used nanocarriers for delivery of cancer therapeutics include liposomes and polymer-based nanoparticles with a size of less than 200 nanometers (Shen et al., 2012). The leaky vasculature in the tumor tissue enables nanoparticles within a size range of 100-500 nm to permeate into the tumor interstitium, taking advantage of the enhanced permeability and retention (EPR) effect (Matsumura and Maeda, 1986; Maeda, 2001). Furthermore, oligonucleotides are negatively charged and cannot pass the cytoplasmic membrane. Nanoformulation effectively facilitates cellular entry of the gene silencing agent.

Multiple siRNA-based candidate cancer drugs are currently being tested in clinical trials for efficacy and safety evaluation (Shen et al., 2012). Liver cancer and liver metastases of other cancer types are the primary disease indications for many of the candidate drugs, since the drug carriers tend to accumulate in the liver. Although promising advancement has been made in recent years on siRNA delivery, (Davis et al., 2010; Aliabadi et al., 2012) there is still an urgent demand for the design and development of new delivery systems to target other organs. It has been previously shown that porous silicon can be tailored to produce particles with defined size and shape (Godin et al., 2012). The destiny of the particles inside the body is determined by the size, shape, and surface physical and chemical properties. For example, discoidal particles are more effective in tumor accumulation than spherical or cylindrical particles (Decuzzi et al., 2010), and the 1,000× 400 nm discoidal particles accumulate more in tumor tissues and less in the liver or spleen than the 600×200 nm particles in the first 30 min after i.v. administration (van de Ven et al., 2011). In a recent study with a murine model of melanoma, it was determined that up to 5% of total injected dose of the 1 µm discoidal particles with polyamine surface modification were enriched in the tumor tissue after systemic delivery (van de Ven et al., 2011). Tumor accumulation has also been confirmed in murine models of primary breast cancer and metastatic ovarian cancer (Xu et al., 2013; Shen et al., 2013).

In addition, systemic administration of the discoidal porous silicon particles does not cause acute or sub-acute toxicity in wild-type mice (Xu et al., 2013). These results suggest the discoidal particles can serve as an efficient carrier for drug delivery to breast cancer, ovarian cancer, melanoma, and possible other types of solid tumors.

The discoidal porous silicon (pSi) particles described herein serve as facile delivery vehicles for RNA-based gene silencing agents when the surface of the nanopores is functionalized or conjugated with a polycation such as arginine (Arg), chitosan, dendrimer, polyethyleneimine (PEI), or a combination thereof. The resulting polycation-functionalized porous silicon (PCPS) has a high binding capacity for oligonucleotides. Confinement inside the nanopores prevents the polycation-bound oligonucleotide from interacting with toll-like receptors to trigger innate immune responses. Once inside the body, the porous silicon accumulates in tumor vasculature, and is gradually dissolved, thus releasing the oligonucleotide-bound polycation from confinement to form polyplex nanoparticles, which then deliver the therapeutic agent (e.g., an siRNA/microRNA) to cancerous cells, or to the tumor interstitium.

In this example, the inventors first conjugated 3-aminopropyl-triethoxysilane (APTES) onto the surface of porous silicon, and covalently attached Arg and PEI onto APTES sequentially. The PCPS, pSi-Arg-PEI, was then tested for siRNA binding capacity, releasing kinetics, and knockdown efficacy in cancer cells. A STAT3 gene-specific siRNA was used to test delivery to the tumor, and knockdown of gene expression in a murine model of breast cancer. In addition, potential innate immunotoxicity and sub-acute toxicity of the PCPS loaded with STAT3 siRNA was assessed. These studies confirmed that the disclosed compositions facilitate a highly-efficient efficient drug delivery system for in vivo/in situ delivery of one or more therapeutic constructs, incluing, for example, one or more gene silencing agent(s).

Materials and Methods

Materials.

Branched polyethyleneimine (MW 25-kDa), arginine, 1-ethyl-3-(3-dimethylaminopropyl) carbodiimide hydrochloride (EDC), N-hydroxysuccinimide (NHS), isopropyl alcohol (IPA), (3-aminopropyl)triethoxysilane (APTES) and N-(tert-butoxycarbonyl)-L-aspartic acid (Boc-Asp-OH) were purchased from Sigma-Aldrich (St. Louis, Mo., USA). Dulbecco's Modified Eagle Medium high glucose (DMEM) and fetal bovine serum (FBS) were from Fisher Scientific (Pittsburgh, Pa., USA). Small interfering RNA (siRNA)-Alexa Fluor© 555 was purchased from Qiagen (Hilden, Germany). Scrambled siRNA, GRP78 siRNA, miRNA-18a mimic, and STAT3 siRNA were ordered from Sigma. Female athymic nu/nu nude mice and FVB mice were acquired from Charles River (Burlington, Mass., USA).

Cell Lines.

The human breast carcinoma cell lines MDA-MB-231 and MCF-7, and murine RAW 264.7 cells were obtained from the American TypeCulture Collecction (ATCC; Rockville, Md., USA). Cells were cultured in DMEM supplemented with 10% FBS and 1% penicillin-streptomycin under the condition of 5% $CO_2$ and 95% humidity at 37° C.

Fabrication of Polycation-Functionalized Nanoporous Silicon Microparticles.

Fabrication of discoidal nanoporous silicon microparticles based on a combination of photolithography and electrochemical etch was described previously (Shen et al., 2012; Ananta et al., 2010), and surface APTES modification was performed as reported previously (Tanaka et al., 2010).

Arginine was covalently conjugated to APTES using EDC/NHS chemistry. Briefly, the acid group of arginine (0.1 nmol) was activated using EDC/NHS (0.1 nmol/0.1 nmol) in 20 mL ethanol for 4 hrs. pSi-APTES (10 billion particles) was then added, and the reaction was kept for 18 hrs at 20° C.

PEI was conjugated to the arginine group of pSi-APTES-Arg through an aspartic acid linker. Briefly, the N-tert-butoxycarbonyl (N-t-BOC) protected aspartic acid (0.1 nmol) was activated with EDC/NHS (0.1 nmol/0.1 nmol) in 20 mL ethanol for 4 hrs at 4° C. After acid activation, PEI (50 mg) was dissolved in 10 mL ethanol and added into the reaction mixture. The reaction was allowed to take place for 24 hrs at 20° C. In the second step of the reaction, the other acid group of aspartic acid was activated using EDC/NHS (0.1 nmol/0.1 nmol) at 4° C. for 6 hrs. After acid activation, pSi-APTES-Arg (10 billion particles) was then added into the reaction mixture, and the reaction was kept for 18 hrs at 20° C. The mixture was centrifuged, washed three times with ethanol, and polycation-functionalized particles were dried in vacuum. The size and zeta potential of the polycation-functionalized particles were measured with a Malvern multi-purpose titrator.

Loading of siRNA into PCPS Particles and Release of Arg-PEI/siRNA Polyplex Nanoparticles.

PCPS particles were mixed with siRNA in nuclease-free water, and incubated for 3 hrs at 4° C. for complete binding of siRNA to polycation. The suspension was then centrifuged to remove free siRNA oligos in the supernatant. To measure release profile of siRNA, PCPS particles loaded with Alexa Fluor© 555-labeled siRNA were incubated in PBS with 10% FBS at 37° C. in a shaker with a speed of 100 rpm. Supernatant was collected at different timepoints, and fluorescence intensity was measured with a H4 synergy hybrid plate reader (BioTek, Sinooski, Vt., USA).

Cellular Uptake of PCPS/Alexa Fluor© 555 siRNA Microparticles.

Cellular uptake of PCPS particles loaded with Alexa Fluor© 555-labeled siRNA was examined by confocal microscopy. MDA-MB-231 cells were plated in 4-well slide chambers at a seeding density of $1 \times 10^4$ cells/well and incubated for 24 hrs. PCPS/siRNA particles (1 million/well) were added into cell culture. Cells were harvested and fixed at different timepoints, and confocal microscopic images were obtained using a Fluo-View® TM1000 Confocal Microscope (Olympus, Inc., Shinjuku, Tokyo, Japan).

Intra-Cellular Trafficking of Arg-PEI/siRNA Polyplex Nanoparticle.

To monitor intra-cellular trafficking of siRNA polyplex, PCPS/FAM-labeled siRNA particles were incubated in PBS for 48 hrs. The released Arg-PEI/FAM siRNA polyplex nanoparticles were then collected by centrifugation, and added into culture medium of MDA-MB-231 cells. Cells were harvested at different timepoints (0.5 hrs, 2 hrs, 6 hrs, and 12 hrs), and fixed with 4% paraformaldehyde. The samples were then blocked with 1% bovine serum albumin (BSA) in PBS with 0.1% Tween-20® (PBST) solution, and stained with LysoTracker® (Invitrogen/Thermo Fisher Scientific, Waltham, Mass., USA) for late endosomes/lysosomes and DAPI for nuclei.

Gene Silencing In Vitro.

MDA-MB-231 or MCF-7 cells were seeded in a 6-well tissue culture dish at $2 \times 10^5$ cells/well in 2 mL DMEM containing 10% FBS. Cells were incubated with PCPS/siRNA for 72 hrs before they were harvested and analyzed via Western hybridization analysis. Proteins were extracted from cells using a M-PER® protein extraction reagent (Pierce, Inc./Thermo Fisher Scientific), separated on a 12% gel by SDS-PAGE, and transferred to a nitrocellulose membrane (Bio-Rad, Inc., Hercules, Calif., USA). Antibodies used for Western blot analysis were rabbit anti-human STAT3 antibody (Cell Signaling, 1:1,000 dilution), anti-human GRP78 antibody (Cell Signaling, Danvers, Mass., USA, 1:1,000 dilution), and anti-human ATM antibody (Cell Signaling, 1:1,000 dilution). The amount of protein was quantitated by densitometry, and the ratio to (3-actin protein level was calculated.

Quantitative RT-PCR Analysis In Vitro.

Real-time quantitative reverse transcription polymerase chain reaction (qRT-PCR) analysis was performed to examine STAT3, GRP78, and ATM mRNA expression with the ABI Prism® 7900HT Sequence Detection System (Applied Biosystems, Carlsbad, Calif., USA). (3-Actin served as the housekeeping gene for qPCR analysis, and the relative mRNA levels of target genes were normalized to the mRNA level of (3-actin. Cells were seeded in 6-well plates ($2 \times 10^5$ cells/well), treated with siRNA or microRNA, and harvested 48 hrs later. Total RNA was isolated using the TRIzol® reagent following the manufacturer's suggested protocol (Qiagen, Valencia, Calif., USA). Two micrograms of total RNA was transcribed into cDNA using the PrimeScript® first strand cDNA synthesis Kit (Takara Bio., Dalian, CHINA), and 2 pt of cDNA was subjected to qPCR analysis using the SYBR® Premix Ex Taq® (Clontech, Mountain View, Calif., USA).

Primer sequences for mRNA amplification were as follows:

```
STAT3 forward:
                                   (SEQ ID NO: 1)
5'-CAGCAGCTTGACACGGTA-3',;

STAT3 reverse:
                                   (SEQ ID NO: 2)
5'-AAACACCAAAGTGGCATGTGA-3',;

GRP78 forward:
                                   (SEQ ID NO: 3)
5'-CACAGTGGTGCCTACCAAGA-3',;

GPR78 reverse:
                                   (SEQ ID NO: 4)
5'-TGTCTTTTGTCAGGGGTCTTT-3',;

ATM forward:
                                   (SEQ ID NO: 5)
5'-TTCAAAGGATTCATGGTCCAG-3',;

ATM reverse:
                                   (SEQ ID NO: 6)
5'-GCTGTGAGAAAACCATGGAA-3';

β-actin forward:
                                   (SEQ ID NO: 7)
5'-AAATCGTGCGTGACATTAA-3',;
and β-actin reverse:
                                   (SEQ ID NO: 8)
5'-CTCGTCATACTCCTGCTTG-3'.
```

All reactions were performed in triplicate.

Knockdown of STAT3 Expression and Mammosphere Formation Efficiency Assay In Vivo.

All experimental procedures for animal studies were performed in accordance with institutional regulations. Nude mice bearing orthotopic MDA-MB-231 breast tumors were divided into seven treatment groups, and each mouse received treatment with free Scr siRNA (15 µg siRNA/injection, every 3 days), free STAT3 siRNA (15 µg siRNA/injection, every 3 days), liposome/Scr siRNA (15 µg siRNA/injection, every 3 days), liposome/STAT3 siRNA (15 µg siRNA/injection, every 3 days), empty PCPS ($100 \times 10^6$ PCPS microparticles on day 1), PCPS/Scr siRNA (15 µg siRNA in $100 \times 10^6$ PCPS microparticles on Day 1), or PCPS/STAT3 siRNA (15 µg siRNA in $100 \times 10^6$ PCPS microparticles on Day 1). Treatment was initiated when the average tumor size reached 150-200 mm³. Mice were sacrificed on Day 6 or Day 10 after the first treatment, and tumor samples were collected for expression analysis by Western blot and for mammosphere formation.

For mammosphere formation assay, tumor samples were minced and digested with 200 U/mL collagenase in the DMEM-F12 cell culture medium (Gibco/Thermo Fisher Scientific, Waltham, Mass., USA) for 1.5 hrs at 37° C. Single cells were collected, and seeded in ultra-low attachment plates at a density of 1,000 cells/well in the MammoCult™ basal medium (Stemcell Technologies, Vancouver, BC, Canada) for 1 to 2 weeks at 37° C. The number of mammospheres (cells >50) were counted under the microscope. Percentage of MSFE was calculated as number of mammospheres/number of total seeded cells.

In Vitro Immunotoxicity Assay.

RAW 264.7 cells were seeded in a 96-well tissue culture plate at 2×10⁴ cells/well in 100 µL DMEM containing 10% FBS. LPS served as the positive control (0.5 µg/mL), and the untreated cell as the negative control. Cells were treated with free siRNA, PEI/siRNA, mixture of pSi-Arg with PEI/siRNA, or PCPS/siRNA for 24 hrs, and levels of murine TNF-α and IL-6 were measured by ELISA.

Acute Immunotoxicity Analysis.

FBV mice were randomly divided into 12 groups (n=3). Each mouse received 15 µg siRNA in unprotected form (Scr or STAT3), as PEI polyplex (PEI/Scr or PEI/STAT3), as a mixture of pSi-Arg and PEI polyplex (pSi-APTES-Arg+ PEI/Scr or pSi-APTES-Arg+PEI/STAT3), or in PCPS (PCPS/Scr or PCPS/STAT3). LPS (5 mg/kg) served as the positive control. Mice were dosed by tail vein injection, and blood samples were taken at two and 24 hrs. Serum cytokine levels were measured with a multiplexed bead-based immunoassay from Millipore, which simultaneously evaluated the levels of: granulocyte/macrophage colony-stimulating factor (GM-CSF), interferon gamma (IFN-γ), interleukin-1beta (IL-1β), IL-2, IL-6, IL-9, IL-10, IL-12 (p40 and p70), IL-15, IL-17, LPS-induced CXC chemokine (LIX), tumor necrosis factor-alpha (TNF-α), monokine induced by IFN-gamma (MIG), macrophage inflammatory protein 2 (MIP-2), 1α, MIP-1β, macrophage colony-stimulating factor (M-CSF), regulated on activation normal T cell expressed and secreted (RANTES). The cytokine levels were determined using the 200 System™ Multiplex Bio-Assay Analyzer (Luminex®, Austin, Tex., USA) and quantified based on standard curves for each cytokine.

Sub-Acute Toxicity Analysis.

FVB mice received weekly treatment by tail vein injection for four weeks. The treatments included 15 µg siRNA in unprotected form (Scr or STAT3), as PEI polyplex (PEI/Scr or PEI/STAT3), as a mixture of pSi-Arg and PEI polyplex (pSi-APTES-Arg+PEI/Scr or pSi-APTES-Arg+ PEI/STAT3), or in PCPS (PCPS/Scr or PCPS/STAT3). The animals were observed for signs of toxicity throughout the experiment. Water and food consumption were recorded weekly. Body weight of the mice was measured every three days. At the end of the 4-week treatment, blood samples were collected for cell count and biomarker analysis. The biomarkers included aspartate aminotransferase (AST), albumin (ALB), alanine aminotransferase (ALT), blood urea nitrogen (BUN), creatinine (CREA), Cl⁻, Na⁺ and K⁺, alkaline phosphatase (ALKP), and lactate dehydrogenase (LDH). To further evaluate potential organ damage by PCPS/siRNA, FVB mice were treated weekly with PCPS/scramble siRNA (75 µg of siRNA) or PCPS/STAT3 siRNA (15 µg or 75 µg) by tail vein injection for four weeks. All major organs were collected, and histological analyses were performed.

Histopathological Examination.

Major organs including liver, spleen, kidney, lung, brain, and heart were harvested, fixed in formalin, and processed for histological evaluation by hematoxylin and eosin (H&E) staining. The tissues were fixed in formalin and embedded in paraffin. Tissue sections (4 µm) were analyzed to evaluate leukocyte infiltration, cell death, and other signs of organ damage. At least five random sections from each slide were examined.

Statistical Analysis.

All quantitative data are expressed as mean±standard deviations. Statistical analysis was performed with Student's t-test. Differences were considered statistically significant with p<0.05 (*) and p<0.01 (**).

Results

Fabrication of the PCPS Delivery System.

A four-step procedure for fabrication of the PCPS delivery vehicle is illustrated in Scheme 1 (FIG. 3). The surface of the porous silicon microparticle was first oxidized with $H_2O_2/H_2SO_4$ to expose a hydroxyl group that was used to conjugate APTES. Modification of porous silicon particle with APTES not only limits surface attack by water molecules and thus prevents the particle from rapid degradation, but also provides linkers for polycation conjugation. An Arg molecule was then conjugated to APTES, and the primary amino groups of PEI were subsequently attached to arginine. Loading of siRNA oligos into the nanopores was achieved through electrostatic interaction between the positively charged Arg-PEI and the negatively charged siRNA.

Characterization of the PCPS Delivery System.

Scanning electron microscopy (SEM) was applied to analyze morphological changes of the original porous silicon particles and the PCPS particles (FIG. 4A). The 1-µm discoidal particles contained 45- to 80-nm nanopores with a porosity of about 80% (Shen et al., 2012). The nanopores were clearly-defined structures, and the edges were evenly distributed across the particle (FIG. 4A, left panel). They were partially filled with the final product PCPS (FIG. 4A, right panel), indicating a substantial amount of Arg-PEI was conjugated inside the pores. Surface chemical modification of the particles was confirmed by changes in surface charge (FIG. 4B). APTES modification brought the Zeta potential from −37.5 mV to the positive territory, and Arg-PEI contributed significantly to the positive value of Zeta potential as a result of the cooperative effect of PEI and the guanidine residue in Arg (+2.38 mV for pSi-APTES, +3.72 mV for pSi-APTES-Arg, and +8.18 mV for pSi-APTES-Arg-PEI). SEM analysis revealed that the PCPS particles were more stable than the unmodified pSi particles in phosphate buffer saline (PBS). PCPS degradation was minimal in the initial 4-days' incubation, comparing to massive degradation for pSi during the same time. To characterize siRNA and nanoparticle formation, siRNA oligonucleotides labeled with the Alexa Fluor© 555 fluorescent dye were mixed with PCPS for complete siRNA-polycation binding. Confocal microscopic analysis confirmed the presence of Alexa Fluor© 555-labeled siRNA in the microparticles (FIG. 4C, left panel). These particles were then incubated in PBS. Arg-PEI/siRNA was released and polyplex nanoparticles were formed when the silicon dissolved (FIG. 4C, right panel). Fluorescence from the siRNA polyplex nanoparticles was not as bright as in PCPS/siRNA where the Alexa Fluor© 555-labeled siRNA was concentrated. The size of released polyplex nanoparticles was within 40 to 200 nm range with a median size of 102 nm as determined by dynamic light scattering (FIG. 4D). This size range was confirmed by atomic force microscopy (FIG. 4E). It is interesting to note that the median size of released polyplex was larger than that of the nanopores in porous silicon, indicating that the final polyplex structure formed during or after porous silicon degradation, but not inside the confinement of the porous silicon particle.

Loading and Release Kinetics.

Binding of siRNA to polycation in PCPS can be monitored by decrease in UV absorbance in supernatant or decrease in Zeta potential value. Within the first 30 min of incubation, 1.8 µg of siRNA oligos was loaded into $10 \times 10^6$ PCPS particles (FIG. 5A). Another 1.2 µg siRNA was loaded when the incubation time was extended to 3 hrs (FIG. 5A). The maximum loading capacity was 3.14 µg siRNA/$10 \times 10^6$ PCPS (FIG. 5B). This was a dramatic improvement over existing siRNA carriers. The porous silicon-based multistage vector system has been previously used to deliver siRNA packaged in nanoliposomes. To deliver 15 µg siRNA, $6 \times 10^8$ 1-µm size particles were needed to load liposomal siRNA. The number of particles would be reduced by 90% with the current platform. An increase in the binding of negatively-charged siRNA oligos to PCPS correlated with a decrease in the surface charge of the complex (FIG. 5C). Release of siRNA from the carrier was biphasic in 10% fetal bovine serum (FIG. 5D). A quick release profile was observed in the first four days—approximately 60% of the siRNA was released within this period, and another 20% was released over the next 10 days (FIG. 5D). Since siRNA was released as the polyplex nanoparticles underwent porous silicon degradation (FIG. 4A), the release curve indicated that the porous silicon was degraded gradually, resulting in a sustained release of the siRNA nanoparticle polyplexes. In a parallel experiment, PEI/siRNA polyplex nanoparticles were loaded into pSi-APTES-Arg, and particle release was monitored. Most particles exited the pSi-APTES-Arg carriers within the first three days. These results indicated that the Arg-PEI bond was essential for sustained release of the PEI/siRNA polyplex nanoparticles. Thus, a delivery system with high nucleotide binding capacity for sustained release of gene silencing agents has been developed.

Cellular Uptake of PCPS/siRNA and Intra-Cellular Trafficking of siRNA Polyplex Nanoparticle.

PSPC particles loaded with Alexa Fluor© 555-labeled siRNA were incubated with MDA-MB-231 human breast cancer cells in culture, and the fluorescent particles were monitored under a confocal microscope. Uptake of particles by breast cancer cells was apparent one day after inoculation (FIG. 6A). SEM analysis captured an image of particles at various stages of cellular entry (FIG. 6B). Multiple fluorescent particles could still be visualized on Day 7 and Day 12 (FIG. 6A).

FAM-labeled siRNA were loaded into PCPS, and collected Arg-PEI/siRNA following PCPS degradation in PBS. The green siRNA polyplex nanoparticles were incubated with MDA-MB-231 cells, and time-dependent intracellular localization was monitored (FIG. 6C). Confocal microscopic images showed that the FAM-labeled siRNA had reached endosomes/lysosomes (in red) after 30 mins of incubation, as the green fluorescent FAM-labeled siRNA co-localized with the red fluorescent endosomes/lysosomes. By the two-hour timepoint, almost all green FAM-labeled siRNA co-stained with the red endosomes/lysosomes, indicating maximum accumulation of siRNA in these organelles. Some siRNA molecules had exited these organelles by 6 hrs, and FAM-labeled siRNA could be visualized in multiple areas inside the cells by 12 hrs, suggesting successful endosomal escape of siRNA. Effective endosomal escape of the Arg-PEI/siRNA enabled siRNA molecules to exert their biological activities inside the cell. It has been speculated that polyamine molecules can serve as proton sponges that break endosomes (Sonawane et al., 2003). It is very likely that breakage of endosomes by Arg-PEI facilitated siRNA exit from late endosomes.

Knockdown of Gene Expression in Human Cancer Cells by PCPS/siRNA.

In order to test knockdown efficiency in human cancer cells and to identify the optimal ratio between siRNA oligo and polycation, MDA-MB-231 cells were incubated with an increasing amount of PCPS particles ($5 \times 10^6$ to $15 \times 10^6$) loaded with the same amount (1.4 µg) of siRNA oligos specific to the human STAT3 gene. This amount of siRNA oligo in a 2-mL cell culture was equivalent to 50 nM final concentration, a level commonly used in cell-based RNAi studies (Sonawane et al., 2003).

STAT3 encodes a transcription factor that plays a significant role in mediating the JAK/STAT signal transduction pathway (Seavey et al., 2012). A recent study indicated that STAT3 is an essential gene for breast cancer stem cells that are responsible for therapy resistance, tumor recurrence and metastasis (Marotta et al., 2011). Thus, knockdown of this gene might facilitate elimination of breast cancer stem cells. As controls for this study, MDA-MB-231 cells were also transfected with 1.4 µg STAT3 siRNA or scramble siRNA (Scr) using oligofectamine, a commonly used transfection reagent for siRNA (Elbashir et al., 2001). Cells were harvested 72 hrs post-transfection, and STAT3 expression was measured by Western blot analysis. Excellent knockdown of STAT3 expression was achieved in cells treated with 1.4 µg siRNA loaded into $8 \times 10^6$ to $15 \times 10^6$ PCPS particles (lanes 5 to 7: 86%, 74%, and 91% knockdown), but not in the cells treated with $5 \times 10^6$ particles (lane 4: 55% knockdown), suggesting that a certain level of nitrogen (from Arg-PEI) to phosphate (from siRNA) ratio (N/P ratio) has to be reached in the final product in order to achieve optimal biological activity. In a follow-up study, MDA-MB-231 cells were treated with PCPS particles loaded with STAT3 or scramble siRNA at the optimized ratio (1.4 µg siRNA in $15 \times 10^6$ PCPS particles). The controls were the same amount of free siRNA alone, siRNA transfected with oligofectamine, or PEI/siRNA polyplex. As anticipated, unprotected STAT3 siRNA alone did not have any effect on gene expression. Similar knockdown efficiency was observed in cells transfected with oligofectamine, or treated with PEI/STAT3 or PCPS/STAT3 (FIG. 7A).

MDA-MB-231 cells were also treated with siRNA specific for the GRP78 gene in order to confirm that the N/P ratio-dependent knockdown was not restricted to the STAT3 siRNA. GPR78 encodes a 78-kDa glucose-regulated protein, also known as heat shock 70-kDa protein 5, which modulates the activity of multiple endoplasmic reticulum stress proteins (Shen et al., 2002). As with STAT3, efficient knockdown was achieved at the right N/P ratio. At the optimal ratio, PCPS/GRP78 was as efficient on knockdown of gene expression as in cells transfected with oligofectamine or treated with PEI/GRP78 polyplex (FIG. 7A).

MCF-7 human breast cancer cells were treated with a microRNA-18a (miR-18a) mimic oligo. It has been previously reported that miR-18a regulates expression of the ATM gene (Qased et al., 2013). So ATM expression was assessed following miR-18a treatment. As expected, ATM expression in the positive control cells transfected with miR-18a was dramatically suppressed (71% knockdown).

Treatment with PCPS/miR-18a resulted in a more significant knockdown (85% to 90%) of ATM expression when the optimal number of PCPS particles were used (FIG. 7B).

In addition, changes were measured in mRNA levels following transfection with oligofectamine or coincubation with PEI or PCPS. The mRNA levels of STAT3, GRP78, and ATM in the post-treatment MDA-MB-231 and MCF-7 cells correlated with changes in protein expression by Western blot analysis (FIG. 7A-FIG. 7F). These results confirmed effective knockdown of gene expression by the PCPS-delivered siRNA and microRNA.

Delivery of siRNA In Vivo and Knockdown of Gene Expression in Tumor Tissues.

A murine model of MDA-MB-231 human breast cancer was generated to examine whether PCPS was effective in delivering gene silencing agents to solid tumors. Since tumor cells were inoculated into the mammary gland fat pad of female athymic nude mice, this model mimicked the pathological condition of human primary breast cancer. To test tumor distribution of particles, PCPS loaded with Alexa Fluor© 555-labeled siRNA were systemically administrated into the tumor mice. Mice were sacrificed 6 hrs later, and tumor tissues were collected for histological analysis. The presence of red fluorescent particles in the tumor cells could be visualized using fluorescence microscopy (FIG. 7C). Scanning electron microscopy (SEM) analysis of tissue-blocks also revealed clusters of particles inside the tumor (FIG. 7D).

In a separate study, mice bearing MDA-MD-231 primary tumors were treated once by tail-vein injection, with PCPS carrying siRNA specific for the human STAT3 gene. 100× $10^6$ PCPS particles were used to deliver 15 µg siRNA, a ratio that was within the optimal N/P range from the in vitro studies described above. In the control groups, mice were dosed i.v. with free siRNA or liposomal siRNA every 3 days. The animals were sacrificed on 6 or 10 days after the first dosing, and tumor tissues were collected for STAT3 expression analysis. While both PCPS/STAT3 and liposomal STAT3 caused reduction of STAT3 expression, Western blot analysis showed that the knockdown efficiency was more profound with PCPS/STAT3 treatment in both sets of samples (FIG. 7E). As expected, unprotected siRNA did not have any effect on STAT3 expression. Tumor samples from Day 10 were also digested for single cell isolation, and mammosphere formation efficiency (MSFE), one of the key features of breast cancer stem cells (Ponti et al., 2005), was measured. Knockdown of STAT3 expression by PCPS/STAT3 resulted in a significant reduction in MSFE (FIG. 7F), demonstraing the power of this new delivery system on delivery of siRNA to target key cancer genes.

Evaluation of Acute Immunotoxicity In Vitro and In Vivo.

Figures 1, 8A:
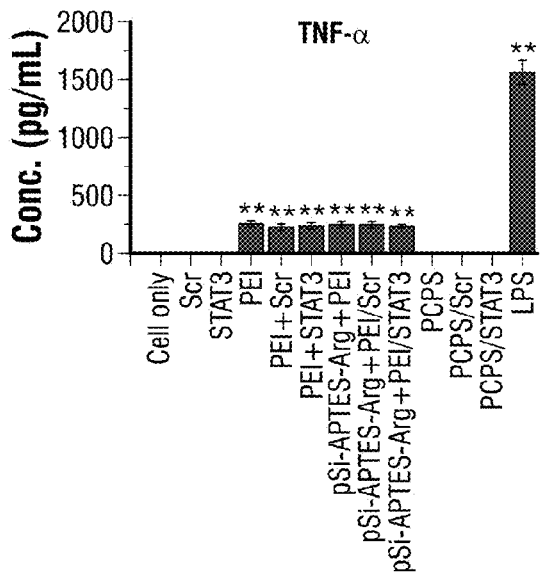
Figures 2, 8A:
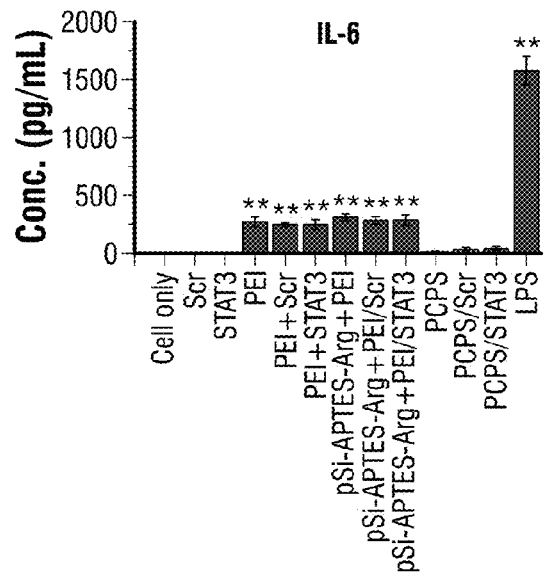
Figures 1, 8B:
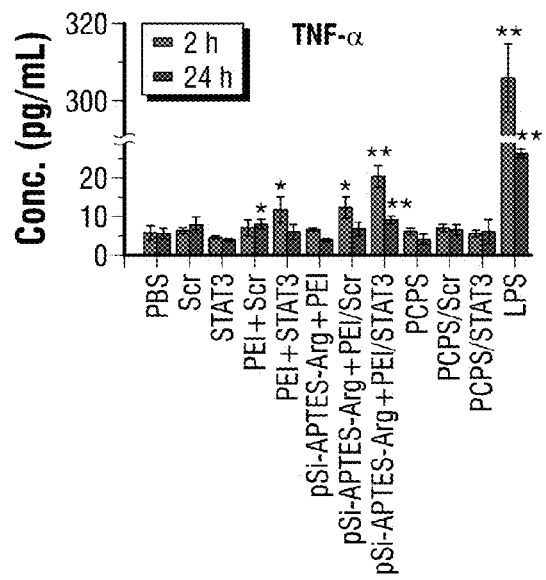
Figures 2, 8B:
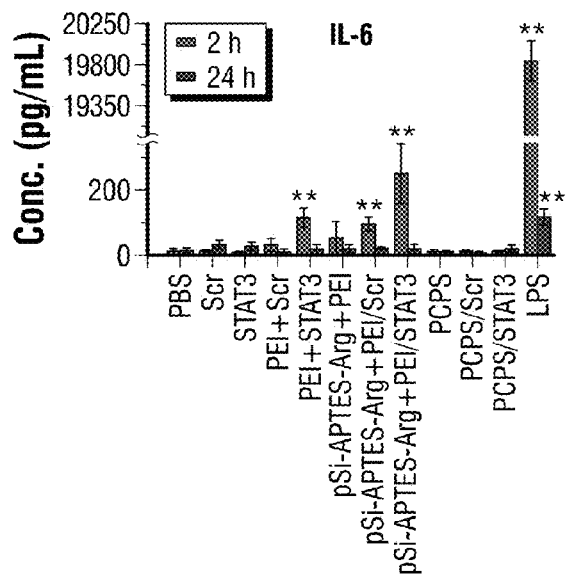
Figures 3, 8B:
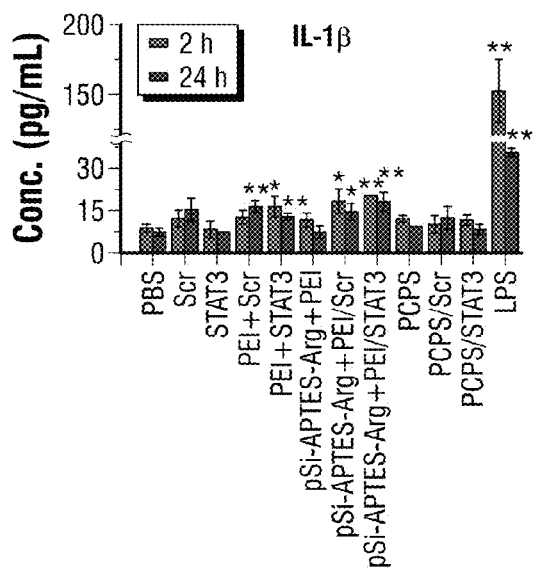
Figures 4, 8B:
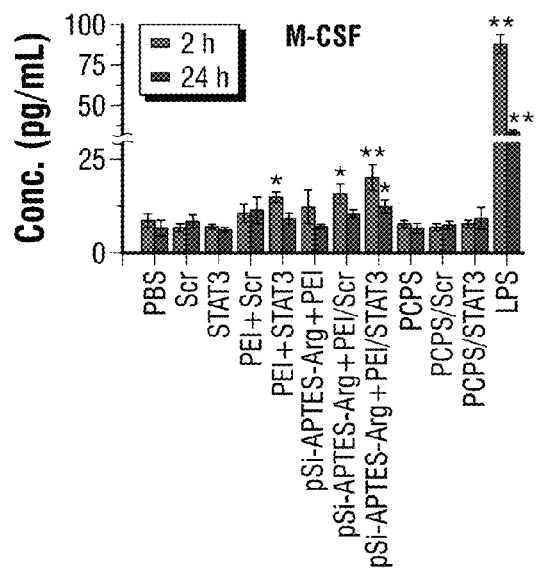
Figures 5, 8B:
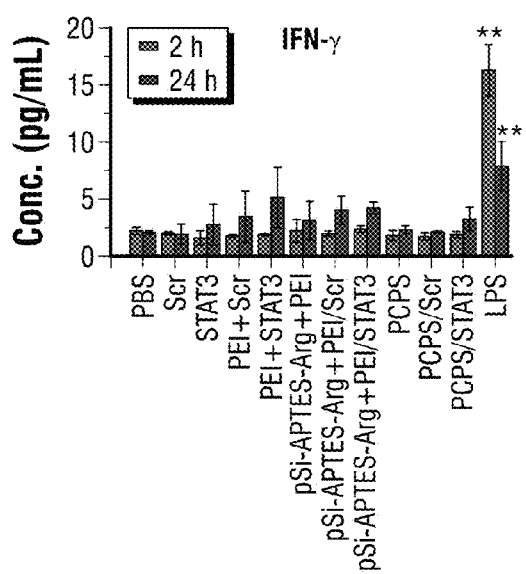
Figures 6, 8B:
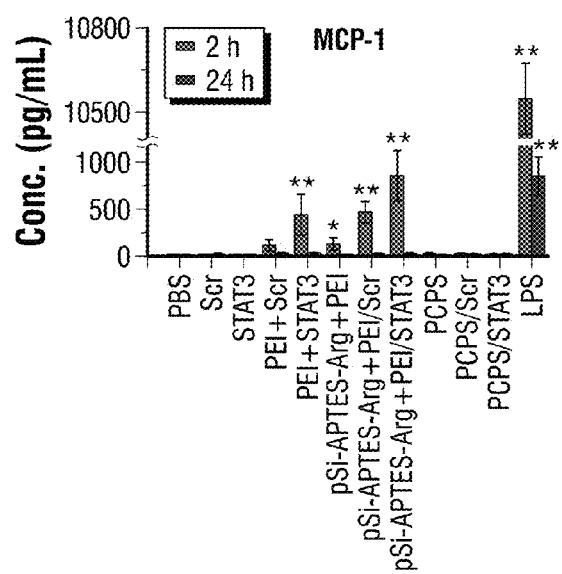

Potential immunotoxicity associated with this new delivery system was evaluated in cell culture and with wild-type mice. In the in vitro setting, both the empty vehicle and PCPS/siRNA were co-cultured with Raw264.7 murine macrophage cells, and levels of two key inflammatory mediators, tumor necrosis factor-alpha (TNF-α) and interleukin-6 (IL-6), were measured. Lipopolysaccharide (LPS) was used as a positive control for this assay, as its potential to induce innate immune response has been well documented (Tateda et al., 1996). Treatment with LPS triggered a surge in both TNF-α and IL-6 levels (FIG. 8A-1 and FIG. 8A-2). PEI or PEI/siRNA polyplex treatment also caused significant increases of both cytokines in cell culture media. A simple mix of pSi-APTES-Arg with PEI/siRNA polyplex did not prevent stimulation of cytokine production. Addition of these reagents into the culture medium with MDA-MB-231 cells also caused cell death. In contrast, treatment with empty PCPS or PCPS/siRNA did not elevate levels of TNF-α or IL-6 in Raw264.7 cells (FIG. 8A-1 and FIG. 8A-2). Moreover, they did not cause cytotoxicity to MDA-MB-231 cells, either.

In the in vivo seting, FVB mice were treated once with 1× therapeutic dosage (15 µg siRNA) of PCPS/siRNA by i.v. administration, and serum levels of chemokines and cytokines were measured. As in cell culture, LPS treatment caused dramatic increases in TNF-α within 2 hrs and IFN-γ at the 24-hr timepoint (FIG. 8B-1, FIG. 8B-2, FIG. 8B-3, FIG. 8B-4, FIG. 8B-5, and FIG. 8B-6). It also triggered secretion of most of the proinflammatory cytokines and chemokines such as IL-1β, interferon-γ, and MCP-1. Free PEI polyplxes and mixtures of PEI polyplex with pSi-APTES-Arg also significantly elevated serum levels of most of the proinflammatory cytokines (FIG. 8B-1, FIG. 8B-2, FIG. 8B-3, FIG. 8B-4, FIG. 8B-5, and FIG. 8B-6). However, neither PCPS/scramble nor PCPS/STAT3 siRNA caused significant changes in serum level of any of these factors (FIG. 8B-1, FIG. 8B-2, FIG. 8B-3, FIG. 8B-4, FIG. 8B-5, and FIG. 8B-6). These results demonstrated lack of immunotoxicity from PCPS or PCPS/siRNA.

Evaluation of Sub-Acute Toxicity.

Figures 3, 9B:
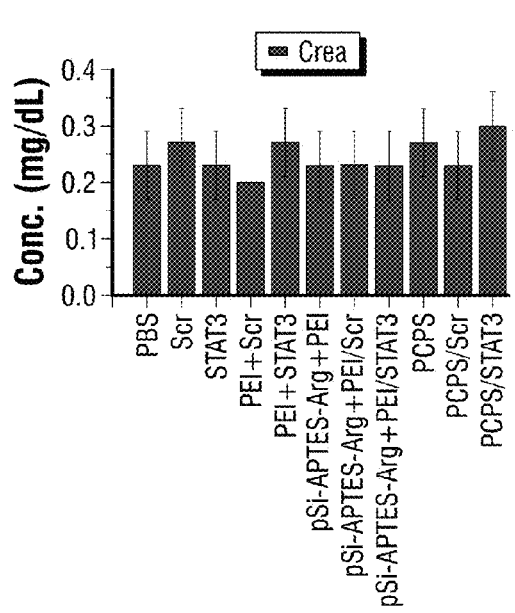
Figures 4, 9B:
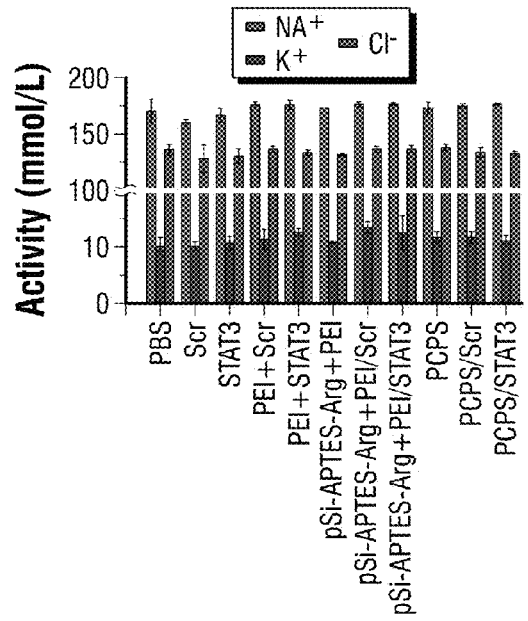
Figures 5, 9B:
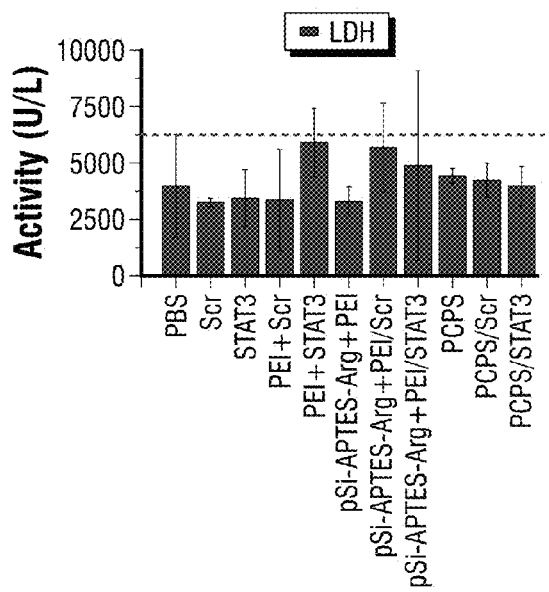
Figures 6, 9B:
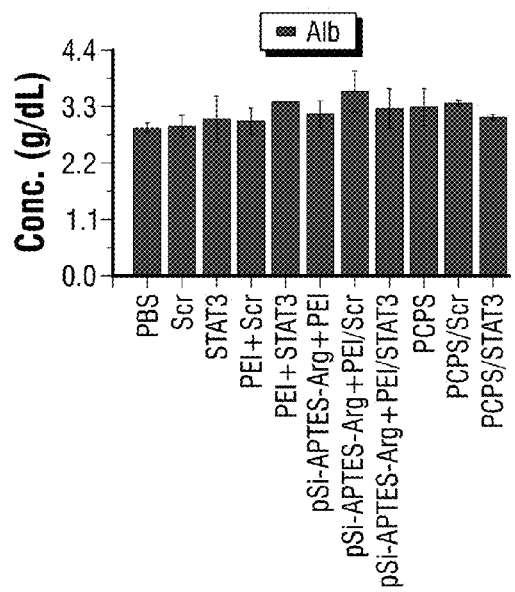

FVB mice were treated weekly by i.v. administration for four weeks with unprotected siRNA, PEI/siRNA polyplex, mixture of PEI/siRNA polyplex and pSi-APTES-Arg, or PCPS/siRNA. At the end of the treatment, whole blood samples were collected and cell counts were performed. Serum samples were collected and used to measure biomarkers associated with functions of the liver, kidney, and heart. Biomarkers for liver function included aspartate aminotransferase (AST), alanine aminotransferase (ALT), albumin (ALB), and alkaline phosphatase (ALKP). Parameters for renal function were blood urea nitrogen (BUN), creatine, $Na^+$, $K^+$ and $Cl^-$. Treatment with PEI/siRNA polyplex alone or in mixture with pSi-APTES-Arg resulted in significant elevation of red blood cells (FIG. 9A-1 and FIG. 9A-2). These treatments also raised plasma AST and lactate dehydrogenase (LDH) levels to or above the normal ranges (FIG. 9B-1, FIG. 9B-2, FIG. 9B-3, FIG. 9B-4, FIG. 9B-5, and FIG. 9B-6). The results indicate that PEI/siRNA polyplex has the potential to cause damages to major organs such as the liver. On the other hand, no hematological and biochemical values were altered in the empty PCPS or PCPS/siRNA treatment groups. To further confirm lack of toxicity from PCPS/siRNA, FVB mice were treated repeatly with 5-fold the normal dosage of PCPS/siRNA (75 µg siRNA in 0.5 billion PCPS particles per week for four weeks). Histological analysis of the major organs including brain, heart, kidney, liver, lung, and spleen supported the notion that particle treatment did cause damages to these organs (FIG. 9C). Taken together, repeated administrations of PCPS carrying scramble or STAT3 siRNA did not cause any detectable sub-acute toxicity.

Two key considerations in design of effective therapeutic delivery systems are efficiency and toxicity. Here, it is shown that PCPS were very effective in knocking down gene expression both in vitro and in vivo (FIG. 7A, FIG. 7B, FIG. 7C, FIG. 7D, FIG. 7E, and FIG. 7F). Also, knockdown of STAT3 expression in MDA-MB-231 primary tumors resulted in a significant reduction of cancer stem cells. Since these cells are responsible for tumor recurrence and metastasis (Al-Hajj et al., 2004; Yu et al., 2007), reduction of the cancer stem cell population by PCPS/STAT3 siRNA suggests a possible synergy with other cancer drugs that kill the bulk of non-stem cell cancer cells.

Previous reports have indicated that high-molecular-weight PEI can cause severe cytotoxicity (Hunter et al., 2006). Certain siRNA oligos, when packaged in cationic or liposomal carriers, trigger toll-like receptors and induce interferons and inflammatory cytokines (Hornung et al., 2005; Thomas et al., 2003). In this example, cytotoxicity and immunotoxicity were evaluated in free PEI and PEI/siRNA polyplexes. Subacute toxicities have also been observed in mice treated with these agents. In comparison, there was no sign of such toxicities from either the empty PCPS delivery carrier or siRNA-loaded PCPS. No acute toxicity from PCPS was detected in either in vitro or in vivo settings. Furthermore, repeated treatments with increased dosages did not cause damages to major organs in wild-type mice (FIG. 9C). Several factors in the design of this delivery system might have contributed to the lack of toxicity. It is well known that PEI causes toxicity by interaction with glycocalyx on the cell surface, resulting in the formation of large clusters. In addition, the primary amine moieties of PEI are more cytotoxic than the secondary or tertiary amines (Hunter et al., 2006; Thomas et al., 2003). Conjugation of PEI into the nanopores inside porous silicon shields the molecule from interacting with cells. In addition, covalent linkage with arginine eliminates the primary amine group in the molecule. Furthermore, an Arg-PEI/siRNA nanoparticle enters the cell via vesicular transport, reducing the chance of interaction with molecules on cell surface. Slow degradation of the silicon particles also limited the amount of PEI exposure to cells at a given time. These results point to a desirable safety profile for the new delivery system described herein.

In conclusion, a new carrier for the delivery of gene silencing agents has been synthesized and tested. The PCPS showed a high oligonucleotide-binding capacity, and importantly, a lack of any detectable toxicity. This new system is easy to operate, and can be used to deliver one or more therapeutic agents, such as siRNA or microRNA, to achieve knockdown of various cancer genes in vivo. Such gene silencing agents will likely play a dominant role in the treatment of human cancers in the upcoming years, and the development of the present system makes their use even more promising.

It has been estimated there are up to 100 mutations in a breast cancer, many of them driving mutations (Wood et al., 2007). Large numbers of mutations have also been identified in other cancer types (Wood et al., 2007; Jones et al., 2008). Furthermore, since each individual patient has a unique mutation spectrum, the total number of combination of cancer-causing genes is incredibly large. Unfortunately, conventional cancer drugs only target a handful of gene products. However, this gap may be bridged by the exploitation of gene silencing agents as primary cancer therapeutics. This new therapeutic agent delivery system offers an excellent enabling platform in the era of personalized medicine.

Example 2—Polycation-Functionalized Nanoporous Silicon Particles for Gene Silencing on Breast Cancer Cells FIG. 10A illustrates the synthesis and surface modification of mesoporous silicon nanoparticles (MSNP). FIG. 10B shows an agarose gel electrophoresis of exemplary PEI-Phos-MSNP particles containing siRNAs prepared as described below. siRNA oligos (0.2 µg) were incubated with increasing amount of PEI-Phos-MSNP particles. They were then applied to electrophoresis in agarose gels. When the PEI-Phos-MSNP-to-siRNA ratio was greater than 5, all siRNA oligos remained with the particles in the gel loading well, which indicated tight binding.

FIG. 11A, FIG. 11B, FIG. 11C, FIG. 11D, and FIG. 11E show the characterization of exemplary MSNP. Shown are the changes in surface charge (FIG. 11A) and images of the MSNP particles (FIG. 11B, FIG. 11C, FIG. 11D, and FIG. 11E) during chemical modification. FIG. 11A shows the changes in surface charges determined based on zeta potential during different stages of particle modification. The initial material (MSNP-OH) has a negative surface charge, and the final product (APTES-MSNP) carries a positive surface charge. Surfaces charges were determined both in water and in phosphate buffer (pH=7.4). FIG. 11B shows a scanning electron microscopic view of MSNP-OH particles. FIG. 11C shows a transmission electron microscopic view of MSNP-OH particles, while FIG. 11D shows a transmission electron microscopic view of Phos-MSNP particles. FIG. 11E shows a transmission electron microscopic view of PEI-Phos-MSNP particles.

FIG. 12A and FIG. 12B show exemplary stability comparisons of PEI-Phos-MSNP/STAT3 particles (FIG. 12A) prepared in accordance with the present invention, to PCPS/STAT3 particles (FIG. 12B) prepared in accordance with conventional methods available in the prior art; samples were stored at 4° C., siRNA 50 nM, transfection 3 days. These data clearly demonstrated the stability of the siRNA-loaded MSNP particles of the present invention over a period of at least six weeks, when stored under conventional refrigeration conditions, compared to the relatively-unstable prior art particles, that were substantially degraded after only a few days.

In order to reap the full benefits of RNA interference (RNAi)-based therapy, effective siRNA delivery systems are highly desirable. It has been shown that non-viral siRNA delivery systems are superior to their viral counterparts, due to easy preparation, lower cost, enhanced biocompatibility, and improved biosafety (Ferrari; 2005; Nishiyama et al., 2006; Zhang and Kataoka, 2009; Miyata et al., 2012; Ogris and Wagner, 2002; Merdan et al., 2002; Li and Huang, 2006; Felber et al., 2012; mesopore as "nanogate" to prevent small molecules (i.e., anti-cancer agent) Wang et al., 2012). In particular, mesoporous silica nanoparticles (MSNs), with a typical pore size in the range of 2-10 nm, have demonstrated promise as carriers for nanomedicine, including nucleic acid, among others (Lee et al., 2011; Xia et al., 2009; Li et al., 2013). Nano-constructs, typically formed via self-assembly between oppositely charged species, i.e., a nucleic acid and a cationic polymer, are installed or adsorbed outside the entrapped inside the mesopore from leaking out. Upon application of external stimuli, the nanogate dissociates releasing the small-molecule cargo inside the mesopore. It is recognized that the small pore of MSNs may hinder the efficient loading of larger biomolecules (i.e., nucleic acid or protein). Therefore, most of the studies, in which MSNs were used for nucleic acid delivery, have focused on surface-coating of the MSNs with a cationic polymer (i.e., PEI), allowing for complexation with anionic nucleic acid (Xia et al., 2009; Li et al., 2013). It should be noted that since the polymer/nucleic acid complexes were adsorbed or anchored on the outer surface of the MSNs, these nano-constructs, which were self-assembled via electrostatic interaction, might be vulnerable to enzymatic degradation or even compromised upon injection in the systemic circulation.

In an effort to address such challenges induced by the small pore size, Na et al. recently expanded the pore size of the as-prepared small-pore MSNs, i.e., an increase from 5 nm to 23 nm, using a post-synthesis treatment of the small-pore MSNs (Na et al., 2012). Comparisons were made between the two types of MSNs with different pore sizes, in terms of their applications as siRNA delivery systems. Results showed that increasing the pore size of MSNs could be a useful strategy towards the improvement of MSN-based siRNA delivery for in vivo applications.

Over the past few years, a series of nanoporous silicon particles (pSi) have been developed with a much larger pore size (i.e., with an average diameter of ~20 to ~60 nm) and these particles have been utilized as multi-stage vectors (MSVs) for systemic delivery of therapeutic or diagnostic agents, including siRNA (Godin et al., 2011; Shen et al., 2012; Shen et al., 2012b; Xu et al., 2013; Shen et al., 2013, Tanaka et al., 2009; Ananta et al., 2010; Tasciotti et al., 2008). Due to the larger pore size, nanoconstructs packaged with therapeutics can be readily loaded inside the pore interiors of these pSi particles to achieve a sustained-delivery of the therapeutic to selected tumor cells.

In a typical MSV approach, charged nanoliposomes packaged with small-molecule drugs or therapeutic siRNAs are loaded into the pore interior of the pSi particles via electrostatic interaction and capillary force. Once inside the body, the pSi particles (i.e., the "Stage 1" particles) are gradually degraded, and the nanoliposomes (i.e., the "Stage 2" particles contained therein) are released from the Stage 1 pSi particles, thus facilitating a multi-stage release. This delivery system has advantages of both enhanced loading efficiency and an easy tunability with respect to particle shape and size, which allows for efficient encapsulation of nano-sized species into the MSV. This shields them from contact with unintended organs or cells, and, thus leads to minimal toxicity and enhanced efficacy.

Moreover, investigating the effects of shape and size on the biological properties both in vitro and in vivo showed that in comparison to hemi-spherical pSi particles (Decuzzi et al., 2010), discoidal pSi particles exhibited enhanced properties towards their applications as effective carriers in cancer therapy, as evidenced from their increased surface area, improved biodistribution in multiple animal tumor models, among others. In view of the complex biological environment, i.e., the presence of numerous charged species in the plasma, and in the tumor interstitium, what was needed in the art was a loading strategy in which the siRNA-containing nanocomplexes are anchored inside the nanopores of pSi particles in order to minimize the interaction between the siRNA-containing nanocomplexes and the charged biological species upon systemic administration of the resultant pSi particles. Upon gradual degradation of the pSi Stage 1 particles, the siRNA-containing nanocomplexes (Stage 2 particles) could then be released (in a sustained manner) to permit favorable pharmacokinetics. Additional features facilitated by such a delivery system include its versatility for multiple therapies, which offers dramatic clinical significance (Pecot et al., 2011).

In this example, a platform is described, in which a cationic polymer, namely polyethyleneimine (PEI), was readily conjugated to the pore interior of pSi particles via straightforward chemistry, followed by electrostatic complexation with anionic siRNA to form PEI/siRNA nanoparticles.

PEI has been widely used as non-viral delivery systems for nucleic acids (Fischer et al., 2003; Russ et al., 2008). Upon gradual degradation of the pSi matrix under physiological conditions, the siRNA-containing PEI nanoparticles are released from the nanopore confinement. The resulting nanoparticles were then subsequently internalized into cells leading to gene silencing. In this example, the ataxia telangiectasia-mutated (ATM) gene, which has been previously shown to play an important role in cancer therapy (Xu et al., 2009; Canman and Lim, 1998), was used as a gene target to demonstrate the efficacy of the delivery system described herein.

Materials and Methods

Materials.

All reagents and medium were obtained from Sigma Aldrich (USA), Lonza, or Promega (USA), and used without further purification. RNase-free $H_2O$ was supplied by Fisher Scientific (USA). siRNAs were synthesized by Thermo Scientific. All other chemicals and reagents were of analytical grade and were used as received.

Preparation of pSi Particles.

pSi particles were fabricated by electrochemical etching of silicon wafers in the Microelectronics Research Center at The University of Texas at Austin as previously described (Chiappini et al., 2010). The pSi particles were oxidized with $H_2O_2$ (30%) at 100° C. for 2 hrs to add the —OH functionality on the surface. Subsequently, the oxidized pSi particles were reacted with 3-(triethoxysilyl)propyl isocyanate (TEIC) to yield the —NCO functionality (Radu et al., 2004), which was then subjected to conjugation of PEI in anhydrous ethanol. The mixture was rinsed with ethanol, and centrifuged twice to remove unreacted chemical or PEI from the resulting pSi particles.

Particle Characterization.

Zeta potential measurements and dynamic light scattering (DLS) were carried out using a Zeta Sizer Nano ZS (Malvern Instrument, Malvern, UK). Particles were dispersed in PB buffer (pH 7.4) at a concentration of 0.5 mg/mL. The samples were mixed well by sonication for 10 sec before analysis. Morphological observation was performed using Bruker MultiMode atomic force microscopy (Bruker, USA). Particle density was measured using a Multisizer 4 Coulter Particle Counter (Beckman-Coulter, Brea, Calif., USA). Prior to the analysis, the samples were dispersed in the balanced electrolyte solution (ISOTON® II Diluent, Beckman Coulter) and sonicated for 10 sec to ensure a homogenous dispersion. Absorbance and fluorescence measurements were performed with BioTek Synergy H4 hybrid multi-mode microplate reader (BioTek, USA) using a Take3™ Micro-Volume plate (BioTek). Morphological studies were performed using SEM (FEI Nova NanoSEM 230, Hillsboro, Oreg., USA) operated at 20 keV, or transmission electron microscopy (TEM) (JEOL 2010 Peabody, Mass., USA) equipped with a CCD camera and operated at 120 keV.

In Vitro Transfection.

MDA-MB-231 cells were seeded in 6-well microplates at a density of $2 \times 10^5$ cells/well and allowed to attach overnight in Dulbecco's Modified Eagle's Medium (DMEM) supplemented with 10% heat-inactivated fetal bovine serum (FBS). After the attachment, the culture medium was replaced with fresh DMEM without FBS. The as-prepared pSi-PEI/siRNA particles were re-dispersed with DMEM to desired concentrations. 100 μL of the diluted sample solution was added to each well, and the cells were incubated at 37° C. for 60 hrs under a 5% $CO_2$ atmosphere. As a control, siRNA transfected with a commercial transfection reagent INTERFERin® (Polyplus Transfection, Illkirch, France) was used, by following the manufacturer's instructions.

Confocal Laser Scanning Microscopy (CLSM) Observation.

Confocal images were acquired using a FluoView® 1000 laser scanning fluorescence microscope (Olympus) equipped with an oil-immersion 100× numerical aperture PlanS Apochromat objective lens. The cells were seeded on 35-mm dishes with a cover glass bottom (MatTek Corporation, Ashland, Mass., USA). To visualize the hybrid particles, Alexa Fluor© 555-labeled siRNA was used. The identical protocol was employed for the siRNA transfection as that for the above-mentioned transfection studies. After transfection for desired time intervals, the cells were washed twice with PBS and fixed with 4% paraformaldehyde in PBS. The nuclei and the endosomes/lysosomes were stained with DAPI and LysoTracker® Green, respectively. Excitation wavelengths were 405 nm, 488 nm, and 543 nm, for DAPI, LysoTracker® Green, and Alexa Fluor, respectively.

Western Blot.

MDA-MB-231 cells were seeded in 6-well plates ($2\times10^5$ cells per well). Identical cell culture conditions and siRNA transfection protocols as described above were followed. 60 hrs after the transfection, the cells was rinsed with PBS and harvested by trypsinization. The treated cells were washed, and then incubated with lysis buffer containing protease and phosphatase inhibitors. Protein lysates were recovered and the concentration was determined using a BCA assay (Thermo Fisher Scientific). Then, protein lysates were mixed with SDS loading buffer and heated at 95° C. for 5 min. Samples were separated by electrophoresis with Mini-PROTEAN™ precast gels (Bio-Rad) and transferred to nitrocellulose membranes (Bio-Rad, USA). Membranes were blocked for 1 hr in 5% non-fat milk in Tris-buffered saline with 0.1% Tween-20™, and subsequently incubated with desired primary antibody (Cell Signaling Technology) overnight. After washing, they were incubated with HRP-conjugated secondary antibody (Cell Signaling Technology) for 1 hr. Membranes were washed and protein bands were detected by enhanced chemiluminescence using a Chemi-Doc™ XRS+ imaging system (Bio-Rad).

Animal Studies.

Female FBV mice (5-6 weeks old, 19-24 g, Charles River Laboratories) were maintained in a VAF-barrier facility. Mice were randomly divided into 5 groups (n=4) and received a single injection through the tail vein. In the single administration setting, each mouse was injected with 100 μL of aqueous solution containing 15 μg or 75 μg of siRNA. Control mice were administered via i.v. injections of PBS and pSi-PEI complexed with scramble siRNA (pSi-PEI/Scr) at an identical siRNA dosage. Fifteen days after injection, whole blood was collected for complete blood testing and biochemical analysis. All studies involving animals were performed in accordance with approved institutional protocols.

Whole Blood Analysis.

Blood samples were collected from mice fifteen days after the injection. The samples were analyzed for the number of percentage of total white blood cells (WBC), lymphocytes (LYM), monocytes (MONO), and granulocytes (GRAN). In addition, hematocrit value (HCT), mean corpuscular volume (MCV), red blood cells (RBC), hemoglobin content (HGB), mean corpuscular hemoglobin (MCH), mean corpuscular hemoglobin concentration (MCHC), and red cell distribution width (RDW) were determined.

Serum Biochemistry.

Sera were obtained from the blood samples mentioned above. Parameters related to hepatic function (i.e., aspartate aminotransferase (AST), analine aminotransferase (ALT), and alkaline phosphatase (ALKP)) and renal function (i.e., blood urea nitrogen (BUN) and creatinine) were measured.

Histological Evaluation.

Tissues were fixed in 10% formalin, and embedded in paraffin. Tissue sections (5 μm) were stained with hematoxylin/eosin (H&E). Microscopic analysis was performed, and at least five random sections from each slide were examined.

Results and Discussion

Particle Modification and Physicochemical Characterization.

Pristine pSi particles, with —OH surface functionality, were modified with 3-(triethoxysilyl)propyl isocyanate (TEIC) to yield isocyanate functionality, which can readily react with the amine-containing PEI polymer (molecular weight: 25 kDa). The resulting positively-charged PEI-conjugated pSi particles (pSi-PEI) were complexed with negatively charged siRNA. Zeta potential measurements confirmed the success of each preparation step (FIG. 13), as evidenced by the results showing that the surface potential of the pSi particles varied in accordance with different surface functionalities.

SEM analyses were carried out for the pristine pSi, pSi-PEI and pSi-PEI/siRNA particles, as shown in FIG. 14A, FIG. 14B, and FIG. 14C. The nanoporous pSi particles exhibited well-defined disc-like shape, with a diameter of around 1 μm and a height of around 400 nm. The presence of nano-sized pores, with a pore size of between 30 and 60 nm, allowed for efficient encapsulation of siRNA-containing nanocomplexes inside the pore. In addition, TEM observation was performed on the pSi-PEI/siRNA particles (FIG. 14D and FIG. 14E). Due to the difference in electron conductivity between the semi-conducting silicon matrix and the insulating polymer layer, the TEM images further revealed that a thin non-conducting layer containing PEI/siRNA nanocomplexes was present in the pore interior as well as on the outer surface of the pSi particles, validating the notion of PEI/siRNA nanocomplexes being anchored onto the pSi matrix.

In addition to electron microscopic analysis, fluorescence microscopy was also used to verify the formation of fluorescent pSi-PEI/siRNA particles. To this end, Alexa Fluor© 555-labeled siRNA (AF-siRNA) was used to complex with pSi-PEI to yield pSi-PEI/AF-siRNA particles, which were visualized with a fluorescence microscopy. FIG. 14F shows that when excited with laser, the particles emitted significant red fluorescence, with a size of approximately 1 μm, thus confirming the presence of pSi-PEI/AF-siRNA particles.

Determination of Loading Efficiency.

It has been recognized that the siRNA loading capacity is critical to the development of practical siRNA delivery systems (Nishiyama and Kataoka, 2006). To evaluate the loading capacity of the pSi-PEI particles, various amounts of siRNA were used to complex with a given amount of pSi-PEI particles. Centrifugation was performed at 14,000×g to ensure the absence of free or unbound siRNA on the resulting pSi-PEI/siRNA particles. Encapsulation efficiency was calculated by the difference in optical density at 260 nm between the supernatant and the pre-loading siRNA solution. Moreover, surface potential measurements were performed to monitor the progress of the complexation between pSi-PEI and siRNA. FIG. 15 shows that the surface potential decreased with increasing siRNA loading until it reached a plateau, suggesting that all the cationic PEI chains were bound to the anionic siRNA. A complete complexation between PEI and siRNA enabled determination of the maximum siRNA loading efficiency for a given pSi-PEI particle. Due to the efficient complexation between the pSi-PEI and siRNA, a maximum of 70 μg of siRNA could be bound to one billion of pSi particles.

Degradation of pSi Matrix and Sustained Release of Payload.

To validate the notion of sustained release of payload anchored inside the nanopores, it was important to verify the structural integrity of the PEI/siRNA nanoparticles during the gradual degradation of the pSi matrix. To that end, the pSi-PEI/siRNA particles were dispersed in PBS and incubated at 37° C. for 24 hrs to ensure complete dissolution of the pSi matrix. Centrifugation was performed and the supernatant was collected for further characterization.

First, morphological observation was performed using atomic force microscopy (AFM). FIG. 16A shows that the resultant PEI/siRNA nanocomplexes exhibited spherical shape with an average particle size ranging from 20 to 40 nm, which is close to the pore size of the pSi particles. These results confirmed that the particle size of the PEI/siRNA nanocomplexes was governed by the steric confinement of the nanopores. Dynamic light scattering (DLS) measurements (FIG. 16B) revealed that the as-released nanoparticles exhibited a hydrodynamic diameter of around 120 nm, with a very narrow particle size distribution (PDI<0.1). It was noted that the difference in the particle size obtained by AFM and by DLS was attributed to the different sample states required by the two characterization techniques, i.e., dry state (ca. 30 nm) vs. hydrated state (ca. 120 nm). The results obtained from DLS measurements were consistent with those obtained for the PEI/siRNA polyplex nanoparticles reported in the literature (Moghimi et al., 2005), even though these particles were somewhat smaller than the latter (likely induced by the confinement effect of the pSi particles). They clearly demonstrated the advantages of a nanopore-templated siRNA delivery system, in which the integrity of the PEI/siRNA nanoparticles anchored inside the nanopores remains intact during the sustained release process.

Cellular Trafficking.

In order to gain better insight into how the siRNA-containing particles transport inside the cells, cellular trafficking studies using fluorescence microscopy yielded useful information. Cellular trafficking study of hybrid pSi-PEI/Alexa Fluor© 555-labeled siRNA particles (or pSi-PEI/AF siRNA) was performed. These particles were used for transfection with MDA-MB-231 human breast cancer cell line. Confocal laser scanning microscopy (CLSM) was performed 4 hrs and 18 hrs post-transfection. At 4 hrs post-transfection, significant co-localization between the siRNA and the endosomal compartment, as revealed by the overlap between the red Alexa Fluor© 555-labeled siRNA and the green staining for the endosomal compartment (FIG. 17A), was observed. The result indicates that particles containing AF-siRNA were taken up by the cells via endocytosis.

Furthermore, cellular trafficking study by CLSM was performed for the as-released nanoparticles, which were recovered after the degradation of pSi-PEI/AF-siRNA hybrid particles under identical experimental conditions as employed above. At 4 hrs post-transfection, confocal images were acquired using the identical procedures as for the prior CLSM observation. FIG. 17B demonstrates the significant co-localization observed between the siRNA and the endosomal compartments, as seen from the overlap in fluorescence signals contributed from the labeled siRNA and the endosomal compartment, respectively. These results were indicative of cellular internalization of the PEI/AF-siRNA nanoparticles released from the pSi matrix. At a longer time scale (i.e., 18 hrs), a lesser degree of overlap between the labeled siRNA and endosome/lysosome compartments was detected, accompanied by the presence of two separate fluorescence signals attributed to the individual species (FIG. 17C). These data indicated that siRNA-containing particles may escape from the late endosomal/lysosomal compartments, thus exerting a gene silencing effect.

Gene Knockdown Against ATM Cancer Gene by Western Blot.

To determine whether the internalized siRNA-containing particles could result in significant gene knockdown against the target cancer gene, ATM, RNAi efficacy was evaluated for the pSi-PEI/siRNA hybrid particles by performing Western blot analysis on MDA-MB-231 cells. Cells transfected with pSi-PEI particles complexed with scrambled siRNA (pSi-PEI/siSCR), PEI(25k)/siATM nanocomplexes, and siATM using a commercially available transfection reagent (i.e., INTERFERin®) were used as controls. As shown in FIG. 18, pSi particles containing scrambled siRNA did not induce any RNAi effect, demonstrating that gene silencing observed for the ATM gene occurred in a sequence-specific manner. In addition, concentration-dependent gene silencing effect was carried out. Dramatic gene knockdown was achieved at an siRNA concentration of 70 nM. The results clearly demonstrate the advantage of utilizing PEI-conjugated pSi particles as an effective carrier to deliver siRNA to human breast cancer cells.

In Vitro Biocompatibility Evaluation.

One of the major advantages of using a non-viral siRNA delivery system as opposed to a viral delivery system is its potentially superior biological safety. It has also been recognized that low or minimal toxicity is highly desirable for clinical applications. The cytotoxicity of pSi-PEI/siRNA particles was assessed on MDA-MB-231 cells. MTT assay was performed 48 hrs and 72 hrs after the cells were exposed to the particles. The as-prepared hybrid particles exhibited no cytotoxicity for siRNA concentrations as high as 100 nM, indicating significant biocompatibility in vitro. Taking into account the fact that almost complete gene knockdown was achieved at an siRNA concentration of 70 nM, the siRNA delivery system based on pSi-PEI particles is a promising candidate for the enhanced delivery of siRNA to cancer cells in general, and to breast cancer cells in particular.

After the hybrid pSi particles are administered into the bloodstream, they encounter a complex biological environment of plasma proteins and immune cells. Particle uptake by immune cells in circulation, such as macrophages, monocytes, leukocytes and dendritic cells, takes place through various pathways. Thus, it was important to evaluate the extent of response of macrophages to external stimuli. Evaluation of cytokine release was performed on RAW 264.7 mouse macrophage cells. Cells treated with polyinosinic-polycytidylic acid (Poly(I:C)) or PBS were used as control. Levels of two typical pro-inflammatory cytokines (i.e., TNF-α and IL-6), indicative of an inflammatory process, were quantified 24 hrs after the cells were exposed to various pSi particles at three particle/cell ratios, such as 50:1, 100:1, and 200:1, which respectively corresponds to siRNA dosages of 25 nM, 50 nM, and 100 nM. FIG. 19A and FIG. 19B revealed that all three types of pSi particles, i.e., pSi, pSi-PEI and pSi-PEI/siRNA, exhibited similar level of cytokine release to the cells treated with PBS, suggesting that they did not induce any significant increase in cytokine release for the particle/cell ratios employed. These data further confirmed the remarkable biocompatibility of the pSi particles.

The above-mentioned toxicity data was unexpected because PEI is known to induce cytotoxicity, specifically due to strong interaction between the cationic PEI and the anionic cell membrane. The lack of cytotoxicity from the hybrid delivery system may be related to the superior biocompatibility of the pSi matrix, which confers a "stealth" property for the PEI/siRNA nanoparticles anchored inside the pore. In accordance with those observations for the PEGylated PEI, the stealth property indeed dramatically diminished or eliminated the direct contact between PEI and the cells when pSi-PEI/siRNA particles were applied. Only when the pSi matrix was degraded gradually, the PEI/siRNA nanoparticles could be released in a sustained manner.

It should be pointed out that such findings are in contrast to those observed for conventional PEI-based gene delivery systems, in which a large portion of free PEI chains indeed contribute to apparent cytotoxicity (Clamme et al., 2003). However, in the pSi-PEI conjugation approach described here, the free PEI was separated very efficiently, and thus removed from the pSi-PEI particles by means of centrifugation, which led, in turn, to minimal toxicity. One additional advantage rendered by the pSi-PEI conjugation approach was the remarkable reduction of the initial release of PEI/siRNA nanocomplexes from the pore interior, in contrast to the traditional PEI-based siRNA delivery systems, which also accounts for decreased toxicity.

In Vivo Biocompatibility Evaluation.

In vivo biocompatibility evaluation was performed by treating FBV mice with pSi-PEI particles complexed with siRNA (including siSCR or siATM) at a therapeutic dosage of 15 μg or a supra-therapeutic dosage of 75 μg per mouse. As shown in FIG. 20, there was no body weight change or behavior change during a 15-day treatment period.

Fifteen days after the treatments, blood samples were collected for biochemical and hematological analyses in order to assess potential damage to major organs (i.e., liver or renal function) (see e.g., FIG. 21A-FIG. 21C). In comparison to the PBS-treated group, there was no significant difference in biomarker activity or concentration, such as aspartate aminotransferase (AST), alanine aminotransferase (ALT), and alkaline phosphatase (ALKP) for liver function (FIG. 21A), and blood urea nitrogen (BUN) and creatinine for renal function (FIG. 21B). Likewise, hematological analysis, including white blood cell (WBC), lymphocyte (LYMPH), granulocyte (GRAN), and monocyte (MONO), did not show significant difference between the control and the siRNA-treated groups (FIG. 21C). These in vivo biocompatibility results are consistent with the in vitro results mentioned previously. In additon, the significant biocompatibility of the pSi-PEI particles as siRNA delivery system was demonstrated with the histological examination of the major tissues such as brain, heart, kidney, liver, lung, and spleen of the control and treatment groups. As shown in FIG. 22, no apparent morphological changes were observed. Overall, this data was demonstrative of the superior biocompatibility utilizing pSi-PEI particles as delivery agents for siRNA-based therapeutics.

SUMMARY

The present example demonstrates that PEI-conjugated pSi particles represent excellent candidates for the facile preparation of a non-toxic delivery system, and can facilitate the sustained delivery of therapeutic constructs (such as siRNA) to human breast cancer cells. In vitro studies demonstrated that the resultant siRNA-containing particles could be internalized into cells, where they effectively silenced the target gene. Furthermore, remarkable biocompatibility was observed both in vitro and in vivo. In addition to significantly simplifying the manufacturing process for the RNAi-based therapeutics, one important implication of this innovative strategy is that such delivery platforms can be easily adapted for a multiptude of clinical applications by merely adjusting the siRNA of concern. Therefore, such a universal the versatility of this siRNA delivery platform is expected to have great potential in personalized cancer therapy.

REFERENCES

The following references, to the extent that they provide exemplary procedural or other details supplementary to those set forth herein, are specifically incorporated herein in their entirety by express reference thereto:

U.S. Pat. No. 5,543,158 to Gref et al., entitled "Biodegradable injectable nanoparticles."

U.S. Pat. No. 5,641,515 to Ramtoola et al., entitled "Controlled release biodegradable nanoparticles containing insulin."

U.S. Pat. No. 5,399,363 to Liversidge et al., entitled "Surface modified anticancer nanoparticles."

ADACHI, R et al., "ErbB2 down-regulates microRNA-205 in breast cancer," *Biochem. Biophys. Res. Commun.*, 411(4):804-808 (2011).

ADAMS, B D et al., "The micro-ribonucleic acid (miRNA) miR-206 targets the human estrogen receptor-alpha (ER-alpha) and represses ERalpha messenger RNA and protein expression in breast cancer cell lines," *Mol. Endocrinol.*, 21(5):1132-1147 (2007).

AKINC, A et al., "A combinatorial library of lipid-like materials for delivery of RNAi therapeutics," *Nat. Biotechnol.*, 26(5):561-569 (2008).

AL-HAJJ, M et al., "Therapeutic implications of cancer stem cells," *Curr. Opin. Genet. Dev.*, 14(1):43-47 (2004).

ALIABADI, H M et al., "Supramolecular assemblies in functional siRNA delivery: where do we stand?" *Biomaterials*, 33(8):2546-2569 (2012).

ANANTA, J S et al., "Geometrical confinement of gadolinium-based contrast agents in nanoporous particles enhances T1 contrast," *Nat. Nanotechnol.*, 5(11):815-821 (2010).

BALLARIN-GONZALEZ, B et al., "Polycation-based nanoparticles for RNAi-mediated cancer treatment," *Cancer Lett.*, 352(1):66-80 (2013).

BALUK, P et al., "Cellular abnormalities of blood vessels as targets in cancer," *Curr. Opin. Genet. Dev.*, 15(1):102-111 (2005).

BASTILLO, B et al., "Intracellular delivery of siRNA by polycationic superparamagnetic nanoparticles," *J. Drug Del.*, 2012:218940 (2012).

BATIST, G et al., "Reduced cardiotoxicity and preserved antitumor efficacy of liposome-encapsulated doxorubicin and cyclophosphamide compared with conventional doxorubicin and cyclophosphamide in a randomized, multicenter trial of metastatic breast cancer," *J. Clin. Oncol.*, 19(5):1444-1454 (2001).

BELLOCQ, N C et al., "Transferrin-containing, cyclodextrin polymer-based particles for tumor-targeted gene delivery," *Bioconjug. Chem.*, 14(6):1122-1132 (2003).

BERNS, K et al., "A functional genetic approach identifies the PI3K pathway as a major determinant of trastuzumab resistance in breast cancer," *Cancer Cell.*, 12(4):395-402 (2007).

BHATTARAI, S R et al., "Enhanced gene and siRNA delivery by polycation-modified mesoporous silica nanoparticles loaded with chloroquine," *Pharm. Res.*, 27(12):2556-2568 (2010).

CANMAN, C E, and LIM, D S, "The role of ATM in DNA damage responses and cancer," *Oncogene*, 17(25):3301-3308 (1998).

CANTLEY, L C et al., "AACR Cancer Progress Report 2012," *Clin. Cancer Res.*, 18(21 Suppl):S 1-S 100 (2012).

CHANG, R S et al., "Cationic drug-derived nanoparticles for multifunctional delivery of anticancer siRNA," *Biomaterials*, 32(36):9785-9795 (2011).

CHIAPPINI, C et al., "Tailored porous silicon microparticles: fabrication and properties," *Chem. Phys. Chem.*, 11(5):1029-35 (2010).

CLAMME, J P et al., "Monitoring of the formation and dissociation of polyethylenimine/DNA complexes by two photon fluorescence correlation spectroscopy," *Biophys. J.*, 84(3):1960-1968 (2003).

CONG, L, and ZHANG, F, "Genome engineering using CRISPR/Ca9 system," *Methods Mol. Biol.*, 1239:197-217 (2015).

CUBILLOS-RUIZ, J R et al., "Polyethylenimine-based siRNA nanocomplexes reprogram tumor-associated dendritic cells via TLR5 to elicit therapeutic antitumor immunity," *J. Clin. Invest.*, 119(8):2231-2244 (2009).

DAVE, B et al., "Selective small molecule Stat3 inhibitor reduces breast cancer tumor-initiating cells and improves recurrence free survival in a human-xenograft model," *PLoS One*, 7:e30207 (2012).

DAVE, B et al., "Targeting RPL39 and MLF2 reduces nitric oxide synthase signaling," *Proc. Natl. Acad Sci. USA*, 111:8838-8843 (2014).

DAVIS, M E et al., "Evidence of RNAi in humans from systemically administered siRNA via targeted nanoparticles," *Nature*, 464(7291):1067-1070 (2010).

DECUZZI, P et al., "Size and shape effects in the biodistribution of intravascularly injected particles," *J. Contr. Rel.*, 141(3):320-327 (2010).

DI LEVA, G et al., "*MicroRNA cluster* 221-222 and estrogen receptor alpha interactions in breast cancer," *J. Natl. Cancer Inst.*, 102(10):706-721 (2010).

ELBASHIR, S M et al., "Duplexes of 21-nucleotide RNAs mediate RNA interference in cultured mammalian cells," *Nature*, 411(6836):494-498 (2001).

FANG, I S, and TREWYN, B G, "Application of mesoporous silica nanoparticles in intracellular delivery of molecules and proteins," *Methods Enzymol.*, 508:41-59 (2012).

FAUMAN, E B et al., "Structure-based druggability assessment-identifying suitable targets for small molecule therapeutics," *Curr. Opin. Chem. Biol.*, 15(4):463-468 (2011).

FELBER, A E et al., "pH-sensitive vesicles, polymeric micelles, and nanospheres prepared with polycarboxylates," *Adv. Drug Deliv. Rev.*, 64(11):979e92 (2012).

FENSKE, D B et al., "Liposomal nanomedicines," *Expert Opin. Drug Deliv.*, 5(1):25-44 (2008).

FERRARI, M, "Frontiers in cancer nanomedicine, "directing mass transport through biological barriers," *Trends Biotechnol.*, 28(4):181-188 (2010a).

FERRARI, M, "Vectoring siRNA therapeutics into the clinic," *Nat. Rev. Clin. Oncol.*, 7(9):485-486 (2010b).

FERRARI, M, "Cancer nanotechnology: opportunities and challenges," *Nat. Rev. Cancer*, 5(3):161e71 (2005).

FIRE, A et al., "Potent and specific genetic interference by double-stranded RNA in *Caenorhabditis elegans*," *Nature*, 391(6669):806-811 (1998).

FISCHER, D et al., "In vitro cytotoxicity testing of polycations: influence of polymer structure on cell viability and hemolysis," *Biomaterials*, 24(7):1121-31 (2003).

FITZGERALD et al., "Effect of an RNA interference drug on the synthesis of proprotein convertase . . . . Phase 1 trial," *Lancet*, 383:60-68 (2014).

GEYSEN, H M et al., "Use of peptide synthesis to probe viral antigens for epitopes to a resolution of a single amino acid," *Proc. Natl. Acad. Sci. USA*, 81(13):3998-4002 (1984).

GODIN, B et al., "Discoidal porous silicon particles: fabrication and biodistribution in breast cancer bearing mice," *Adv. Funct. Mater*, 22(20):4225-4235 (2012).

GODIN, B et al., "Multistage nanovectors: from concept to novel imaging contrast agents and therapeutics," *Accounts Chem. Res.*, 44(10):979e89 (2011).

*Goodman & Gilman's The Pharmacological Basis of Therapeutics* Tenth edition, Hardman, J G et al., (Eds.), McGraw-Hill Professional (2001).

GRADISHAR, W J et al., "Phase III trial of nanoparticle albumin-bound paclitaxel compared with polyethylated castor oil-based paclitaxel in women with breast cancer," *J. Clin. Oncol.*, 23(31):7794-7803 (2005).

GREGORY, P A et al., "The miR-200 family and miR-205 regulate epithelial to mesenchymal transition by targeting ZEB1 and SIP1," *Nat. Cell Biol.*, 10(5):593-601 (2008).

GRIBSKOV, M and BURGESS, R R, "Sigma factors from *E. coli, B. subtilis*, phage SP01, and phage T4 are homologous proteins," *Nucleic Acids Res.*, 14(16):6745-6763 (1986).

HAN, M et al., "Antagonism of miR-21 reverses epithelial-mesenchymal transition and cancer stem cell phenotype through AKT/ERK1/2 inactivation by targeting PTEN," *PLoS One*, 7:e39520 (2012).

HORNUNG, V et al., "Sequence-specific potent induction of IFN-α by short interfering RNA in plasmacytoid dendritic cells through TLR7," *Nat. Med.*, 11(3):263-270 (2005).

HOWARD, K A et al., "Polycation-based nanoparticle delivery for improved RNA interference therapeutics," *Exp. Opin. Biol. Ther.*, 7(12):1811-1822 (2007).

HSU, S-H et al., "Cationic lipid nanoparticles for therapeutic delivery of siRNA and miRNA to murine liver tumor," *Nanomedicine*, 9(8):1169-1180 (2013).

HUNTER, A C, "Molecular hurdles in polyfectin design and mechanistic background to polycation induced cytotoxicity," *Adv. Drug Deliv. Rev.*, 58(14):1523-1531 (2006).

IORIO, M V et al., "microRNA-205 regulates HER3 in human breast cancer," *Cancer Res.*, 69(6):2195-2200 (2009).

JOHNSON, S M et al., "RAS is regulated by the let-7 microRNA family," *Cell*, 120(5):635-647 (2005).

JONES, S et al., "Core signaling pathways in human pancreatic cancers revealed by global genomic analyses," *Science*, 321(5897):1801-1806 (2008).

JUDGE, A D et al., "Confirming the RNAi-mediated mechanism of action of siRNA-based cancer therapeutics in mice," *J. Clin. Invest.*, 119(3):661-673 (2009).

JUDGE, A D et al., "Sequence-dependent stimulation of the mammalian innate immune response by synthetic siRNA," *Nat. Biotechnol.*, 23(4):457-462 (2005).

KIM, H S et al., "Functional roles of Src and Fgr in ovarian carcinoma," *Clin. Cancer Res.*, 17(7):1713-1721 (2011).

LANDEN, C N Jr. et al., "Therapeutic EphA2 gene targeting in vivo using neutral liposomal small interfering RNA delivery," *Cancer Res.*, 65:6910-6918 (2005).

LEE, J B et al., "Self-assembled RNA interference microsponges for efficient siRNA delivery," *Nat. Mater.*, 11(4):316-322 (2012).

LEE, J E et al., "Multifunctional mesoporous silica nanocomposite nanoparticles for theranostic applications," *Accounts Chem. Res.*, 44(10):893-902 (2011).

LI, J et al., "Leukaemia disease genes: large-scale cloning and pathway predictions," *Nat. Genet.*, 23(3):348-353 (1999).

LI, S D, and HUANG, L, "Gene therapy progress and prospects: non-viral gene therapy by systemic delivery," *Gene Ther.*, 13(18):1313e9 (2006).

LI, X et al., "A mesoporous silica nanoparticle PEI fusogenic peptide system for siRNA delivery in cancer therapy," *Biomaterials*, 34(4):1391e401 (2013).

LI, X et al., "Intrinsic resistance of tumorigenic breast cancer cells to chemotherapy," *J. Natl. Cancer Inst.*, 100(9):672-679 (2008).

LIN, J and ALEXANDER-KATZ, A, "Cell membranes open "doors" for cationic nanoparticles/biomolecules: insights into uptake kinetics," *ACS Nano*, 7(12):10799-10808 (2013).

MACDIARMID, J A et al., "Sequential treatment of drug-resistant tumors with targeted minicells containing siRNA or a cytotoxic drug," *Nat. Biotechnol.*, 27(7):643-651 (2009).

MAEDA, H, "The enhanced permeability and retention (EPR) effect in tumor vasculature: the key role of tumor-selective macromolecular drug targeting," *Adv. Enzyme Regul.*, 41(1): 189-207 (2001).

MAKLEY, L N, and GESTWICKI, J E, "Expanding the number of 'druggable' targets: non-enzymes and protein-protein interactions," *Chem. Biol. Drug Des.*, 81(1):22-32 (2013).

MAROTTA, L L et al., "The JAK2/STAT3 signaling pathway is required for growth of CD44(+)CD24(−) stem cell-like breast cancer cells in human tumors," *J. Clin. Invest.*, 121(7):2723-2735 (2011).

MARTELLO, G et al., "A microRNA targeting dicer for metastasis control," *Cell*, 141(7):1195-1207 (2010).

MATSUMURA, V, and MAEDA, H, "A new concept for macromolecular therapeutics in cancer chemotherapy: mechanism of tumoritropic accumulation of proteins and the antitumor agent smancs," *Cancer Res.*, 46(12 Pt. 1):6387-6392 (1986).

MERDAN, T et al., "Prospects for cationic polymers in gene and oligonucleotide therapy against cancer," *Adv. Drug Deliv. Rev.*, 54(5):715e58 (2002).

MIYATA, K et al., "Rational design of smart supramolecular assemblies for gene delivery: chemical challenges in the creation of artificial viruses," *Chem. Soc. Rev.*, 41(7): 2562e74 (2012).

MOGHIMI, S M et al., "A two-stage poly(ethylenimine)-mediated cytotoxicity: implications for gene transfer/therapy," *Mol. Ther.*, 11(6):990-995 (2005).

MONTEAGUDO, S et al., "Inhibition of p42 MAPK using a nonviral vectordelivered siRNA potentiates the antitumor effect of metformin in prostate cancer cells," *Nanomedicine (Lond)*, 7(4):493-506 (2012).

NA, H-K et al., "Efficient functional delivery of siRNA using mesoporous silica nanoparticles with ultralarge pores," *Small*, 8(11):1752e61 (2012).

NAVARRO, G et al., "P-glycoprotein silencing with siRNA delivered by DOPE-modified PEI overcomes doxorubicin resistance in breast cancer cells," *Nanomedicine (Lond)*, 7(1):65-78 (2012).

NEEDLEMAN, S B and WUNSCH, C D, "A general method applicable to the search for similarities in the amino acid sequence of two proteins," *J. Mol. Biol.*, 48(3):443-453 (1970).

NISHIYAMA, N, and KATAOKA, K, "Current state, achievements, and future prospects of polymeric micelles as nanocarriers for drug and gene delivery," *Pharmacol. Therapeut.*, 112(3):630e48 (2006).

O'BRIEN, M E et al., "Reduced cardiotoxicity and comparable efficacy in a phase III trial of pegylated liposomal doxorubicin HCl (CAELYX/Doxil) versus conventional doxorubicin for first-line treatment of metastatic breast cancer," *Ann. Oncol.*, 15(3):440-449 (2004).

OGRIS, M, and WAGNER, E, "Targeting tumors with non-viral gene delivery systems," *Drug Discov. Today*, 7(8):479e85 (2002).

PEARSON, W R and LIPMAN, D J, "Improved tools for biological sequence comparison," *Proc. Natl. Acad. Sci. USA*, 85(8):2444-2448 (1988).

PECOT, C V et al., "RNA interference in the clinic: challenges and future directions," *Nat. Rev. Cancer*, 11(1):59-67 (2011).

PETERSEN, H et al., "Polyethylenimine-graft-poly(ethylene glycol) copolymers: influence of copolymer block structure on DNA complexation and biological activities as gene delivery system," *Bioconjug. Chem.*, 13(4):845-854 (2002).

PONTI, D et al., "Isolation and in vitro propagation of tumorigenic breast cancer cells with stem/progenitor cell properties," *Cancer Res.*, 65(13):5506-5511 (2005).

*Protein Immobilization: Fundamentals and Applications* (Bioprocess Technology), Taylor, R. (Ed.) pp. 109-110, CRC Press (January 1991).

QASED, A B et al., "MicroRNA-18a upregulates autophagy and ataxia telangiectasia mutated gene expression in HCT116 colon cancer cells," *Mal. Med. Report*, 7(2):559-564 (2013).

RADU, D R et al., "A polyamidoamine dendrimer-capped mesoporous silica nanosphere-based gene transfection reagent," *J. Am. Chem. Soc.*, 126(41): 13216-13217 (2004).

RUSS, V et al., "Oligoethylenimine-grafted polypropylenimine dendrimers as degradable and biocompatible synthetic vectors for gene delivery," *J. Control Release*, 132(2): 131-140 (2008).

RYU, S et al., "Suppression of miRNA-708 by polycomb group promotes metastases by calcium-induced cell migration," *Cancer Cell*, 23(1):63-76 (2013).

SAMPSON, V B et al., "MicroRNA let-7a down-regulates MYC and reverts MYCinduced growth in Burkitt lymphoma cells," *Cancer Res.*, 67(20):9762-9770 (2007).

SANTEL, A et al., "A novel siRNA-lipoplex technology for RNA interference in the mouse vascular endothelium," *Gene Ther.*, 13(16):1222-1234 (2006).

SCHLABACH, M R et al., "Cancer proliferation gene discovery through functional genomics," *Science*, 319 (5863): 620-624 (2008).

SEAVEY, M M, and DOBRZANSKI, P, "The many faces of Janus kinase," *Biochem Pharmacol.*, 83(9): 1136-1145 (2012).

SEGAL, A et al., "Liver as a target for oligonucleotide therapeutics," *J. Hepatol.*, 59:1354-1359 (2013).

SEMPLE, S C et al., "Rational design of cationic lipids for siRNA delivery," *Nat. Biotechnol.*, 28(2):172-176 (2010).

SHAHZAD, M M et al., "Dual targeting of EphA2 and FAK in ovarian carcinoma," *Cancer Biol. Ther.*, 8(11):1027-1034 (2009).

SHEN, H et al., "Cooperative, nanoparticle-enabled thermal therapy of breast cancer." *Adv. Healthcare Mater*, 1(1): 84-89 (2012).

SHEN, H et al., "Delivery of gene silencing agents for breast cancer therapy," *Breast Cancer Res.*, 15(3):205 (2013a).

SHEN, H et al., "Enhancing chemotherapy response with sustained EphA2 silencing using multistage vector delivery," *Clin. Cancer Res.*, 19(7):1806-1815 (2013b).

SHEN, H et al., "Nanovector delivery of siRNA for cancer therapy," *Cancer Gene Ther.*, 19(6):367-373 (2012).

SHEN, J et al., "Cyclodextrin and polyethyleneimine functionalized mesoporous silica nanoparticles for delivery of siRNA cancer therapeutics," *Theranostics*, 4(5):487-497 (2014).

SHEN, J et al., "ER stress regulation of ATF6 localization by dissociation of BiP/GRP78 binding and unmasking of Golgi localization signals," *Dev. Cell*, 3(1):99-111 (2002).

SHEN, J et al., "High capacity nanoporous silicon carrier for systemic delivery of gene silencing therapeutics," *ACS Nano*, 7(11):9867-9880 (2013).

SONAWANE, N D et al., "Chloride accumulation and swelling in endosomes enhances DNA transfer by polyamine-DNA polyplexes," *J. Blot. Chem.*, 278(45): 44826-44831 (2003).

STRUMBERG et al., "Phase I clinical development of Atu027, a siRNA formulation targeting PKN3 in patients with advanced solid tumors," *Int. J. Clin. Pharmacol. Ther.*, 50:76-78 (2012).

SUZUKI, T et al., "New genes involved in cancer identified by retroviral tagging," *Nat. Genet.*, 32(1):166-174 (2002).

TANAKA, T et al., "Sustained small interfering RNA delivery by mesoporous silicon particles," *Cancer Res.*, 70(9): 3687-3696 (2009).

TASCIOTTI, E et al., "Mesoporous silicon particles as a multistage delivery system for imaging and therapeutic applications," *Nat. Nanotechnol.*, 3(3):151-157 (2008).

TATEDA, K et al., "Lipopolysaccharide-induced lethality and cytokine production in aged mice," *Infect. Immun.*, 64(3):769-774 (1996).

THOMAS, M, and KLIBANOV, A M, "Conjugation to gold nanoparticles enhances polyethylenimine's transfer of plasmid DNA into mammalian cells," *Proc. Natl. Acad. Sci. USA*, 100(16):9138-9143 (2003).

UNSAL-KACMAZ, K et al., "The interaction of PKN3 with RhoC promotes malignant growth," *Mol Oncol.*, 6(3): 284-298 (2012).

VAN DE VEN, A L et al., "Rapid tumoritropic accumulation of systemically injected plateloid particles and their biodistribution," *J. Control Release*, 158(1):148-155 (2012).

VIVERO-ESCOTO, J L et al., "Mesoporous silica nanoparticles for intracellular controlled drug delivery," *Small*, 6(18):1952-1967 (2010).

WANG, T et al., "Design of multifunctional non-viral gene vectors to overcome physiological barriers: dilemmas and strategies," *Int. J. Pharm.*, 427(1):3e20 (2012).

WOOD, L D et al., "The genomic landscapes of human breast and colorectal cancers," *Science*, 318(5853):1108-1113 (2007).

XIA, T et al., "Polyethyleneimine coating enhances the cellular uptake of mesoporous silica nanoparticles and allows safe delivery of siRNA and DNA constructs," *ACS Nano*, 3(10):3273e86 (2009).

XU, R et al., "Multistage vectored siRNA targeting ataxia-telangiectasia mutated for breast cancer therapy," *Small*, 9(9-10):1799-1808 (2013).

YAO, Y D et al., "Targeted delivery of PLK1-siRNA by ScFv suppresses Her2+ breast cancer growth and metastasis," *Sci. Transl. Med.*, 4(130):130ra148 (2012).

YU, F et al., "let-7 regulates self renewal and tumorigenicity of breast cancer cells," *Cell*, 131(6):1109-1123 (2007).

YU, Z et al., "microRNA 17/20 inhibits cellular invasion and tumor metastasis in breast cancer by heterotypic signaling," *Proc. Natl. Acad. Sci. USA*, 107(18):8231-8236 (2010).

ZHANG, M, and KATAOKA, K, "Nano-structured composites based on calcium phosphate for cellular delivery of therapeutic and diagnostic agents," *Nano. Today*, 4(6): 508e17 (2009).

ZHANG, M et al., "Polycation-functionalized nanoporous silicon particles for gene silencing on breast cancer cells," *Biomaterials*, 35(1):423-431 (2014).

ZIMMERMANN, T S et al., "RNAi-mediated gene silencing in non-human primates," *Nature*, 441:111-114 (2006).

ZUCKERMAN, J E et al., "Polycation-siRNA nanoparticles can disassemble at the kidney glomerular basement membrane," *Proc. Natl. Acad. Sci. USA*, 109(8):3137-3142 (2012).

It should be understood that the examples and embodiments described herein are for illustrative purposes only and that various modifications or changes in light thereof will be suggested to persons skilled in the art and are to be included within the spirit and purview of this application and the scope of the appended claims. All references, including publications, patent applications and patents, cited herein are hereby incorporated by reference to the same extent as if each reference was individually and specifically indicated to be incorporated by reference and was set forth in its entirety herein. Recitation of ranges of values herein are merely intended to serve as a shorthand method of referring individually to each separate value falling within the range, unless otherwise indicated herein, and each separate value is incorporated into the specification as if it were individually recited herein.

The description herein of any aspect or embodiment of the invention using terms such as "comprising," "having," "including," or "containing," with reference to an element or elements, is intended to provide support for a similar aspect or embodiment of the invention that "consists of," "consists essentially of," or "substantially comprises," that particular element or elements, unless otherwise stated or clearly contradicted by context (e.g., a composition described herein as comprising a particular element should be understood as also describing a composition consisting of that element, unless otherwise stated or clearly contradicted by context).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents that are chemically and/or physiologically related may be substituted for the agents described herein while the same or similar results would be achieved.

All such similar substitutes and modifications apparent to those skilled in the art are deemed to be within the spirit, scope and concept of the invention as defined by the appended claims.

What is claimed is:

1. A composition for the sustained-release delivery of an active agent to a target cell of a subject in need thereof, comprising:
   (a) a population of polycation-functionalized, nanoporous, silicon first-stage particles; and
   (b) a population of second-stage particles contained substantially within the interior of the population of the first-stage particles, and wherein the second-stage particles comprise a first active agent;
   wherein the polycation comprises poly-arginine, poly-lysine, chitosan, dendrimer, polyethyleneimine, or any combination thereof;
   wherein the first active agent is released from the second-stage particles, and self-assembles into one or more nanoparticles, upon contacting an aqueous environment;
   wherein the polycation is operably linked to a first portion of the outer surface of the population of first-stage particles by conjugation or by functionalization with 3-aminopropyl-triethoxysilane; and
   further wherein the composition is formulated for storage between about 0° C. and about 22° C. for a period of about one week to about six months, without a substantial degradation or a substantial loss of biological activity.

2. The composition of claim 1, wherein the population of first-stage nanoporous silicon particles is biocompatible and degradable.

3. The composition of claim 1, formulated for freezing, freeze-drying, dehydration, desiccation, or lyophilization.

4. The composition of claim 1, formulated for mammalian administration.

5. The composition of claim 4, formulated for system administration to a human.

6. The composition of claim 1, further comprising a second, distinct population of nanoparticles or microparticles.

7. A kit comprising: the composition of claim 1, and a set of instructions for using the composition in the treatment or amelioration of one or more symptoms of a mammalian disease, disorder, or dysfunction.

8. The kit of claim 7, further comprising: (a) a therapeutic agent; (b) a first diagnostic agent; or (c) a combination of (a) and (b).

9. A method of targeting gene silencing in a mammalian cancer cell, comprising administering to a mammal, an effective amount of the composition of claim 1.

10. A method of treating or ameliorating at least one symptom of cancer in a mammal, the method comprising administering to the mammal a composition comprising a therapeutically-effective amount of the composition of claim 1, and for a time effective to treat or ameliorate at least one symptom of the cancer.

11. The method of claim 10, further comprising administering to the mammal an effective amount of a therapeutic agent selected from the group consisting of a small interfering RNA, an anti-cancer agent, an anti-inflammatory agent, a cytotoxic agent, or any combination thereof.

12. A method of treating, alleviating, or ameliorating at least one symptom of a breast cancer in a human, the method comprising administering to the mammal an amount of the composition of claim 1, and for a time effective to treat, alleviate, or ameliorate at least one symptom of the breast cancer in the human.

13. The kit of claim 7, wherein the mammalian disease is cancer.

14. The kit of claim 13, wherein the mammalian disease is human breast cancer.

15. A pharmaceutical composition comprising:
   (1) (a) a population of polycation-functionalized, nanoporous, silicon first-stage particles; and
      (b) a population of second-stage particles contained substantially within the interior of the population of the first-stage particles, and wherein the second-stage particles comprise a first active agent; and
   (2) a pharmaceutically-acceptable buffer, diluent, solvent, or excipient;
   wherein the polycation comprises poly-arginine, poly-lysine, chitosan, dendrimer, polyethyleneimine, or any combination thereof;
   wherein the first active agent is released from the second-stage particles, and self-assembles into one or more nanoparticles, upon contacting an aqueous environment;
   wherein the polycation is operably linked to a first portion of the outer surface of the population of first-stage particles by conjugation or by functionalization with 3-aminopropyl-triethoxysilane; and
   further wherein the composition is formulated for storage between about 0° C. and about 22° C. for a period of about one week to about six months, without a substantial degradation or a substantial loss of biological activity.

16. A method for treating cancer in a mammal, comprising: administering to the mammal a biologically-effective amount of a pharmaceutical composition that comprises:
- (1) (a) a population of polycation-functionalized, nanoporous, silicon first-stage particles; and
  - (b) a population of second-stage particles contained substantially within the interior of the population of the first-stage particles, and wherein the second-stage particles comprise a first active agent; and
- (2) a pharmaceutically-acceptable buffer, diluent, solvent, or excipient;

wherein the polycation comprises poly-arginine, poly-lysine, chitosan, dendrimer, polyethyleneimine, or any combination thereof;

wherein the first active agent is released from the second-stage particles, and self-assembles into one or more nanoparticles, upon contacting an aqueous environment;

wherein the polycation is operably linked to a first portion of the outer surface of the population of first-stage particles by conjugation or by functionalization with 3-aminopropyl-triethoxysilane; and further wherein the composition is formulated for storage between about 0° C. and about 22° C. for a period of about one week to about six months, without a substantial degradation or a substantial loss of biological activity.

17. The method of claim 16, wherein the mammalian cancer is human breast cancer.

* * * * *